(12) United States Patent
Li et al.

(10) Patent No.: US 9,428,568 B2
(45) Date of Patent: Aug. 30, 2016

(54) COMPOSITIONS AND METHODS FOR MODULATING CELL-CELL FUSION VIA INTERMEDIATE-CONDUCTANCE CALCIUM-ACTIVATED POTASSIUM CHANNELS

(75) Inventors: Jun Li, Ridgefield, CT (US); Agnès Vignery, Branford, CT (US)

(73) Assignees: BOEHRINGER INGELHEIM INTERNATIONAL GMBH, Ingelheim (DE); YALE UNIVERSITY, New Haven, CT (US)

( * ) Notice: Subject to any disclaimer, the term of this patent is extended or adjusted under 35 U.S.C. 154(b) by 474 days.

(21) Appl. No.: 13/128,290

(22) PCT Filed: Nov. 10, 2009

(86) PCT No.: PCT/US2009/006050
§ 371 (c)(1),
(2), (4) Date: Aug. 15, 2011

(87) PCT Pub. No.: WO2010/053584
PCT Pub. Date: May 14, 2010

(65) Prior Publication Data
US 2011/0300152 A1    Dec. 8, 2011

Related U.S. Application Data

(60) Provisional application No. 61/198,823, filed on Nov. 10, 2008, provisional application No. 61/278,317, filed on Oct. 5, 2009.

(51) Int. Cl.
*G01N 33/53* (2006.01)
*C07K 14/705* (2006.01)

(52) U.S. Cl.
CPC .................................. *C07K 14/705* (2013.01)

(58) Field of Classification Search
None
See application file for complete search history.

(56) References Cited

U.S. PATENT DOCUMENTS 7,208,527 B2    4/2007  Gouliaev et al.
2009/0186810 A1 *  7/2009  Zwaal et al. .................... 514/11

FOREIGN PATENT DOCUMENTS

| JP | 2001-520524 A | 10/2001 |
|---|---|---|
| WO | WO 99/03882 A2 | 1/1999 |
| WO | WO 00/50026 A1 | 8/2000 |
| WO | WO 03/004010 A1 | 1/2003 |
| WO | WO 03/074038 A1 | 9/2003 |
| WO | WO 2007/009462 A2 | 1/2007 |
| WO | WO 2007/075849 A2 | 7/2007 |
| WO | WO 2008/089022 A2 | 7/2008 |
| WO | WO 2009/027292 A1 | 3/2009 |

OTHER PUBLICATIONS

NCBI Reference Sequence for potassium intermediate/small conductance calcium-activated channel, subfamily N, member 4 [*Homo sapiens*], Accession No. NP_002241, 1999, pp. 1-2.
Bijlenga, P., et al., "T-type α1H $Ca^{2+}$ channels are involved in $Ca^{2+}$ signaling during terminal differentiation (fusion) of human myoblasts," *Proc. Natl. Acad. Sci. USA*, 2000, vol. 97(13), pp. 7627-7632.
Ishii, T., et al., "A human intermediate conductance calcium-activated potassium channel," *Proc. Natl. Acad. Sci. USA*, 1997, vol. 94, pp. 11651-11656.
Vignery, Agnés, "Macrophage fusion: the making of osteoclasts and giant cells," *JEM*, 2005, vol. 202(3), pp. 337-340.
Wulff, H., et al., Modulators of small- and intermediate-conductance calcium-activating potassium channels and their therapeutic indications, *Current Medicinal Chemistry*, 2007, vol. 14(13), pp. 1437-1457.
Kang, H., et al., "Kcnn4 Is a Regulator of Macrophage Multinucleation in Bone Homeostasis and Inflammatory Disease," *Cell Reports*, Aug. 21, 2014, pp. 1210-1224, vol. 8.
Zambrowicz, B., et al., Predicting drug efficacy: knockouts model pipeline drugs of the pharmaceutical industry, *Current Opinion in Pharmacology*, 2003, pp. 563-570, vol. 3.

* cited by examiner

*Primary Examiner* — Michael Pak
(74) *Attorney, Agent, or Firm* — Alston & Bird LLP

(57) ABSTRACT

Compositions and methods are provided for modulating cell-cell fusion by using agents that modulate expression, activity, or function of intermediate-conductance calcium-activated potassium (SK4) channel. In some embodiments, the compositions and methods of the invention provide for inhibition of multi-nucleated osteoclastogenesis and cell-cell fusion, especially cell fusion involving macrophages. In such embodiments, the compositions can comprise inhibitory nucleic acids, monoclonal antibodies or small molecule inhibitors of the SK4 channels and find use in preventing and/or treating various diseases or disorders including bone loss, autoimmune and inflammatory diseases or disorders, implant and transplant rejection, and cancer metastasis. In other embodiments, the compositions and methods of the invention provide for activation of cell-cell fusion. Also provided are methods to screen for SK4 channel modulators (inhibitors or activators) that modulate cell-cell fusion, particularly macrophage cell fusion.

7 Claims, 16 Drawing Sheets

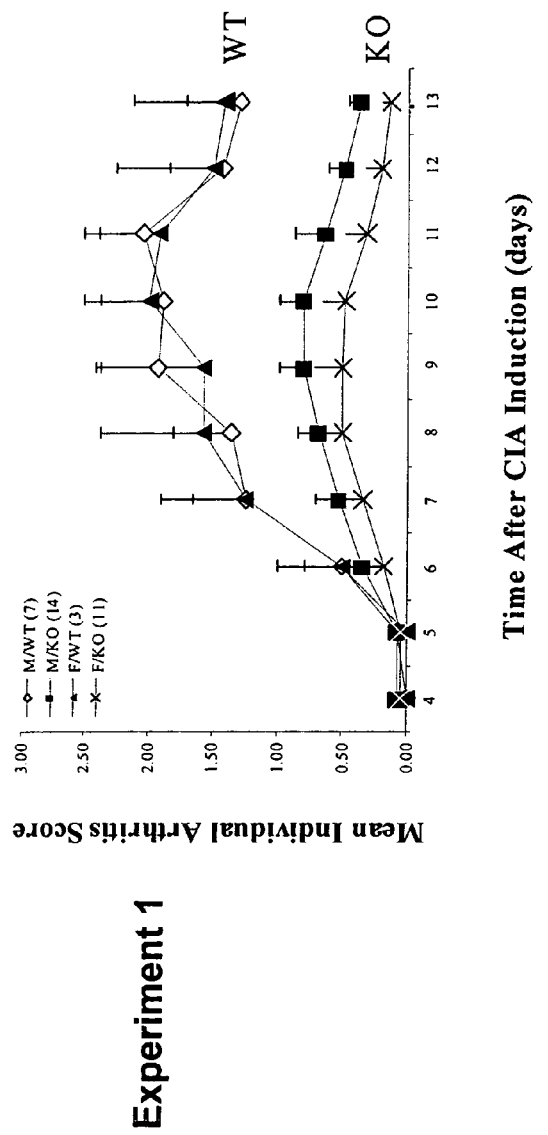
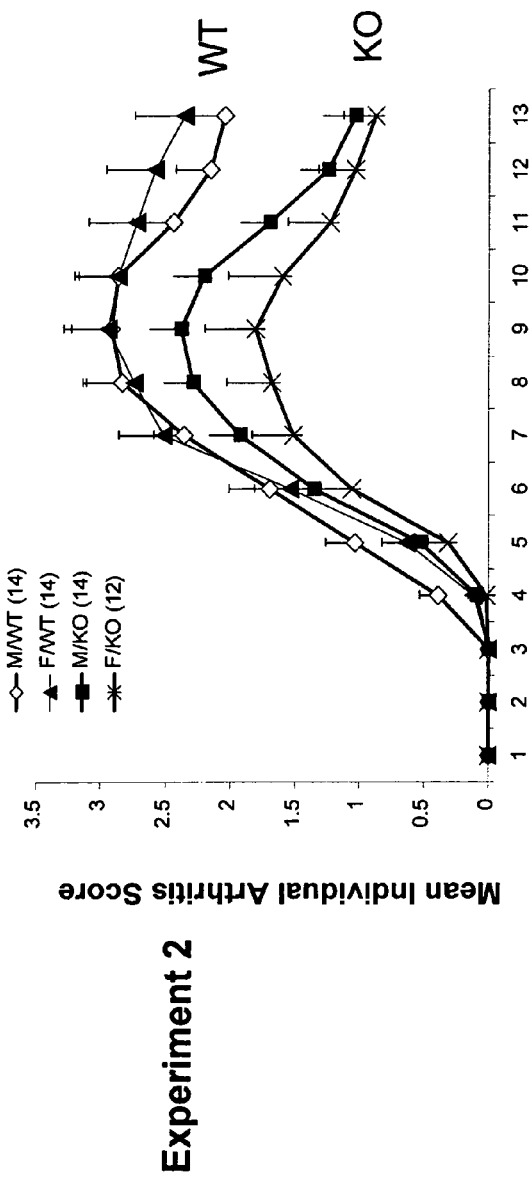

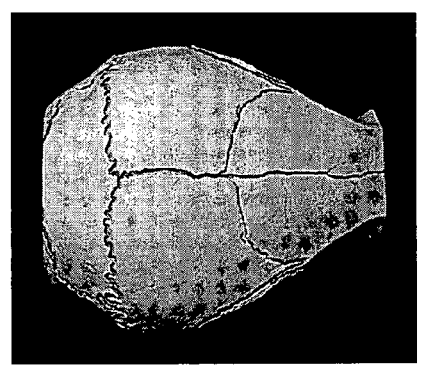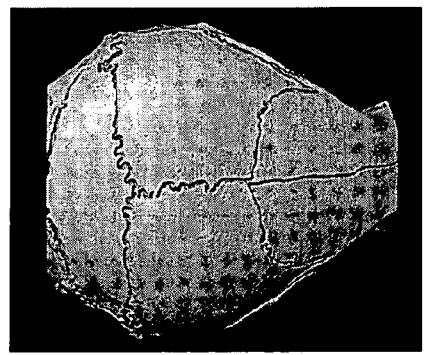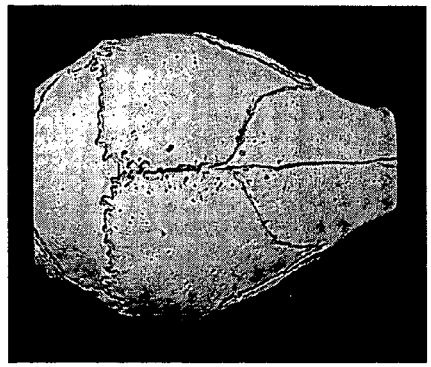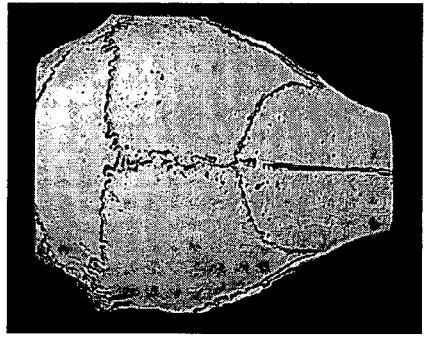
FIG. 14

SEQUENCE LISTING

```
<160> NUMBER OF SEQ ID NOS: 13

<210> SEQ ID NO 1
<211> LENGTH: 2240
<212> TYPE: DNA
<213> ORGANISM: Homo sapiens
<220> FEATURE:
<221> NAME/KEY: CDS
<222> LOCATION: (397)...(1680)
<223> OTHER INFORMATION: Encodes human potassium intermediate/small
      conductance calcium-activated channel, subfamily
      N, member 4 (KCNN4)
<300> PUBLICATION INFORMATION:
<308> DATABASE ACCESSION NUMBER: GenBank Accession No. NM_002250

<400> SEQUENCE: 1
gtccttcggt gtctgggtgt ggtgagtaga ggtgtgtgtc acaaagtaca gaccattgtg      60
tgtgacaaag cccatcgtgt gtctgtgtgt gtctttatcc acgtggatgg acgtctcttt     120
cttgctctgc cccaagacac accctagccc ctccttattc tcaaaagggg gagctgggga     180 gcctcccct accctggggc ctcccctgcc cctcccgcc ctgcctggcc gtcaccactc       240
cccagagggc acagggctct gctgtgcctc agagcaaaag tccagagcc agcagagcag     300 gctgacgacc tgcaagccac agtggctgcc ctgtgcgtgc tgcgaggtgg gggaccctgg     360
```

```
                                                                             -continued gcaggaagct ggctgagccc caagaccccg ggggcc atg ggc ggg gat ctg gtg              414
                                        Met Gly Gly Asp Leu Val
                                        1               5 ctt ggc ctg ggg gcc ttg aga cgc cga aag cgc ttg ctg gag cag gag              462
Leu Gly Leu Gly Ala Leu Arg Arg Arg Lys Arg Leu Leu Glu Gln Glu
            10                  15                  20 aag tct ctg gcc ggc tgg gca ctg gtg ctg gca gga act ggc att gga              510
Lys Ser Leu Ala Gly Trp Ala Leu Val Leu Ala Gly Thr Gly Ile Gly
        25                  30                  35 ctc atg gtg ctg cat gca gag atg ctg tgg ttc ggg ggg tgc tcg tgg              558
Leu Met Val Leu His Ala Glu Met Leu Trp Phe Gly Gly Cys Ser Trp
    40                  45                  50 gcg ctc tac ctg ttc ctg gtt aaa tgc acg atc agc att tcc acc ttc              606
Ala Leu Tyr Leu Phe Leu Val Lys Cys Thr Ile Ser Ile Ser Thr Phe
55                  60                  65                  70 tta ctc ctc tgc ctc atc gtg gcc ttt cat gcc aaa gag gtc cag ctg              654
Leu Leu Leu Cys Leu Ile Val Ala Phe His Ala Lys Glu Val Gln Leu
                75                  80                  85 ttc atg acc gac aac ggg ctg cgg gac tgg cgc gtg gcg ctg acc ggg              702
Phe Met Thr Asp Asn Gly Leu Arg Asp Trp Arg Val Ala Leu Thr Gly
            90                  95                  100 cgg cag gcg gcg cag atc gtg ctg gag ctg gtg gtg tgt ggg ctg cac              750
Arg Gln Ala Ala Gln Ile Val Leu Glu Leu Val Val Cys Gly Leu His
        105                 110                 115 ccg gcg ccc gtg cgg ggc ccg ccg tgc gtg cag gat tta ggg gcg ccg              798
Pro Ala Pro Val Arg Gly Pro Pro Cys Val Gln Asp Leu Gly Ala Pro
    120                 125                 130 ctg acc tcc ccg cag ccc tgg ccg gga ttc ctg ggc caa ggg gaa gcg              846
Leu Thr Ser Pro Gln Pro Trp Pro Gly Phe Leu Gly Gln Gly Glu Ala
135                 140                 145                 150 ctg ctg tcc ctg gcc atg ctg ctg cgt ctc tac ctg gtg ccc cgc gcc              894
Leu Leu Ser Leu Ala Met Leu Leu Arg Leu Tyr Leu Val Pro Arg Ala
                155                 160                 165 gtg ctc ctg cgc agc ggc gtc ctg ctc aac gct tcc tac cgc agc atc              942
Val Leu Leu Arg Ser Gly Val Leu Leu Asn Ala Ser Tyr Arg Ser Ile
            170                 175                 180 ggc gct ctc aat caa gtc cgc ttc cgc cac tgg ttc gtg gcc aag ctt              990
Gly Ala Leu Asn Gln Val Arg Phe Arg His Trp Phe Val Ala Lys Leu
        185                 190                 195 tac atg aac acg cac cct ggc cgc ctg ctg ctc ggc ctc acg ctt ggc              1038
Tyr Met Asn Thr His Pro Gly Arg Leu Leu Leu Gly Leu Thr Leu Gly
    200                 205                 210 ctc tgg ctg acc acc gcc tgg gtg ctg tcc gtg gcc gag agg cag gct              1086
Leu Trp Leu Thr Thr Ala Trp Val Leu Ser Val Ala Glu Arg Gln Ala
215                 220                 225                 230 gtt aat gcc act ggg cac ctt tca gac aca ctt tgg ctg atc ccc atc              1134
Val Asn Ala Thr Gly His Leu Ser Asp Thr Leu Trp Leu Ile Pro Ile
                235                 240                 245 aca ttc ctg acc atc ggc tat ggt gac gtg gtg ccg ggc acc atg tgg              1182
Thr Phe Leu Thr Ile Gly Tyr Gly Asp Val Val Pro Gly Thr Met Trp
            250                 255                 260 ggc aag atc gtc tgc ctg tgc act gga gtc atg ggt gtc tgc tgc aca              1230
Gly Lys Ile Val Cys Leu Cys Thr Gly Val Met Gly Val Cys Cys Thr
        265                 270                 275 gcc ctg ctg gtg gcc gtg gtg gcc cgg aag ctg gag ttt aac aag gca              1278
Ala Leu Leu Val Ala Val Val Ala Arg Lys Leu Glu Phe Asn Lys Ala
    280                 285                 290
```

```
gag aag cac gtg cac aac ttc atg atg gat atc cag tat acc aaa gag      1326
Glu Lys His Val His Asn Phe Met Met Asp Ile Gln Tyr Thr Lys Glu
295                 300                 305                 310 atg aag gag tcc gct gcc cga gtg cta caa gaa gcc tgg atg ttc tac      1374
Met Lys Glu Ser Ala Ala Arg Val Leu Gln Glu Ala Trp Met Phe Tyr
            315                 320                 325 aaa cat act cgc agg aag gag tct cat gct gcc cgc agg cat cag cgc      1422
Lys His Thr Arg Arg Lys Glu Ser His Ala Ala Arg Arg His Gln Arg
        330                 335                 340 aag ctg ctg gcc gcc atc aac gcg ttc cgc cag gtg cgg ctg aaa cac      1470
Lys Leu Leu Ala Ala Ile Asn Ala Phe Arg Gln Val Arg Leu Lys His
            345                 350                 355 cgg aag ctc cgg gaa caa gtg aac tcc atg gtg gac atc tcc aag atg      1518
Arg Lys Leu Arg Glu Gln Val Asn Ser Met Val Asp Ile Ser Lys Met
    360                 365                 370 cac atg atc ctg tat gac ctg cag cag aat ctg agc agc tca cac cgg      1566
His Met Ile Leu Tyr Asp Leu Gln Gln Asn Leu Ser Ser Ser His Arg
375                 380                 385                 390 gcc ctg gag aaa cag att gac acg ctg gcg ggg aag ctg gat gcc ctg      1614
Ala Leu Glu Lys Gln Ile Asp Thr Leu Ala Gly Lys Leu Asp Ala Leu
            395                 400                 405 act gag ctg ctt agc act gcc ctg ggg ccg agg cag ctt cca gaa ccc      1662
Thr Glu Leu Leu Ser Thr Ala Leu Gly Pro Arg Gln Leu Pro Glu Pro
        410                 415                 420 agc cag cag tcc aag tag ctggacccac gaggaggaac caggctactt             1710
Ser Gln Gln Ser Lys
            425 tccccagtac tgaggtggtg acatcgtct ctgccactcc tgacccagcc ctgaacaaag     1770 cacctcaagt gcaaggacca aagggggccc tggcttggag tgggttggct tgctgatggc    1830 tgctggaggg gacgctggct aaagtgggta ggccttggcc cacctgaggc cccaggtggg    1890 aacatggtca ccccccactct gcataccctc atcaaaaaca ctctcactat gctgctatgg   1950 acgacctcca gctctcagtt acaagtgcag gcgactggag gcaggactcc tgggtccctg    2010 ggaaagaggg tactagggc ccggatccag gattctggga ggcttcagtt accgctggcc     2070 gagctgaaga actgggtatg aggctggggc ggggctggag gtggcgcccc ctggtgggac    2130 aacaaagagg acaccatttt tccagagctg cagagagcac ctggtgggga ggaagaagtg    2190 taactcacca gcctctgctc ttatctttgt aataaatgtt aaagccagaa                2240

<210> SEQ ID NO 2
<211> LENGTH: 427
<212> TYPE: PRT
<213> ORGANISM: Homo sapiens

<400> SEQUENCE: 2

Met Gly Gly Asp Leu Val Leu Gly Leu Gly Ala Leu Arg Arg Arg Lys
1               5                   10                  15

Arg Leu Leu Glu Gln Glu Lys Ser Leu Ala Gly Trp Ala Leu Val Leu
            20                  25                  30

Ala Gly Thr Gly Ile Gly Leu Met Val Leu His Ala Glu Met Leu Trp
        35                  40                  45

Phe Gly Gly Cys Ser Trp Ala Leu Tyr Leu Phe Leu Val Lys Cys Thr
    50                  55                  60

Ile Ser Ile Ser Thr Phe Leu Leu Leu Cys Leu Ile Val Ala Phe His
65                  70                  75                  80
```

```
Ala Lys Glu Val Gln Leu Phe Met Thr Asp Asn Gly Leu Arg Asp Trp
                85                  90                  95

Arg Val Ala Leu Thr Gly Arg Gln Ala Gln Ile Val Leu Glu Leu
            100                 105                 110

Val Val Cys Gly Leu His Pro Ala Pro Val Arg Gly Pro Pro Cys Val
            115                 120                 125

Gln Asp Leu Gly Ala Pro Leu Thr Ser Pro Gln Pro Trp Pro Gly Phe
    130                 135                 140

Leu Gly Gln Gly Glu Ala Leu Leu Ser Leu Ala Met Leu Leu Arg Leu
145                 150                 155                 160

Tyr Leu Val Pro Arg Ala Val Leu Leu Arg Ser Gly Val Leu Leu Asn
                165                 170                 175

Ala Ser Tyr Arg Ser Ile Gly Ala Leu Asn Gln Val Arg Phe Arg His
            180                 185                 190

Trp Phe Val Ala Lys Leu Tyr Met Asn Thr His Pro Gly Arg Leu Leu
        195                 200                 205

Leu Gly Leu Thr Leu Gly Leu Trp Leu Thr Thr Ala Trp Val Leu Ser
    210                 215                 220

Val Ala Glu Arg Gln Ala Val Asn Ala Thr Gly His Leu Ser Asp Thr
225                 230                 235                 240

Leu Trp Leu Ile Pro Ile Thr Phe Leu Thr Ile Gly Tyr Gly Asp Val
                245                 250                 255

Val Pro Gly Thr Met Trp Gly Lys Ile Val Cys Leu Cys Thr Gly Val
            260                 265                 270

Met Gly Val Cys Cys Thr Ala Leu Leu Val Ala Val Ala Arg Lys
        275                 280                 285

Leu Glu Phe Asn Lys Ala Glu Lys His Val His Asn Phe Met Met Asp
    290                 295                 300

Ile Gln Tyr Thr Lys Glu Met Lys Glu Ser Ala Ala Arg Val Leu Gln
305                 310                 315                 320

Glu Ala Trp Met Phe Tyr Lys His Thr Arg Arg Lys Glu Ser His Ala
                325                 330                 335

Ala Arg Arg His Gln Arg Lys Leu Leu Ala Ala Ile Asn Ala Phe Arg
            340                 345                 350

Gln Val Arg Leu Lys His Arg Lys Leu Arg Glu Gln Val Asn Ser Met
        355                 360                 365

Val Asp Ile Ser Lys Met His Met Ile Leu Tyr Asp Leu Gln Gln Asn
    370                 375                 380

Leu Ser Ser Ser His Arg Ala Leu Glu Lys Gln Ile Asp Thr Leu Ala
385                 390                 395                 400

Gly Lys Leu Asp Ala Leu Thr Glu Leu Leu Ser Thr Ala Leu Gly Pro
                405                 410                 415

Arg Gln Leu Pro Glu Pro Ser Gln Gln Ser Lys
            420                 425

<210> SEQ ID NO 3
<211> LENGTH: 1956
<212> TYPE: DNA
<213> ORGANISM: Mus musculus
<220> FEATURE:
<221> NAME/KEY: CDS
<222> LOCATION: (175)...(1452)
<223> OTHER INFORMATION: Encodes murine potassium intermediate/small
      conductance calcium-activated channel, subfamily
      N, member 4 (KCNN4)
<300> PUBLICATION INFORMATION:
```

<308> DATABASE ACCESSION NUMBER: GenBank Accession No. NM_008433

<400> SEQUENCE: 3

| | |
|---|---|
| ctgctgcagt taccactccc cagagggcac agggctaggc tgtgccttcc agcaaaagtc | 60 |
| ccagagtgag cagaacaggc cgctggcctg gaagccaagc tggctgccat ttgcgtactg | 120 |
| agaggtgggg gaccctgggc aggaagctgg ctgagcccca agacctcagg ggcc atg<br>                                                                                                             Met<br>                                                                                                              1 | 177 |
| ggc ggg gag ctg gtg act ggc ctg ggg gcc ctg aga cgg aga aag cgc<br>Gly Gly Glu Leu Val Thr Gly Leu Gly Ala Leu Arg Arg Arg Lys Arg<br>               5                      10                   15 | 225 |
| ctg ctg gag cag gag aag agg gtg gcc ggc tgg gcg ttg gtg ctg gcg<br>Leu Leu Glu Gln Glu Lys Arg Val Ala Gly Trp Ala Leu Val Leu Ala<br>             20                     25                   30 | 273 |
| gga act ggc atc gga ctc atg gtt ctg cac gct gag atg ttg tgg ttc<br>Gly Thr Gly Ile Gly Leu Met Val Leu His Ala Glu Met Leu Trp Phe<br>    35                      40                     45 | 321 |
| ctg ggc tgc aag tgg gtg ctg tac ctg ctc ctg gtt aag tgt ttg atc<br>Leu Gly Cys Lys Trp Val Leu Tyr Leu Leu Leu Val Lys Cys Leu Ile<br>50                     55                     60                 65 | 369 |
| acc ctg tcc act gcc ttc ctc ctt tgt ctt att gtg gtc ttc cat gcc<br>Thr Leu Ser Thr Ala Phe Leu Leu Cys Leu Ile Val Val Phe His Ala<br>             70                     75                   80 | 417 |
| aag gag gtc cag ctg ttc atg act gac aac ggg ctc cgg gac tgg cgc<br>Lys Glu Val Gln Leu Phe Met Thr Asp Asn Gly Leu Arg Asp Trp Arg<br>               85                     90                   95 | 465 |
| gtg gcg ctg acc cgg cgg cag gtg gcg cag atc ctg ctg gag ctg ttg<br>Val Ala Leu Thr Arg Arg Gln Val Ala Gln Ile Leu Leu Glu Leu Leu<br>            100                   105                 110 | 513 |
| gtg tgc ggg gtg cac ccg gtg ccc cta cgg agc ccg cac tgc gcc ctg<br>Val Cys Gly Val His Pro Val Pro Leu Arg Ser Pro His Cys Ala Leu<br>115                     120                   125 | 561 |
| gcg ggg gag gcc acc gac gcg cag ccc tgg ccg ggt ttc ctg ggc gaa<br>Ala Gly Glu Ala Thr Asp Ala Gln Pro Trp Pro Gly Phe Leu Gly Glu<br>130                     135                   140                 145 | 609 |
| ggc gag gcg ttg ctg tcc ctg gcc atg ctc ctg cgt ctc tac ctg gtg<br>Gly Glu Ala Leu Leu Ser Leu Ala Met Leu Leu Arg Leu Tyr Leu Val<br>               150                   155                 160 | 657 |
| ccc cgc gcg gtg ctg ctg cgc agc ggg gtc ctg ctc aac gcg tcc tac<br>Pro Arg Ala Val Leu Leu Arg Ser Gly Val Leu Leu Asn Ala Ser Tyr<br>            165                   170                 175 | 705 |
| cgc agc atc ggg gcg ctc aac caa gtc cgc ttc cgc cac tgg ttc gtg<br>Arg Ser Ile Gly Ala Leu Asn Gln Val Arg Phe Arg His Trp Phe Val<br>        180                   185                   190 | 753 |
| gcc aag ctg tac atg aac acg cac ccg ggt cgc ctg ctg ctg ggc ctc<br>Ala Lys Leu Tyr Met Asn Thr His Pro Gly Arg Leu Leu Leu Gly Leu<br>195                     200                   205 | 801 |
| acg ctg ggt ctc tgg ctc acc aca gct tgg gtg ctg tct gtg gct gag<br>Thr Leu Gly Leu Trp Leu Thr Thr Ala Trp Val Leu Ser Val Ala Glu<br>210                     215                   220                 225 | 849 |
| agg cag gct gtc aat gcc acg ggg cac ctc aca gac aca ctg tgg ctg<br>Arg Gln Ala Val Asn Ala Thr Gly His Leu Thr Asp Thr Leu Trp Leu<br>               230                   235                 240 | 897 |
| att ccg atc aca ttc ctg acc att ggc tat ggg gac gtg gta cct ggc<br>Ile Pro Ile Thr Phe Leu Thr Ile Gly Tyr Gly Asp Val Val Pro Gly<br>            245                   250                 255 | 945 |
| acc atg tgg ggc aag att gtc tgc ctg tgc acc gga gtc atg ggg gtc<br>Thr Met Trp Gly Lys Ile Val Cys Leu Cys Thr Gly Val Met Gly Val<br>260                     265                   270 | 993 |

```
tgc tgc aca gct ctc ctg gtg gct gtg gtg gct cgg aag ctg gag ttc      1041
Cys Cys Thr Ala Leu Leu Val Ala Val Val Ala Arg Lys Leu Glu Phe
275                 280                 285 aac aag gcg gag aaa cac gtg cac aac ttc atg atg gac atc cat tat      1089
Asn Lys Ala Glu Lys His Val His Asn Phe Met Met Asp Ile His Tyr
290                 295                 300                 305 gcc aaa gag atg aag gag tca gcg gcg cgg ctg ctg cag gaa gcc tgg      1137
Ala Lys Glu Met Lys Glu Ser Ala Ala Arg Leu Leu Gln Glu Ala Trp
            310                 315                 320 atg tac tac aag cac act cga agg aag gac tcc cgg gct gcc cgc aga      1185
Met Tyr Tyr Lys His Thr Arg Arg Lys Asp Ser Arg Ala Ala Arg Arg
            325                 330                 335 cat cag cgc aag atg ctg gcc gcc atc cac acg ttc cgc cag gta cgg      1233
His Gln Arg Lys Met Leu Ala Ala Ile His Thr Phe Arg Gln Val Arg
            340                 345                 350 ctg aaa cac cgg aag ctc cgg gaa caa gtg aat tcc atg gtg gac atc      1281
Leu Lys His Arg Lys Leu Arg Glu Gln Val Asn Ser Met Val Asp Ile
355                 360                 365 tcc aag atg cac atg atc ctg tgc gac ctg cag ctg ggt ctc agc tcc      1329
Ser Lys Met His Met Ile Leu Cys Asp Leu Gln Leu Gly Leu Ser Ser
370                 375                 380                 385 tcg cac cgt gcc ctg gag aag aga atc gac ggt ctg gca gga aag ctg      1377
Ser His Arg Ala Leu Glu Lys Arg Ile Asp Gly Leu Ala Gly Lys Leu
                390                 395                 400 gat gcc ctg aca gag ctg ctc ggc act gct ctg cag caa cag cag cta      1425
Asp Ala Leu Thr Glu Leu Leu Gly Thr Ala Leu Gln Gln Gln Gln Leu
            405                 410                 415 cca gaa ccc agt cag gag gcc aca tag ctccacatga actcacagaa            1472
Pro Glu Pro Ser Gln Glu Ala Thr
            420                 425 gaaccaggct aagtacccaa ggaccgagct caaggacatg ctccctgcca attccgacca    1532
agccccacga taaatcacct caagatgcca ggacccaagt ggatccacgt tgaggtgcat    1592
ggactctggt ggtggcagcc atgagtggac actgaattgg acctcccacg tcaatgggaa    1652
catggccacc actacacata tgccctcatc agaagccctt tctgctgtgc tgctgttcag    1712
gaccccttaa tctctgttgg aggaggaggt gcctggggtc taggatgcta ggaagcttca    1772
gttaaccgcg gcgggtctc gctgaaggaa ccaggtccga gcgacgggag gtgctgcccc     1832 ctggtgaca cctgggaaga tgccgtttcc tcctgattgc agagactgtg ccagaagagg     1892
gtacagggtg ctgctcacca atccacccte atactttgta ataaatggta aacgaagaca    1952
aaaa                                                                 1956

<210> SEQ ID NO 4
<211> LENGTH: 425
<212> TYPE: PRT
<213> ORGANISM: Mus musculus

<400> SEQUENCE: 4

Met Gly Gly Glu Leu Val Thr Gly Leu Gly Ala Leu Arg Arg Arg Lys
1               5                   10                  15

Arg Leu Leu Glu Gln Glu Lys Arg Val Ala Gly Trp Ala Leu Val Leu
            20                  25                  30

Ala Gly Thr Gly Ile Gly Leu Met Val Leu His Ala Glu Met Leu Trp
        35                  40                  45

Phe Leu Gly Cys Lys Trp Val Tyr Leu Leu Leu Val Lys Cys Leu
    50                  55                  60
```

Ile Thr Leu Ser Thr Ala Phe Leu Leu Cys Leu Val Val Phe His
65                  70                  75                  80

Ala Lys Glu Val Gln Leu Phe Met Thr Asp Asn Gly Leu Arg Asp Trp
                85                  90                  95

Arg Val Ala Leu Thr Arg Arg Gln Val Ala Gln Ile Leu Leu Glu Leu
            100                 105                 110

Leu Val Cys Gly Val His Pro Val Pro Leu Arg Ser Pro His Cys Ala
        115                 120                 125

Leu Ala Gly Glu Ala Thr Asp Ala Gln Pro Trp Pro Gly Phe Leu Gly
    130                 135                 140

Glu Gly Glu Ala Leu Leu Ser Leu Ala Met Leu Leu Arg Leu Tyr Leu
145                 150                 155                 160

Val Pro Arg Ala Val Leu Leu Arg Ser Gly Val Leu Leu Asn Ala Ser
                165                 170                 175

Tyr Arg Ser Ile Gly Ala Leu Asn Gln Val Arg Phe Arg His Trp Phe
            180                 185                 190

Val Ala Lys Leu Tyr Met Asn Thr His Pro Gly Arg Leu Leu Leu Gly
        195                 200                 205

Leu Thr Leu Gly Leu Trp Leu Thr Thr Ala Trp Val Leu Ser Val Ala
    210                 215                 220

Glu Arg Gln Ala Val Asn Ala Thr Gly His Leu Thr Asp Thr Leu Trp
225                 230                 235                 240

Leu Ile Pro Ile Thr Phe Leu Thr Ile Gly Tyr Gly Asp Val Val Pro
                245                 250                 255

Gly Thr Met Trp Gly Lys Ile Val Cys Leu Cys Thr Gly Val Met Gly
            260                 265                 270

Val Cys Cys Thr Ala Leu Leu Val Ala Val Ala Arg Lys Leu Glu
        275                 280                 285

Phe Asn Lys Ala Glu Lys His Val His Asn Phe Met Met Asp Ile His
    290                 295                 300

Tyr Ala Lys Glu Met Lys Glu Ser Ala Ala Arg Leu Leu Gln Glu Ala
305                 310                 315                 320

Trp Met Tyr Tyr Lys His Thr Arg Arg Lys Asp Ser Arg Ala Ala Arg
                325                 330                 335

Arg His Gln Arg Lys Met Leu Ala Ala Ile His Thr Phe Arg Gln Val
            340                 345                 350

Arg Leu Lys His Arg Lys Leu Arg Glu Gln Val Asn Ser Met Val Asp
        355                 360                 365

Ile Ser Lys Met His Met Ile Leu Cys Asp Leu Gln Leu Gly Leu Ser
    370                 375                 380

Ser Ser His Arg Ala Leu Glu Lys Arg Ile Asp Gly Leu Ala Gly Lys
385                 390                 395                 400

Leu Asp Ala Leu Thr Glu Leu Leu Gly Thr Ala Leu Gln Gln Gln Gln
                405                 410                 415

Leu Pro Glu Pro Ser Gln Glu Ala Thr
            420                 425

<210> SEQ ID NO 5
<211> LENGTH: 1910
<212> TYPE: DNA
<213> ORGANISM: Rattus norvegicus
<220> FEATURE:
<221> NAME/KEY: CDS
<222> LOCATION: (143)...(1417)

<223> OTHER INFORMATION: Encodes rat potassium intermediate/small
      conductance calcium-activated channel, subfamily
      N, member 4 (KCNN4)
<300> PUBLICATION INFORMATION:
<308> DATABASE ACCESSION NUMBER: GenBank Accession No. NM_023021

<400> SEQUENCE: 5

```
ggctaggctg tgccttccag ccaaagtccc agggtgagca gaacaggccg ctggcctgga        60
agccaagctg gctgccattt gcgtactgag aggtggggga ccctgggcag gaagctggct       120
gagcaccaag agctcggggg cc atg ggc ggg gag ctg gtg act ggc ctg ggg       172
                         Met Gly Gly Glu Leu Val Thr Gly Leu Gly
                          1               5                   10 gcc ctg aga cgg aga aag cgc ctg ctg gag cag gag aag agg gtg gcc       220
Ala Leu Arg Arg Arg Lys Arg Leu Leu Glu Gln Glu Lys Arg Val Ala
                15                  20                  25 ggc tgg gca ctg gta ctg gcg gga act ggc atc gga ctc atg gtg ctg       268
Gly Trp Ala Leu Val Leu Ala Gly Thr Gly Ile Gly Leu Met Val Leu
            30                  35                  40 cac gct gag atg ttg tgg ttc ctg ggt tgc aag tgg gtg ctg tac ctg       316
His Ala Glu Met Leu Trp Phe Leu Gly Cys Lys Trp Val Leu Tyr Leu
        45                  50                  55 ctc ttg gtt aag tgt tta atc acg ctg tcc act gcc ttc ctc ctt tgt       364
Leu Leu Val Lys Cys Leu Ile Thr Leu Ser Thr Ala Phe Leu Leu Cys
    60                  65                  70 ctt att gtg gtc ttc cat gcc aag gag gtc cag ctg ttc atg act gac       412
Leu Ile Val Val Phe His Ala Lys Glu Val Gln Leu Phe Met Thr Asp
75                  80                  85                  90 aac ggg ctc cgg gac tgg cgc gtg gcg ctg acc cgg cgg cag gtg gcg       460
Asn Gly Leu Arg Asp Trp Arg Val Ala Leu Thr Arg Arg Gln Val Ala
                95                 100                 105 cag atc ctg ctg gag ctg ctg gta tgc ggg gtg cac ccg gtg ccc cta       508
Gln Ile Leu Leu Glu Leu Leu Val Cys Gly Val His Pro Val Pro Leu
            110                 115                 120 cgg agc ccg cac tgc acc ctg gcg ggg gag gcc aca gac tca cag gcc       556
Arg Ser Pro His Cys Thr Leu Ala Gly Glu Ala Thr Asp Ser Gln Ala
        125                 130                 135 tgg ccg ggc ttc ctg ggc gaa ggc gag gcg ttg ctg tcc ctg gcc atg       604
Trp Pro Gly Phe Leu Gly Glu Gly Glu Ala Leu Leu Ser Leu Ala Met
    140                 145                 150 ctg cta cgt ctc tac ctg gtg cct cgc gcg gta ctt ctg cgt agc ggg       652
Leu Leu Arg Leu Tyr Leu Val Pro Arg Ala Val Leu Leu Arg Ser Gly
155                 160                 165                 170 gtc ctg ctc aac gcg tct tac cgc agc atc ggg gcg ctc aac caa gtc       700
Val Leu Leu Asn Ala Ser Tyr Arg Ser Ile Gly Ala Leu Asn Gln Val
                175                 180                 185 cga ttc cgc cac tgg ttc gtg gcc aaa cta tac atg aac acg cac ccg       748
Arg Phe Arg His Trp Phe Val Ala Lys Leu Tyr Met Asn Thr His Pro
            190                 195                 200 ggt cgc ctg ctt ctg ggc ctc acg ctg ggc ctc tgg ctc acc aca gct       796
Gly Arg Leu Leu Leu Gly Leu Thr Leu Gly Leu Trp Leu Thr Thr Ala
        205                 210                 215 tgg gtg ctg tct gtg gct gag agg cag gct gtc aat gcc acg gga cac       844
Trp Val Leu Ser Val Ala Glu Arg Gln Ala Val Asn Ala Thr Gly His
    220                 225                 230 ctc aca gac aca ctg tgg ctg ata ccc atc acg ttc ctg acc att ggc       892
Leu Thr Asp Thr Leu Trp Leu Ile Pro Ile Thr Phe Leu Thr Ile Gly
235                 240                 245                 250 tat ggg gac gtc gta cct ggc acc cta tgg ggc aag att gtc tgc ttg       940
Tyr Gly Asp Val Val Pro Gly Thr Leu Trp Gly Lys Ile Val Cys Leu
                255                 260                 265
```

```
tgc acc gga gtc atg ggg gtc tgc tgc acg gct cta cta ttg gct gtg      988
Cys Thr Gly Val Met Gly Val Cys Cys Thr Ala Leu Leu Leu Ala Val
            270                 275                 280 gtg gcc cgg aag ctg gag ttc aac aag gcg gag aaa cac gtg cac aac     1036
Val Ala Arg Lys Leu Glu Phe Asn Lys Ala Glu Lys His Val His Asn
285                 290                 295 ttc atg atg gac atc cat tat gcc aaa gag atg aag gag tcg gcc gct     1084
Phe Met Met Asp Ile His Tyr Ala Lys Glu Met Lys Glu Ser Ala Ala
    300                 305                 310 cgg ctg ctg cag gaa gcc tgg atg tac tac aaa cac act cga agg aag     1132
Arg Leu Leu Gln Glu Ala Trp Met Tyr Tyr Lys His Thr Arg Arg Lys
315                 320                 325                 330 gac tcc cga gcg gct cgc agg cat cag cgc aag atg ctg gct gcc atc     1180
Asp Ser Arg Ala Ala Arg Arg His Gln Arg Lys Met Leu Ala Ala Ile
                335                 340                 345 cac acg ttc cgc cag gta cgg ctg aaa cat cgg aag ctc cgg gaa caa     1228
His Thr Phe Arg Gln Val Arg Leu Lys His Arg Lys Leu Arg Glu Gln
            350                 355                 360 gtg aat tcc atg gtg gac atc tcc aag atg cac atg atc ctg tgc gac     1276
Val Asn Ser Met Val Asp Ile Ser Lys Met His Met Ile Leu Cys Asp
365                 370                 375 ctg cag ctc ggg ctc agc gcc tcg cac ctt gcc ctg gag aag aga atc     1324
Leu Gln Leu Gly Leu Ser Ala Ser His Leu Ala Leu Glu Lys Arg Ile
    380                 385                 390 cat ggg ctg gca agg aag ctg gat gcc ctg act gaa ctg ctc agt tct     1372
His Gly Leu Ala Arg Lys Leu Asp Ala Leu Thr Glu Leu Leu Ser Ser
395                 400                 405                 410 gcc ctg cag cag cag ccg cca gaa ccc atc cag gag gcc aca tag         1417
Ala Leu Gln Gln Gln Pro Pro Glu Pro Ile Gln Glu Ala Thr
                415                 420 ctgcctgtta tcgatctaca ttctactcag gacccacaga agaatcaggc tatgtaccga   1477
aggactgagc tcaaggacat cctccctgcc tattctgacc aagccccatg aataaatcac   1537
ctcaagatgc caggacacaa gtggatccac gttgagatgc atggactctg gtggtggcag   1597
ccatgagtgg acactggctt ggacctccca tggcagtggg gttactatgg tcaccactac   1657
acataggcca tcatcaaaag tcctttctgc tgtgctgctg ctgttcatga ccctcaagc    1717 tctgttggaa gaggaggtgc cgggggtcca agatgctagg aagaagcttc agtcaccgca   1777
ggccggcctc gctgaaggaa ccaggtccga gcggcgggag gtgctgcccc ctggtggacg   1837
ctgcttcccc cagaatgcgg aaactgcgcg ggagtaaggt gcggggtgcc gctcaccaat   1897
ccacgaattc cac                                                     1910

<210> SEQ ID NO 6
<211> LENGTH: 424
<212> TYPE: PRT
<213> ORGANISM: Rattus norvegicus

<400> SEQUENCE: 6

Met Gly Gly Glu Leu Val Thr Gly Leu Gly Ala Leu Arg Arg Arg Lys
1               5                   10                  15

Arg Leu Leu Glu Gln Glu Lys Arg Val Ala Gly Trp Ala Leu Val Leu
            20                  25                  30

Ala Gly Thr Gly Ile Gly Leu Met Val Leu His Ala Glu Met Leu Trp
        35                  40                  45

Phe Leu Gly Cys Lys Trp Val Leu Tyr Leu Leu Leu Val Lys Cys Leu
    50                  55                  60
```

-continued

```
Ile Thr Leu Ser Thr Ala Phe Leu Leu Cys Leu Ile Val Val Phe His
 65                  70                  75                  80

Ala Lys Glu Val Gln Leu Phe Met Thr Asp Asn Gly Leu Arg Asp Trp
                 85                  90                  95

Arg Val Ala Leu Thr Arg Arg Gln Val Ala Gln Ile Leu Leu Glu Leu
            100                 105                 110

Leu Val Cys Gly Val His Pro Val Pro Leu Arg Ser Pro His Cys Thr
        115                 120                 125

Leu Ala Gly Glu Ala Thr Asp Ser Gln Ala Trp Pro Gly Phe Leu Gly
    130                 135                 140

Glu Gly Glu Ala Leu Leu Ser Leu Ala Met Leu Leu Arg Leu Tyr Leu
145                 150                 155                 160

Val Pro Arg Ala Val Leu Leu Arg Ser Gly Val Leu Leu Asn Ala Ser
                165                 170                 175

Tyr Arg Ser Ile Gly Ala Leu Asn Gln Val Arg Phe Arg His Trp Phe
            180                 185                 190

Val Ala Lys Leu Tyr Met Asn Thr His Pro Gly Arg Leu Leu Leu Gly
        195                 200                 205

Leu Thr Leu Gly Leu Trp Leu Thr Thr Ala Trp Val Leu Ser Val Ala
    210                 215                 220

Glu Arg Gln Ala Val Asn Ala Thr Gly His Leu Thr Asp Thr Leu Trp
225                 230                 235                 240

Leu Ile Pro Ile Thr Phe Leu Thr Ile Gly Tyr Gly Asp Val Val Pro
                245                 250                 255

Gly Thr Leu Trp Gly Lys Ile Val Cys Leu Cys Thr Gly Val Met Gly
            260                 265                 270

Val Cys Cys Thr Ala Leu Leu Leu Ala Val Val Ala Arg Lys Leu Glu
        275                 280                 285

Phe Asn Lys Ala Glu Lys His Val His Asn Phe Met Met Asp Ile His
    290                 295                 300

Tyr Ala Lys Glu Met Lys Glu Ser Ala Ala Arg Leu Leu Gln Glu Ala
305                 310                 315                 320

Trp Met Tyr Tyr Lys His Thr Arg Arg Lys Asp Ser Arg Ala Ala Arg
                325                 330                 335

Arg His Gln Arg Lys Met Leu Ala Ala Ile His Thr Phe Arg Gln Val
            340                 345                 350

Arg Leu Lys His Arg Lys Leu Arg Glu Gln Val Asn Ser Met Val Asp
        355                 360                 365

Ile Ser Lys Met His Met Ile Leu Cys Asp Leu Gln Leu Gly Leu Ser
    370                 375                 380

Ala Ser His Leu Ala Leu Glu Lys Arg Ile His Gly Leu Ala Arg Lys
385                 390                 395                 400

Leu Asp Ala Leu Thr Glu Leu Leu Ser Ser Ala Leu Gln Gln Gln Pro
                405                 410                 415

Pro Glu Pro Ile Gln Glu Ala Thr
            420

<210> SEQ ID NO 7
<211> LENGTH: 9
<212> TYPE: PRT
<213> ORGANISM: Artificial Sequence
<220> FEATURE:
<223> OTHER INFORMATION: tyrosine phosphorylation consensus sequence

<400> SEQUENCE: 7
```

Arg Leu Leu Gln Glu Ala Trp Met Tyr
 1               5

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gctcaaccaa gtccgcttcc                                        20

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
caatggtcag gaatgtgatc g                                      21

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ggaactggca tcggactcat                                        20

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
ctggacctcc ttggcatgga a                                      21

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
aatgtgtccg tcgtggatct                                        20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ccctgttgct gtagccgtat                                        20

COMPOSITIONS AND METHODS FOR MODULATING CELL-CELL FUSION VIA INTERMEDIATE-CONDUCTANCE CALCIUM-ACTIVATED POTASSIUM CHANNELS

FIELD OF THE INVENTION

The invention relates generally to compositions and methods for modulating cell-cell fusion (also called cellocytosis), and more particularly to compositions and methods for modulating homotypic and heterotypic cell-cell fusion of macrophages. The invention thus provides compositions and methods for modulating cell fusion, and osteoclast differentiation and function linked to various diseases or disorders.

BACKGROUND

Cell fusion is a fundamental biological event that is essential for a variety of developmental and homeostatic processes. Although intracellular membrane fusion during organelle trafficking is well understood, less is known about cell-cell fusion mediating sperm-oocyte, myoblast-myoblast, and macrophage-macrophage fusion. See, Vignery (2000) *Int. J. Exp. Pathol.* 81:291-304.

With respect to macrophages, these cells can fuse with themselves (i.e., homotypic fusion) in tissue to form giant cells, which are involved in chronic inflammatory diseases. See, MacLauchlan et al. (2009) *J. Leukoc. Biol.* 85:617-626; and Vignery (2000), supra. In addition, macrophages can fuse with themselves in bone to form osteoclasts, which mediate bone resorption. More recently, it is believed that macrophages can fuse with somatic or cancer cells (i.e., heterotypic fusion). See, Vignery (2005) *Trends Cell Biol.* 15:188-193.

Unfortunately, the mechanism(s) by which macrophages fuse with themselves and other cells remain largely uncharacterized. See, MacLauchlan et al. (2009), supra; and Vignery (2005), supra. Understanding this process can help to modulate macrophage function and also limit the damage caused in inflammatory and infectious diseases when these cells fuse in an inappropriate or unregulated manner. For the foregoing reasons, there is a need for compositions and methods for inhibiting macrophage fusion.

Osteoclasts are formed by the fusion of cells of the monocyte-macrophage cell line. An osteoclast is a large cell that is characterized by multiple nuclei and a high concentration of vesicles and vacuoles. Osteoclasts form a specialized cell membrane at a site of active bone resorption which facilitates removal of the bony matrix. Such mechanism results in osteoporosis or osteopenia (having a bone mineral density that is lower than normal but not low enough to be classified as osteoporosis). Rheumatoid arthritis is often complicated by generalized osteopenia due to increased bone resorption by osteoclasts. Thus, there is also a need for compositions and methods for modulating, particularly inhibiting, osteoclast differentiation and function.

BRIEF SUMMARY

The present invention broadly relates to compositions and methods for modulating cell-cell fusion by using agents that modulate expression, activity, or function of intermediate-conductance calcium-activated potassium channel (SK4 channel or IK channel or KCNN4 channel or KCa3.1 channel or IKCa1 channel). Compositions of the invention comprise an effective amount of an SK4 channel modulator (inhibitor or activator) alone or in combination with other therapeutic agents. In one embodiment, methods of the invention comprise providing an effective amount of an SK4 channel inhibitor to cells having the potential to fuse or to actively fusing cells. Optionally, the methods comprise co-providing a therapeutic agent along with the SK4 channel inhibitor. Also included are methods to identify SK4 channel inhibitors capable of inhibiting cell-cell fusion.

In another embodiment, the invention is drawn to activating cell-cell fusion. In this manner, methods comprise providing an effective amount of an SK4 channel activator to cells having the potential to fuse or to actively fusing cells. Also included are methods to identify SK4 channel activators capable of promoting cell-cell fusion.

In some embodiments, the compositions and methods of the invention provide for modulation of macrophage cell fusion. In other embodiments, the compositions and methods provide for modulation of osteoclast differentiation and function, including inhibition thereof.

The compositions and methods of the invention find use in preventing or treating diseases or disorders mediated by macrophage-derived multinucleate cells, including diseases associated with osteoclasts, giant cells or metastatic cancer cells.

The following embodiments are encompassed by the present invention.

1. A method for modulating cell fusion of a cell expressing an intermediate-conductance calcium-activated potassium (SK4) channel, the method comprising the step of contacting the cell with an effective amount of an SK4 channel inhibitor or activator, wherein cell fusion is modulated.

2. The method of embodiment 1, wherein cell fusion is inhibited.

3. The method of embodiment 1, wherein the cell is a hematopoietic cell.

4. The method of embodiment 1, wherein the cell is selected from the group consisting of a macrophage, dendritic cell, and B-cell.

5. The method of embodiment 1, wherein the cell is a macrophage.

6. The method of embodiment 1, wherein the cell fusion is homotypic or heterotypic.

7. The method of embodiment 1, wherein the SK4 channel inhibitor is selected from the group consisting of an inhibitory nucleic acid, monoclonal antibody, and small molecule inhibitor.

8. The method of embodiment 7, wherein said inhibitory nucleic acid targets expression of an SK4 channel comprising the sequence set forth in SEQ ID NO:2.

9. The method of embodiment 7, wherein the monoclonal antibody recognizes a pore region or small molecule-binding domain of an SK4 channel.

10. The method of embodiment 7, wherein the small molecule inhibitor is selected from the group consisting of 1-[(2-chlorophenyl)-diphenylmethyl]-1H-imidazole; 2,2-bis(4-fluorophenyl)-2-phenylacetamide; 1-[(2-chlorophenyl)diphenylmethyl]-1H-pyrazole; 1-[(2-fluorophenyl)diphenylmethyl]-1H-pyrazole; 1-[(4-chlorophenyl)diphenylmethyl]-1H-pyrazole; 1-[(2-fluorophenyl)diphenylmethyl]-1H-pyrazole; and 1-[(2-chlorophenyl)diphenylmethyl]-1H-tetrazole.

11. The method of embodiment 7, wherein the small molecule inhibitor is 1-[(2-chlorophenyl)-diphenylmethyl]-1H-imidazole.

12. The method of embodiment 7, wherein the small molecule inhibitor is 2,2-bis(4-fluorophenyl)-2-phenylacetamide.

13. The method of embodiment 7, wherein the small molecule inhibitor is 1-[(2-chlorophenyl)diphenylmethyl]-1H-pyrazole.

14. The method of embodiment 7, further comprising the step of assaying for SK4 channel expression or activity in the cell.

15. The method of embodiment 1, wherein the method is an in vivo method, and wherein the effective amount of the SK4 channel inhibitor is a therapeutically effective amount provided to a subject having or suspected of having abnormal cell fusion.

16. The method of embodiment 15, further comprising co-providing to the subject a therapeutically effective amount of an anti-inflammatory agent, anti-bone-loss agent, immunosuppressive agent, or chemotherapeutic agent.

17. A method for modulating osteoclast differentiation and function, the method comprising the step of contacting an osteoclast or an osteoclast precursor with an effective amount of an intermediate-conductance potassium-activated potassium (SK4) channel inhibitor or activator.

18. The method of embodiment 17, wherein osteoclast formation is inhibited.

19. The method of embodiment 17, wherein the SK4 channel inhibitor is selected from the group consisting of an inhibitory nucleic acid, monoclonal antibody, and small molecule inhibitor.

20. The method of embodiment 19, wherein the monoclonal antibody recognizes a pore region or small molecule-binding domain of an SK4 channel.

21. The method of embodiment 19, wherein the small molecule inhibitor is selected from the group consisting of 1-[(2-chlorophenyl)-diphenylmethyl]-1H-imidazole; 2,2-bis(4-fluorophenyl)-2-phenylacetamide; 1-[(2-chlorophenyl)diphenylmethyl]-1H-pyrazole; 1-[(2-fluorophenyl)diphenylmethyl]-1H-pyrazole; 1-[(4-chlorophenyl)diphenylmethyl]-1H-pyrazole; 1-[(2-fluorophenyl)diphenylmethyl]-1H-pyrazole; and 1-[(2-chlorophenyl)diphenylmethyl]-1H-tetrazole.

22. The method of embodiment 19, wherein the small molecule inhibitor is 1-[(2-chlorophenyl)-diphenylmethyl]-1H-imidazole.

23. The method of embodiment 19, wherein the small molecule inhibitor is 2,2-bis(4-fluorophenyl)-2-phenylacetamide.

24. The method of embodiment 19, wherein the small molecule inhibitor is 1-[(2-chlorophenyl)diphenylmethyl]-1H-pyrazole.

25. The method of embodiment 17, wherein the method is an in vivo method, and wherein the effective amount of the SK4 channel inhibitor is a therapeutically effective amount provided to a subject having or suspected of having abnormal osteoclast differentiation or function.

26. The method of embodiment 25, further comprising co-administering to the subject a therapeutically effective amount of an anti-inflammatory agent, anti-bone-loss agent, immunosuppressive agent, or chemotherapeutic agent.

27. A method for preventing or treating bone loss in a subject susceptible to or having bone loss, the method comprising the step of administering to the subject a therapeutically effective amount of an intermediate-conductance calcium-activated potassium (SK4) channel inhibitor to inhibit osteoclast formation, wherein bone loss is prevented or decreased in the subject.

28. The method of embodiment 27, wherein the SK4 channel inhibitor is selected from the group consisting of an inhibitory nucleic acid, monoclonal antibody, and small molecule inhibitor.

29. The method of embodiment 28, wherein the monoclonal antibody recognizes a pore region, or a small molecule-binding domain of an SK4 channel.

30. The method of embodiment 28, wherein the small molecule inhibitor is selected from the group consisting of 1-[(2-chlorophenyl)-diphenylmethyl]-1H-imidazole; 2,2-bis(4-fluorophenyl)-2-phenylacetamide; 1-[(2-chlorophenyl)diphenylmethyl]-1H-pyrazole; 1-[(2-fluorophenyl)diphenylmethyl]-1H-pyrazole; 1-[(4-chlorophenyl)diphenylmethyl]-1H-pyrazole; 1-[(2-fluorophenyl)diphenylmethyl]-1H-pyrazole; and 1-[(2-chlorophenyl)diphenylmethyl]-1H-tetrazole.

31. The method of embodiment 28, wherein the small molecule inhibitor is 1-[(2-chlorophenyl)-diphenylmethyl]-1H-imidazole.

32. The method of embodiment 28, wherein the small molecule inhibitor is 2,2-bis(4-fluorophenyl)-2-phenylacetamide.

33. The method of embodiment 28, wherein the small molecule inhibitor is 1-[(2-chlorophenyl)diphenylmethyl]-1H-pyrazole.

34. The method of embodiment 27, further comprising co-administering to the subject a therapeutically effective amount of an anti-inflammatory agent, anti-bone-loss agent, immunosuppressive agent or chemotherapeutic agent.

35. A method for preventing or treating an inflammatory or autoimmune disease characterized by giant cell formation in a subject susceptible to or having the inflammatory or autoimmune disease, the method comprising the step of administering to the subject a therapeutically effective amount of an intermediate-conductance calcium-activated potassium (SK4) channel inhibitor to inhibit giant cell formation, wherein the inflammatory or autoimmune disease is prevented or treated in the subject.

36. The method of embodiment 35, wherein the SK4 channel inhibitor is selected from the group consisting of an inhibitory nucleic acid, monoclonal antibody, and small molecule inhibitor.

37. The method of embodiment 36, wherein the monoclonal antibody recognizes a pore region or small molecule-binding domain of an SK4 channel.

38. The method of embodiment 36, wherein the small molecule inhibitor is selected from the group consisting of 1-[(2-chlorophenyl)-diphenylmethyl]-1H-imidazole; 2,2-bis(4-fluorophenyl)-2-phenylacetamide; 1-[(2-chlorophenyl)diphenylmethyl]-1H-pyrazole; 1-[(2-fluorophenyl)diphenylmethyl]-1H-pyrazole; 1-[(4-chlorophenyl)diphenylmethyl]-1H-pyrazole; 1-[(2-fluorophenyl)diphenylmethyl]-1H-pyrazole; and 1-[(2-chlorophenyl)diphenylmethyl]-1H-tetrazole.

39. The method of embodiment 36, wherein the small molecule inhibitor is 1-[(2-chlorophenyl)-diphenylmethyl]-1H-imidazole.

40. The method of embodiment 36, wherein the small molecule inhibitor is 2,2-bis(4-fluorophenyl)-2-phenylacetamide.

41. The method of embodiment 36, wherein the small molecule inhibitor is 1-[(2-chlorophenyl)diphenylmethyl]-1H-pyrazole.

42. The method of embodiment 35, further comprising co-administering to the subject a therapeutically effective amount of an anti-inflammatory agent, anti-bone-loss agent, immunosuppressive agent, or chemotherapeutic agent.

43. A method for preventing implant or transplant rejection in a subject having an implant or a transplant at a site located within the subject, the method comprising the step of administering to the subject a therapeutically effective amount of an intermediate-conductance calcium-activated potassium (K) channel inhibitor to inhibit giant cell formation at or in the vicinity of the site, wherein rejection of the implant or transplant is prevented in the subject.

44. The method of embodiment 43, wherein the SK4 channel inhibitor is selected from the group consisting of an inhibitory nucleic acid, monoclonal antibody, and small molecule inhibitor.

45. The method of embodiment 44, wherein the monoclonal antibody recognizes a pore region or small molecule-binding domain of an SK4 channel.

46. The method of embodiment 44, wherein the small molecule inhibitor is selected from the group consisting of 1-[(2-chlorophenyl)-diphenylmethyl]-1H-imidazole; 2,2-bis (4-fluorophenyl)-2-phenylacetamide; 1-[(2-chlorophenyl) diphenylmethyl]-1H-pyrazole; 1-[(2-fluorophenyl)diphenylmethyl]-1H-pyrazole; 1-[(4-chlorophenyl)diphenylmethyl]-1H-pyrazole; 1-[(2-fluorophenyl)diphenylmethyl]-1H-pyrazole; and 1-[(2-chlorophenyl)diphenylmethyl]-1H-tetrazole.

47. The method of embodiment 44, wherein the small molecule inhibitor is 1-[(2-chlorophenyl)-diphenylmethyl]-1H-imidazole.

48. The method of embodiment 44, wherein the small molecule inhibitor is 2,2-bis(4-fluorophenyl)-2-phenylacetamide.

49. The method of embodiment 44, wherein the small molecule inhibitor is 1-[(2-chlorophenyl)diphenylmethyl]-1H-pyrazole.

50. The method of embodiment 43, further comprising co-administering to the subject a therapeutically effective amount of an anti-inflammatory agent, or an immunosuppressive agent.

51. The method of embodiment 43, wherein the transplant is a cell, organ, or tissue transplant.

52. A method to prevent cancer metastasis in a subject having cancer, the method comprising the step of administering to the subject a therapeutically effective amount of an intermediate-conductance calcium-activated potassium (SK4) channel inhibitor to inhibit metastatic cancer cell formation, wherein the cancer metastasis is prevented in the subject.

53. The method of embodiment 52, wherein the SK4 channel inhibitor is selected from the group consisting of an inhibitory nucleic acid, monoclonal antibody, and small molecule inhibitor.

54. The method of embodiment 53, wherein the monoclonal antibody recognizes a pore region or small molecule binding domain of an SK4 channel.

55. The method of embodiment 53, wherein the small molecule inhibitor is selected from the group consisting of 1-[(2-chlorophenyl)-diphenylmethyl]-1H-imidazole; 2,2-bis (4-fluorophenyl)-2-phenylacetamide; 1-[(2-chlorophenyl) diphenylmethyl]-1H-pyrazole; 1-[(2-fluorophenyl)diphenylmethyl]-1H-pyrazole; 1-[(4-chlorophenyl)diphenylmethyl]-1H-pyrazole; 1-[(2-fluorophenyl)diphenylmethyl]-1H-pyrazole; and 1-[(2-chlorophenyl)diphenylmethyl]-1H-tetrazole.

56. The method of embodiment 53, wherein the small molecule inhibitor is 1-[(2-chlorophenyl)-diphenylmethyl]-1H-imidazole.

57. The method of embodiment 53, wherein the small molecule inhibitor is 2,2-bis(4-fluorophenyl)-2-phenylacetamide.

58. The method of embodiment 53, wherein the small molecule inhibitor is 1-[(2-chlorophenyl)diphenylmethyl]-1H-pyrazole.

59. The method of embodiment 52, further comprising co-administering to the subject a therapeutically effective amount of an anti-inflammatory agent, anti-bone-loss agent, immunosuppressive agent or chemotherapeutic agent.

60. A method to identify an intermediate-conductance calcium-activated potassium (SK4) channel inhibitor that inhibits cell-cell fusion, the method comprising the steps of:
  contacting a cell population with a candidate SK4 channel inhibitor; and
  determining whether the candidate agent inhibits cell-cell fusion within the cell population.

61. The method of embodiment 60, wherein the cell population comprises macrophages and the SK4 channel inhibitor inhibits cell-cell fusion of macrophages.

62. The method of embodiment 60, wherein the cell population comprises at least two cell types, one of which is macrophages.

63. A composition comprising:
  an effective amount of an intermediate-conductance calcium-activated potassium (SK4) channel inhibitor; and
  a therapeutic, wherein the therapeutic agent is selected from the group consisting of an anti-inflammatory agent, anti-bone-loss agent, immunosuppressive agent and chemotherapeutic agent.

64. The composition of embodiment 63, wherein the SK4 channel inhibitor is selected from the group consisting of an inhibitory nucleic acid, monoclonal antibody, and small molecule inhibitor.

65. The composition of embodiment 64, wherein the monoclonal antibody recognizes a pore region or small molecule-binding domain of an SK4 channel.

66. The composition of embodiment 64, wherein the small molecule inhibitor is selected from the group consisting of 1-[(2-chlorophenyl)-diphenylmethyl]-1H-imidazole; 2,2-bis (4-fluorophenyl)-2-phenylacetamide; 1-[(2-chlorophenyl) diphenylmethyl]-1H-pyrazole; 1-[(2-fluorophenyl)diphenylmethyl]-1H-pyrazole; 1-[(4-chlorophenyl)diphenylmethyl]-1H-pyrazole; 1-[(2-fluorophenyl)diphenylmethyl]-1H-pyrazole; and 1-[(2-chlorophenyl)diphenylmethyl]-1H-tetrazole.

67. The composition of embodiment 64, wherein the small molecule inhibitor is 1-[(2-chlorophenyl)-diphenylmethyl]-1H-imidazole.

68. The composition of embodiment 64, wherein the small molecule inhibitor is 2,2-bis(4-fluorophenyl)-2-phenylacetamide.

69. The composition of embodiment 64, wherein the small molecule inhibitor is 1-[(2-chlorophenyl)diphenylmethyl]-1H-pyrazole.

70. The composition of embodiment 63, further comprising a pharmaceutically acceptable carrier.

71. A method to identify an intermediate-conductance calcium-activated potassium (SK4) channel activator that activates cell-cell fusion, the method comprising the steps of:
  contacting a cell population with a candidate SK4 channel activator; and
  determining whether the candidate agent activates cell-cell fusion within the cell population.

72. The method of embodiment 71, wherein the cell population comprises macrophages and the SK4 channel activator activates cell-cell fusion of macrophages.

73. The method of embodiment 71, wherein the cell population comprises at least two cell types, one of which is macrophages.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIGS. 8A-B show significantly attenuated arthritis scores from homozygous knockout (sk4$^{-/-}$) mice (male (M) and female (F) compared to WT mice (M and F) in an anti-collagen antibody-induced arthritis model. Data from two separate experiments are shown. The number of animals in each study group is indicated in FIGS. 8A-B, and the error bars represent standard error of the mean.

FIG. 14 shows that absence of SK4 dramatically prevents bone resorption in response to local subcutaneous injection of LPS above the calvarium. Eight-week-old sk4$^{+/+}$ and sk4$^{-/-}$ male and female mice were injected with 25 μg of LPS, in a 2 μl volume, in the periosteum of the right calvarium (see FIG. 13). Heads were subjected to scanning by microCT. Note the lack of response of SK4-deficient mice to LPS. (n=5).

DETAILED DESCRIPTION

Figure 1A:
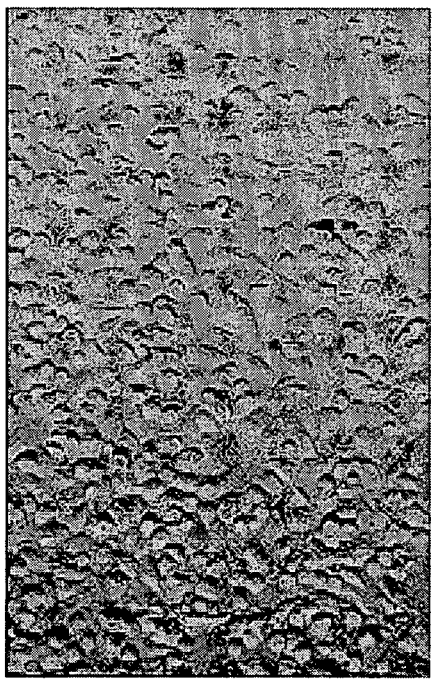
FIG. 1A shows a photograph of freshly plated rat alveolar macrophages.

The present invention relates to an identification of increased intermediate-conductance calcium-activated potassium (SK4 or KCNN4 or IK) channel expression during cell-cell fusion, especially during homotypic and heterotypic fusions involving macrophages. The invention comprises the use of SK4 inhibitors or activators to modulate cell-cell fusion. That is, compositions and methods are provided for modulating cell-cell fusion via the modulation of SK4 channel expression, activity or function. In this manner, SK4 channel expression, activity or function can be decreased (i.e., inhibited) or increased in order to decrease (i.e., inhibit) or increase cell-cell fusion, respectively. Of particular interest is the modulation of cell-cell fusion involving macrophages.

For example, the fusion of cells such as macrophages can lead to formation of multinucleate osteoclasts that are involved in the development, remodeling and repair of bone. Dysfunctional osteoclast activity can be a cause of bone diseases such osteoporosis and rheumatoid arthritis. Likewise, fusion of macrophages can lead to formation of multinucleate giant cells that form in response to a foreign body such as a pathogen or an implant. The present invention therefore focuses on the role of SK4 channels in macrophage fusion.

In some embodiments, the present invention provides methods for inhibiting cell-cell fusion, more particularly cell-cell fusion involving macrophages. In such embodiments, SK4 channel expression, activity or function, and thus cell-cell fusion, can be decreased (i.e., inhibited), for example, by contacting cells of interest with an effective amount of an SK4 channel inhibitor. In this manner, SK4 channel expression, activity or function can be decreased in those cells of interest by a statistically significant amount including, but not limited to, 5%, 10%, 15%, 20%, 25%, 30%, 35%, 40%, 45%, 50%, 55%, 60%, 65%, 70%, 75%, 80%, 85%, 90%, 95% or 100% when compared to an appropriate control.

In other embodiments, it may be desirable to have increased cell-cell fusion, for example, increased macrophage cell fusion. Thus, for example, increased macrophage cell fusion and formation of multinucleate osteoclasts may be desirable to counter abnormally increased bone density, or to treat a chronic infection or osteopetrosis. In such embodiments, SK4 channel expression, activity or function of macrophage cells can be increased, for example, by contacting macrophage cells with an effective amount of an activator of SK4 channel expression, activity or function. Where the desired outcome is an increase in cell-cell fusion, SK4 channel expression, activity or function can be increased in those cells of interest by a statistically significant amount including, but not limited to, 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150% or more when compared to an appropriate control.

The compositions and methods of the invention find use in modulating osteoclast differentiation and function via modulation of SK channel expression, activity or function of osteoclasts and/or osteoclast precursors. Osteoclasts are homotypic, specialized, multinucleated, macrophage-derived cells that solubilize bone tissue by removing its mineralized matrix. By modulating osteoclastogenesis from osteoclast precursors such as macrophage cells it is possible to alter osteoclast formation and thus osteoclast number and/or osteoclast surface area, thereby altering overall osteoclast function. Osteoclast function can be modulated to alter, for example, the bone mineral resorption activity of these cells. Thus, in some embodiments, the present invention provides a method for modulating osteoclast differentiation and function, where the method comprises contacting an osteoclast and/or an osteoclast precursor with an effective amount of an SK4 channel inhibitor or activator.

In some embodiments, osteoclast differentiation and/or function are inhibited using an SK channel inhibitor. Thus, where the desired outcome is a decrease in osteoclast differentiation and/or function, SK4 channel expression, activity or function of osteoclast precursors such as macrophages can be inhibited to decrease macrophage cell fusion, thereby decreasing osteoclast formation (including decreasing osteoclast number and/or osteoclast cell surface area), which results in an overall decrease in osteoclast function. SK4 channel expression, activity or function of osteoclasts can be inhibited, thereby decreasing osteoclast function, including, for example, decreasing osteoclast bone mineral resorption activity. SK4 channel expression, activity or function can be decreased in osteoclasts and/or osteoclast precursors by a statistically significant amount including, but not limited to, 5%, 10%, 15%, 20%, 25%, 30%, 35%, 40%, 45%, 50%, 55%, 60%, 65%, 70%, 75%, 80%, 85%, 90%, 95% or 100% when compared to an appropriate control.

In other embodiments of the invention, the methods provide for increased osteoclast differentiation and/or function using an SK channel activator. Thus, for example, increased osteoclast differentiation and/or functioin may be desirable to counter abnormally increased bone density, or to treat a chronic infection or osteopetrosis. Thus, where the desired outcome is an increase in osteoclast differentiation and/or function, SK4 channel expression, activity or function of osteoclast precursors such as macrophages can be increased to increase macrophage cell fusion, thereby increasing osteoclast formation (including increasing osteoclast number and/or osteoclast cell surface area), which results in an overall increase in osteoclast function, including, for example, an increase in osteoclast bone mineral resorption activity. SK4 channel expression, activity or function of osteoclasts can be increased, thereby increasing osteoclast function, for example, increasing osteoclast bone mineral resorption activity. SK4 channel expression, activity or function can be increased in osteoclasts and/or osteoclast precursors by a statistically significant amount including, but not limited to, 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150% or more when compared to an appropriate control.

Inhibition of Cell-Cell Fusion

While not intending to be bound to any particular theory, SK4 channel inhibitors modulate SK4 channel expression, SK4 channel activity, or upstream or downstream SK4 channel effectors of actively fusing cells and/or newly fused multinucleate cells such as osteoclasts, giant cells or metastatic cancer cells. As such, compositions and methods are described for inhibiting cell-cell fusion with SK4 channel inhibitors, more particularly for inhibiting macrophage cell fusion, including homotypic and heterotypic fusions resulting in formation of osteoclasts, giant cells and metastatic cancer cells.

SK4 channel inhibitors therefore can be provided in vivo or in vitro to inhibit cell-cell fusion. When provided in vitro, the SK4 channel inhibitors can be used to inhibit cell-cell fusion or to screen for agents that modulate cell-cell fusion. When provided in vivo, the SK4 channel inhibitors can be used to prevent and/or treat a variety of diseases or disorders where macrophage-derived multinucleate cells, particularly osteoclasts, giant cells or metastatic cancer cells, are implicated. In particular, the SK4 channel inhibitors can be used to prevent or reduce bone resorption/bone loss, to prevent or treat an autoimmune or inflammatory disease or disorder, to prevent implant or transplant rejection, or to prevent cancer metastasis.

As used herein, "intermediate-conductance calcium-activated potassium channel," "intermediate-conductance calcium-activated potassium channels," "SK4 channel," or "SK4 channels" means voltage-independent, inwardly rectifying, potassium channels that have a conductance of less than 100 pS or between about 12 pS to about 50 pS (see, e.g., Christopherson (1991) *J. Membr. Biol.* 119:75-83; and Tharp &

Bowles (2009) *Cardiovasc. Hematological Agents Med. Chem.* 7:1-11; each of which is incorporated herein by reference as if set forth in its entirety), but typically between about 30 pS to about 40 pS. SK4 channels are activated by submicromolar intracellular calcium concentrations (about 100 nmol/L to about 300 nmol/L) and are blocked by charybdotoxin and triarylmethanes such as clotrimazole, TRAM-34 and ICA-15451, but are not blocked by iberiotoxin, apamin, or ketoconazole. SK4 channels are variously known in the art as intermediate conductance calcium-activated potassium channel protein 4, Gardos, fIK, hIK, mIK, IK, IK1, IKCa1, IKCA1, ImK, KCa4, KCA4, KCa3.1, KCNN4, or SK4 channels. See, e.g., Cho et al. (2008) *Expert Rev. Mol. Diagn.* 8:179-187; and Reich et al. (2005) *Eur. J. Immunol.* 35:1027-1036; each of which is incorporated herein by reference as if set forth in its entirety. Thus, for purposes of the present invention the term "SK4 channel" is intended to encompass the various names by which these channels are known, including KCNN4 and SK4 channels.

The nucleic and amino acid sequences for SK4 channel monomers are known for many species such as mice, rats, and humans. See, e.g., Joiner et al. (1997) *Proc. Natl. Acad. Sci. USA* 94:11013-11018; Logsdon et al. (1997) *J. Biol. Chem.* 272:32723-32726; Neylon et al. (1999) *Circ. Res.* 85:E33-E43; Vandorpe et al. (1998) *J. Biol. Chem.* 273:21542-21553; Warth et al. (1999) *Pflugers Arch.* 438:437-444; and U.S. Pat. Nos. 6,692,937 and 6,894,147; each of which is incorporated herein by reference as if set forth in its entirety; see also, SEQ ID NOS:1-6. SK4 channel monomers have six transmembrane segments (S1-S6) and a pore motif between S5 and S6 that contains a potassium-selective amino acid sequence GYG. SK4 channel monomers also have an N-linked glycosylation site near the pore motif.

The N-terminus of SK4 channels contains an endoplasmic retention signal (Tharp & Bowles (2009), supra), and the C-terminus contains a calmodulin-binding domain that senses intracellular calcium (Fanger et al. (1999) *J. Biol. Chem.* 274:5746-5754; and Joiner et al. (2001) *J. Biol. Chem.* 276:37980-37985; each of which is incorporated herein by reference as if set forth in its entirety). The C-terminus also contains numerous consensus sequences for protein kinase A (PKA), protein kinase C (PKC), and protein kinase G (PKG) phosphorylation (Joiner et al. (1997), supra), as well as a consensus sequence for tyrosine phosphorylation (RLLQEAWMY; SEQ ID NO:7; Tharp & Bowles (2009), supra). SK4 channel monomers form homotetramers to regulate potassium ion efflux.

SK4 channels are expressed in many cell types including T-cells, B-cells, macrophages, microglial cells, red blood cells, smooth muscle cells, endothelial cells and epithelial cells, but the timing of expression and role of the channels can vary in these cells. The expression and role of SK4 channels in fusing or recently fused cells, however, has not been previously reported.

As used herein, "macrophage" or "macrophages" means CD68$^+$ (humans) or F4/80$^+$ (mouse) mononuclear leukocytes that function in tissue homeostasis as well as in innate and acquired immunity. Macrophages also can be CD11b$^+$. Morphologically, they appear as large cells (~25 μm to 50 μm) with a round nucleus and containing one to two nucleoli, clumped chromatin, abundant cytoplasm with vacuoles and numerous azurophilic granules. Macrophages are located throughout a body's tissues and are derived from circulating monocytes (i.e., blood-borne mononuclear leukocytes). They have two principal roles: phagocytosis and antigen presentation.

As phagocytic cells, macrophages engulf and then digest cellular debris and pathogens (e.g., bacteria, fungi, protozoa, viruses and yeasts) and stimulate lymphocytes and other immune cells to respond to these pathogens. As antigen-presenting cells, macrophages process and present antigens from phagocytized pathogens on their surface for lymphocytes and other immune cells. Macrophages also secrete an array of monokines including enzymes, complement proteins and regulatory factors such as interleukin-1 and tumor necrosis factor-α. In addition, macrophages have receptors for lymphokines, which activate them into aggressive pathogen- and tumor-destroying cells.

Some macrophages are localized (i.e., fixed) to a particular organ or tissue, especially regions where pathogen invasion or dust accumulation is likely to occur. The function of fixed macrophages is heterogeneous and is believed to be influenced by microenvironmental stimuli such as cytokines and pathogenic products. Examples of fixed macrophages are listed in Table 1.

TABLE 1

Nomenclature for Fixed Macrophages.

| Name of cell | Location |
| --- | --- |
| Dust cells/Alveolar macrophages | pulmonary alveolus of lungs |
| Histiocytes | connective tissue |
| Kupffer cells | liver |
| Microglia | neural tissue |
| Epithelioid cells | granulomas |
| Osteoclasts | bone |
| Sinusoidal lining cells | spleen |
| Mesangial cells | kidney |

Methods and materials necessary for indentifying, isolating and culturing macrophages (and their monocyte precursors) are known in the art. See, e.g., Alabraba et al. (2007) *J. Immunol. Methods* 326:139-144; Borgmann et al., "Isolation and HIV-1 infection of primary human microglia from fetal and adult tissue," 49-70 In: Methods in Molecular Biology (Zhu ed., Humana Press Inc. 2005); Buckley et al. (1985) *J. Immunol.* 134:2310-2315; Buckley et al., "Human osteoclast culture from peripheral blood monocytes," 55-68 In: Methods in Molecular Medicine (Picot ed., Humana Press Inc. 2$^{nd}$ ed. 2005); Cline (1994) *Blood* 84:2840-2853; Davies & Gordon, "Isolation and culture of human macrophages," 105-116 In: Basic Cell Culture Protocols (Helgason & Miller eds., Humana Press Inc. 3$^{rd}$ ed. 2005); Davies & Gordon, "Isolation and culture of murine macrophages," 91-103 In: Basic Cell Culture Protocols (Helgason & Miller eds., Humana Press Inc. 3$^{rd}$ ed. 2005); Fels & Cohn (1986) *J. Applied Physiology* 60:353-369; Gordon & Taylor (2005) *Nat. Rev. Immunol.* 5:953-964; Havenith et al. (1998) *Glia* 22:348-359; Rogler et al. (1998) *Clin. Exp. Immunol.* 112:205-215; Schuenke & Gelman (2003) *J. Neurovirol.* 9:346-357; St-Laurent et al. (2009) *J. Asthma* 46:1-8; Taylor et al. (2005) *Ann. Rev. Immunol.* 23:901-944; and Wilson & Stewart, "Glomerular epithelial and mesangial cell culture and characterization," 269-282 In: Methods in Molecular Medicine (Picot ed., Humana Press Inc. 2$^{nd}$ ed. 2005); each of which is incorporated herein by reference as if set forth in its entirety.

As noted above, macrophages can form multinucleate cells by fusing with themselves (i.e., homotypic fusion) or other cells (i.e., heterotypic fusion). See, Vignery (2005), supra. Although the mechanism by which macrophages fuse is not fully understood, it is shown below that SK4 channel upregulation and activity is involved and that blocking such upregulation or activity inhibits cell-cell fusion. Macrophage-derived multinucleate cells of particular interest herein are osteoclasts, giant cells and metastatic cancer cells.

As used herein, "homotypic fusion" means a cell-cell fusion between at least two cells of the same type such as macrophages. Examples of homotypic fusions with macrophages include, but are not limited to, giant cells, myoblasts, osteoclasts and syncytiotrophoblasts. In contrast, "heterotypic fusion" means a cell-cell fusion between at least two cells of differing lineages with at least one cell being a macrophage. Examples of heterotypic fusions with macrophages include, but are not limited to, metastatic cancer cells. See, id.

As used herein, "osteoclast" or "osteoclasts" means homotypic, specialized, multinucleated, macrophage-derived cells that solubilize bone tissue by removing its mineralized matrix. Such cells can express CD200, CT receptor or DC-STAMP. Morphologically, they are large, irregularly shaped cells with multiple, separate nuclei (about 2 to about 50) that are about the same size. Osteoclasts are also characterized by high expression of tartrate-resistant acid phosphatase (TRAP) and cathepsin K, as well as expression of vitronectin and calcitonin receptors. Osteoclasts are typically located in bone tissue and form from macrophages when stimulated at least by activator of nuclear factor κβ (RANK) ligand (RANKL) and macrophage colony-stimulating factor (M-CSF).

As used herein, "giant cell" or "giant cells" means homotypic, specialized, multinucleated, macrophage-derived cells that function in tissue homeostasis. Such cells can express CD200 or DC-STAMP. Morphologically, they are much like osteoclasts in that they are large, irregularly shaped cells with multiple, separate nuclei. Giant cells are believed to enhance defensive capabilities of macrophages and form from macrophages in response to a large foreign body, especially medical implants and chronic inflammation to pathogens, as well as granulomatous diseases. Interleukin-4 or interleukin-13 is believed to be required for giant cell formation.

As used herein, "metastatic cancer cell" or "metastatic cancer cells" means heterotypic, multinucleated macrophage- and cancer-derived cells. Typically, the cells are a hybrid having the macrophage's ability to move and the cancer cell's ability to divide. As such, metastatic cancer cells can migrate away from a primary site of tumor formation and take up residence in other areas of the body.

As used herein, "macrophage-derived multinucleate cell" or "macrophage-derived multinucleate cells" means cells having at least two or more nuclei resulting from homotypic or heterotypic fusion with macrophages. Examples of macrophage-derived multinucleate cells include, but are not limited to, breast cancer cells, multiple myeloma cells, osteoclasts, giant cells, and certain metastatic cancer cells.

The compositions and methods described herein find use in preventing and/or treating a variety of diseases or disorders where macrophage-derived multinucleate cells, particularly osteoclasts, giant cells, and metastatic cancer cells, are implicated. In particular, the SK4 channel inhibitors can be used to prevent or reduce bone resorption/bone loss, to prevent or treat an autoimmune or inflammatory disease or disorder, to prevent an implant or transplant rejection, or to prevent cancer metastasis.

Thus, in some embodiments of the invention, the compositions and methods are for use in treating or preventing bone loss and diseases associated with bone loss. With respect to bone-loss diseases, aberrant osteoclast formation can occur, which excessively resorbs bone and reduces bone mineral density (BMD). Examples of bone-loss diseases that can be prevented or treated with the compositions and methods of the invention include, but are not limited to, osteoporosis, osteomalacia, Paget's disease, periodontal disease, bone loss secondary to other pathological conditions (i.e., alcoholism, celiac disease, chronic kidney disease, chronic liver disease, epilepsy, gastrointestinal disease, hyperparathyroidism, hyperthyroidism, hypogonadism, leukemia, lymphoma, rheumatoid arthritis, scurvy, vitamin D deficiency), and the like.

In other embodiments of the invention, the compositions and methods are for use in treating or preventing autoimmune diseases, particularly those where giant cell formation is implicated. With respect to autoimmune diseases, giant cell formation can occur in response to an immune system's failure to recognize its own constituent parts as self, which results in cell and tissue destruction. The aberrant immune response may be restricted to certain organs (i.e., localized; e.g., in thyroiditis) or involve a particular tissue in different places (e.g., Goodpasture's disease, which may affect the basement membrane in both the lung and kidney) or may be systemic. Thus, preventing, modulating or inhibiting (i.e., reducing) giant cell formation in an autoimmune disease can ameliorate cell and tissue damage.

Examples of autoimmune diseases that can be prevented or treated with the compositions and methods of the invention include, but are not limited to, acute disseminated encephalomyelitis (ADEM), Addison's disease, alopecia, ankylosing spondylitis, antiphospholipid antibody syndrome, autoimmune inner ear disease, autoimmune hemolytic anemia, autoimmune hepatitis, Chagas disease, chronic obstructive pulmonary disease, celiac disease, Crohns Disease, dermatomyositis, diabetes mellitus type 1, endometriosis, Goodpasture's syndrome, Graves' disease, Guillain-Barré syndrome (GBS), Hashimoto's disease, Kawasaki disease, idiopathic thrombocytopenic purpura, systemic lupus erythematosus, multiple sclerosis (MS), myasthenia gravis, psoriasis, primary biliary cirrhosis, rheumatoid arthritis, scleroderma, Sjögren's syndrome, temporal arteritis (also known as "giant cell arteritis"), ulcerative colitis, vasculitis, and the like.

In yet other embodiments of the invention, the compositions and methods are for use in treating or preventing inflammatory diseases, particularly those where giant cell formation is implicated. With respect to inflammatory diseases, giant cell formation can occur when the immune system in the body overreacts to stimuli such as pathogens, damaged cells, or irritants. The overreactive immune response can be characterized by a persistence of inflammatory cells, including multinucleated giant cells, which cause inflammation and destroy healthy cells and tissues. Thus, preventing or inhibiting giant cell formation in an inflammatory disease can ameliorate inflammation and destructive cell and tissue damage.

Examples of inflammatory diseases that can be prevented or treated with the compositions and methods described herein include, but are not limited to, acne, asthma, arthrosclerosis, chronic obstructive pulmonary disease, colitis, dermatitis, glomerulonephritis, inflammatory bowel disease, eczema, keloid, lupus, nephritis, osteoarthritis, pelvic inflammatory disease, psoriasis, rheumatoid arthritis, tendinitis, and the like. To be clear, some autoimmune diseases listed above can be classified as both an autoimmune and inflammatory disease.

In other embodiments of the invention, the compositions and methods are for use in preventing implant and transplant rejection. Giant cell formation can occur in response to implants or transplanted cells, organs, or tissues. The immune system of the recipient can recognize implants (i.e., medical devices such as pacemakers) or transplanted cells, organs, or tissues as foreign and reject them, with the rejection being characterized by a persistence of inflammatory cells, including giant cells, which attack the implant and cause implant degradation or failure, or attack the transplanted cells/organ/tissue, just as it would destroy infecting organisms such as bacteria and viruses. Thus, preventing giant cell formation at the site of the implant or transplant can prevent or ameliorate rejection.

As used herein, "implant rejection" means an immune condition in which an implanted medical device is not accepted by the body of the implant recipient. Implants of interest include, but are not limited to, a cochlear device, artificial knee joint, artificial hip joint, bone cement, breast implant, cardiac implant (e.g., artificial heart valves, defibrillators, left-ventricular assist devices, pacemakers), dermal implant, gastric band or balloon, indwelling catheter, insulin pump, intrauterine device, neurological stimulator, ophthalmic implant, orthopedic implant, penile erectile prosthesis, stent, urethral sling, voice prosthesis, and the like. In view of the foregoing, it is also contemplated that implantable devices can be coated or impregnated with the compositions described herein to prevent or reduce the likelihood of rejection.

As used herein, "transplant rejection" means an immune condition in which a transplanted cell, tissue, or organ is not accepted by the body of the transplant recipient. In transplant rejection, the immune system of the recipient attacks the transplanted organ/tissue as foreign material in an attempt to destroy it.

Examples of transplant rejection include, but are not limited to, bone and bone marrow transplant, corneal transplant, heart and heart valve transplant, intestine transplant, kidney transplant, limb transplant, liver transplant, lung transplant, pancreas transplant, platelet transfusion, red blood cell transfusion, skin transplant, stem cell transplant, tendon transplant, vascular transplant, white blood cell transfusion, and the like.

In other embodiments of the invention, the compositions and methods are for use in preventing metastatic cell formation and cancer metastasis. With respect to metastasis, metastatic cells form from fusing macrophages and cancer cells, which then can spread from an original site (i.e., primary tumor) in the body to other parts of the body. Virtually all cancers can develop metastases, which can spread in three ways—(1) through local extension from the tumor to the surrounding tissues, (2) through the bloodstream to distant sites, or (3) through the lymphatic system to neighboring or distant lymph nodes. Thus, preventing metastatic cancer cell formation can beneficially prevent cancer metastasis.

Examples of cancers for which metastasis can be prevented with the compositions and methods of the invention include, but are not limited to, bone cancer, brain cancer, breast cancer, cervical cancer, colon cancer, intestinal cancer, liver cancer, lung cancer, pancreatic cancer, prostate cancer, rectal cancer, stomach cancer, throat cancer, uterine cancer, and the like.

The present invention includes compositions having an effective amount of an SK4 channel inhibitor and optionally a therapeutic agent for treating a disease or disorder mediated by macrophage-derived multinucleate cells. In one embodiment, a composition is provided that comprises an effective amount of an SK4 channel inhibitor and a therapeutic agent. In other embodiments, a pharmaceutical composition is provided that comprises a therapeutically effective amount of an SK4 inhibitor and a therapeutic agent, as well as a pharmaceutically acceptable carrier.

As used herein, an "SK4 channel inhibitor" or "SK4 channel inhibiting agent" means agents that affect SK4 channel expression (i.e., translation or transcription), SK4 channel activity (i.e., conductance), or upstream and downstream SK4 channel effectors (i.e., promoter activators, inducers, suppressors, repressors, kinases, etc.). In some embodiments, the SK4 channel inhibitor can be an inhibitory nucleic acid sequence, an anti-SK4 channel antibody, or other protein designed to bind SK4 channels and modulate their function (i.e., ability to depolarize or repolarize). Alternatively, the SK4 channel inhibitor can be a small molecule that specifically binds to SK4 channels and blocks their activity or function.

Regardless of the exact nature of the SK4 channel inhibitor, it decreases one or more of SK4 channel expression, activity or function. The expression, activity or function decreases by a statistically significant amount including, but not limited to, about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% compared to an appropriate control. Preferably, the SK4 channel expression, activity or function decreases by at least about 10% or more. Conversely, the SK4 channel inhibitor should not statistically increase SK4 channel expression, activity or function.

Agents that affect SK4 channel expression can include inhibitory nucleic acid molecules that inhibit the expression of the SK4 channel monomer. The inhibitory nucleic acid molecules may inhibit the expression of a monomer directly, by preventing translation of a messenger RNA encoding the SK4 channel monomer (e.g., sense suppression/cosuppression; antisense suppression; double-stranded RNA (dsRNA) interference via small interfering RNA, micro RNA or short hairpin RNA; amplicon-mediated interference; and ribozymes) or indirectly, by encoding a polypeptide that inhibits the transcription or translation of a gene or nucleic acid sequence encoding the SK4 channel monomer. Methods for inhibiting or eliminating the expression of a gene product in mammalian cells are well known in the art, and any such method may be used in the present invention to inhibit the expression of SK4 channel monomers.

For sense suppression/cosuppression, an expression cassette can be designed to express a cosuppressing nucleic acid molecule corresponding to a native gene or nucleic acid encoding an SK4 channel monomer (e.g., a gene or nucleic acid sequence comprising SEQ ID NOS:1, 3 or 5 or a sequence having substantial sequence identity to SEQ ID NOS:1, 3 or 5) in the "sense" orientation. The cosuppressing nucleic acid molecule can correspond to all or part of the gene or nucleic acid encoding the SK4 channel monomer, all or part of the 5' and/or 3' untranslated region of the gene or nucleic acid encoding the SK4 channel monomer, or all or part of the coding sequence and untranslated regions of the gene or nucleic acid encoding the SK4 channel monomer. In general, the cosuppressing nucleic acid molecule can comprise at least about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 850 or 1000 nucleotides, or can be of any size up to and including the full length nucleic acid sequence for an SK4 channel monomer. Where the cosuppressing nucleic acid molecule comprises all or part of the coding region for the SK4 channel monomer, the expression cassette can be designed to eliminate the start codon so that no functional SK4 channel monomer will be transcribed from the cosuppressing nucleic acid molecule. Over-expression of the cosuppressing nucleic acid molecule can result in reduced expression of the gene or nucleic acid encoding the SK4 channel monomer. Methods of using cosuppression to inhibit mammalian ion channels are well known in the art. See, e.g., Bingham (1997) *Cell* 90:385-387; and Int'l Patent Application Publication No. WO/1999/063081; each of which is incorporated herein by reference as if set forth in its entirety.

For antisense suppression, an expression cassette can be designed to express an antisense nucleic acid molecule complementary to all or part of a native gene or nucleic acid encoding the SK4 channel monomer. The antisense nucleic acid molecule can correspond to all or part of a complement of the gene or nucleic acid encoding the SK4 channel monomer, all or part of a complement of the 5' and/or 3' untranslated region of the gene or nucleic acid encoding the SK4 channel monomer, or all or part of a complement of both the coding sequence and the untranslated regions of the gene or nucleic acid encoding the SK4 channel monomer. The antisense nucleic acid molecule also can be fully complementary (i.e., 100% identical to the complement of the target nucleic acid sequence) or partially complementary (i.e., less than 100% identical to the complement of the target nucleic acid sequence) to the gene or nucleic acid encoding the SK4 channel monomer. Expression of the antisense nucleic acid molecule can result in reduced expression of the gene or nucleic acid encoding the SK4 channel monomer.

Regardless of the type of antisense nucleic acid molecule used, sequences of at least 25 nucleotides, 50, 100, 200, 300, 400, 450, 500, 550 nucleotides or greater can be used. Methods for using anti-sense nucleic acid molecules to inhibit the expression of mammalian ion channels are well known in the art. See, e.g., Eigel & Hadley (2001) *Am. J. Physiol. Heart Circ. Physiol.* 281:H2184-H2190; Meiri et al. (1997) *Proc. Natl. Acad. Sci. USA* 94:4430-4434; Sasamura et al. (2002) *Jpn. J. Pharmacol.* 90:164-172; Si et al. (2006) *Brit. J. Pharmacol.* 148:909-917; Tao et al. (2008) *Am. J. Physiol. Cell Physiol.* 295:C1409-C1416; Tharp et al. (2006) *Am. J. Physiol. Heart Circ. Physiol.* 291:H2493-H2503; Wang et al. (2007) *Oncogene* 26:5107-5114; and Waterhouse & Helliwell (2003) *Nat. Rev. Genet.* 4:29-38; each of which is incorporated herein by reference as if set forth in its entirety.

Efficiency of antisense suppression can be increased by including a poly-dT region in the expression cassette at a position 3' to the antisense sequence and 5' of the polyadenylation signal. See, US Patent Application Publication No. 2002/0048814; incorporated herein by reference as if set forth in its entirety.

For dsRNA interference, a sense nucleic acid molecule like that described above for cosuppression and an antisense nucleic acid molecule fully or partially complementary to the sense nucleic acid sequence are expressed in the same cell, resulting in inhibition of the expression of a native gene or nucleic acid encoding the SK4 channel monomer. Expression of the sense and antisense nucleic acid molecules can be accomplished by designing an expression cassette to comprise both sense and antisense sequences for the nucleic acid encoding the SK4 channel monomer. Alternatively, separate expression cassettes can be used for the sense and antisense nucleic acid molecule.

Regardless of the type of nucleic acid molecule used for dsRNA interference, sequences of at least 25 nucleotides, 50, 100, 200, 300, 400, 450, 500, 550 nucleotides or greater can be used. Methods for using dsRNA interference to inhibit the expression of mammalian ion channels are well known in the art. See, e.g., Cotella et al. (2005) *Biochem. Biophys. Res. Commun.* 330:555-560; and Palmer et al. (2006) *Cell Biochem. Biophys.* 46:175-191; each of which is incorporated herein by reference as if set forth in its entirety.

For amplicon-mediated interference, an amplicon expression construct can be designed having a nucleic acid sequence comprising a virus-derived sequence that contains all or part of a native gene or nucleic acid encoding the SK4 channel monomer. The viral sequences present in the transcription product of the amplicon expression cassette allow the transcription product to direct its own replication. The transcripts produced by the amplicon may be either sense or antisense relative to the gene or nucleic acid sequence encoding the SK4 channel.

Regardless of the type of nucleic acid molecule used, sequences of at least 25 nucleotides, 50, 100, 200, 300, 400, 450, 500, 550 nucleotides or greater can be used. Methods of using amplicons to inhibit or attenuate expression of mammalian ion channels are well known in the art. See, e.g., White et al. (2002) *J. Neurophysiol.* 87:2149-2157; incorporated herein by reference as if set forth in its entirety.

For ribozymes, an expression construct can be designed to express a nucleic acid molecule having catalytic activity toward a mRNA expressed by a native gene or a nucleic acid sequence encoding the SK4 channel. The catalytic nucleic acid molecule causes the degradation of the mRNA or nucleic acid encoding the SK4 channel resulting in reduced expression of the SK4 channel.

Regardless of the type of catalytic nucleic acid molecule used, sequences of at least 25 nucleotides, 50, 100, 200, 300, 400, 450, 500, 550 nucleotides or greater can be used. Methods of using ribozymes to inhibit or attenuate expression of mammalian ion channels are well known in the art. See, e.g., Liu et al. (2000) *J. Biol. Chem.* 275:8711-8718; and U.S. Pat. No. 4,987,071; each of which is incorporated herein by reference as if set forth in its entirety.

For micro RNA (miRNA) interference, an expression construct can be designed to express a nucleic acid molecule complimentary to a native gene or nucleic acid sequence encoding the SK4 channel monomer, such that the miRNA is transcribed, but not translated into the SK4 channel monomer (i.e., a non-coding RNA). Each primary transcript (a pri-miRNA) is processed into a short stem-loop structure called a pre-miRNA and finally into a functional miRNA. miRNAs consist of about twenty-two to about twenty-three ribonucleotides. Mature miRNA are highly efficient at inhibiting the expression of the gene or nucleic acid molecule encoding the SK4 channel monomer. Because mature miRNA molecules are partially complementary to one or more nucleic acid molecules encoding the SK4 channel monomer, they downregulate gene expression by inhibiting translation or sometimes facilitating cleavage of nucleic acid molecules encoding SK4 channel monomers. Methods of using miRNA molecules to inhibit the expression mammalian ion channels are well known in the art. See, e.g., Lee et al. (1993) *Cell* 75:843-854; and Xiao et al. (2007) *J. Biol. Chem.* 282:12363-12367; each of which is incorporated herein by reference as if set forth in its entirety.

For short hairpin RNA (shRNA) interference, an expression cassette can be designed to express a nucleic acid molecule complimentary to a native gene or nucleic acid encoding SK4 channel monomers that makes a tight hairpin turn that can be used to silence gene expression via RNA interference. shRNA interference also can be intron-containing hairpin RNA (ihpRNA) interference in which the expression cassette can be designed to express a nucleic acid encoding intron-spliced RNA with a hairpin structure.

Regardless of the type of shRNA molecule used, sequences of at least 25 nucleotides, 50, 100, 200, 300, 400, 450, 500, 550 nucleotides or greater can be used. Methods of using shRNA molecules to inhibit the expression genes encoding ion channels in mammals are well known in the art. See, e.g., Weaver et al. (2006) *Glia* 54:223-233; incorporated herein by reference as if set forth in its entirety.

The expression cassette for shRNA interference also can be designed such that the sense sequence and antisense sequence do not correspond to a nucleic acid sequence encoding the SK4 channel. Instead, the sense and antisense sequences flank a loop sequence that comprises a nucleotide sequence corresponding to all or part of the nucleic acid sequence encoding the SK4 channel monomer. Thus, the loop region determines the specificity of the RNA interference. See, e.g., Int'l Patent Application Publication No. WO 02/00904; incorporated herein by reference as if set forth in its entirety.

In addition, transcriptional gene silencing (TGS) can be accomplished through use of shRNA molecules where an inverted repeat of the hairpin shares sequence identity with the promoter region of a gene or nucleic acid encoding the SK4 channel monomer to be silenced. Processing of the shRNA into short RNAs that can interact with the homologous promoter region may trigger degradation or methylation to result in silencing (see, Aufsatz et al. (2002) Proc. Natl. Acad. Sci. 99:16499-16506; and Mette et al. (2000) EMBO J. 19:5194-5201; each of which is incorporated herein by reference as if set forth in its entirety).

Additional agents that affect SK4 channel activity or function can include peptides, proteins or small molecules that modulate SK4 channel activity or function. The peptide, protein or small molecule may inhibit conductance of SK4 channels or, e.g., activity of calmodulin (see, Fanger et al. (1999) J. Biol. Chem. 274:5746-575; incorporated herein by reference as if set forth in its entirety) or kinases that regulate SK4 channels (see, Gerlach et al. (2000) J. Biol. Chem. 275:585-598; incorporated herein by reference as if set forth in its entirety). Alternatively, the peptide, protein or small molecule may modulate the activity or function of an accessory molecule that is itself regulated by SK4 channel activation.

For inhibitory peptides or proteins, it can be an antibody that binds an SK4 channel monomer or SK4 channel homotetramer. As used herein, "antibody" or "antibodies" means an immunoglobulin molecule immunologically reactive with a particular antigen or epitope of the antigen. The term also includes genetically engineered forms such as chimeric antibodies (e.g., humanized murine antibodies) and heteroconjugate antibodies (e.g., bispecific antibodies). The term further includes bivalent or bispecific molecules, diabodies, triabodies and tetrabodies. Bivalent and bispecific molecules are described in, e.g., Kostelny et al. (1992) J. Immunol. 148:1547-1553; Pack & Pluckthun (1992) Biochemistry 31:1579-1584; Zhu et al. (1997) Protein Sci. 6:781-788; Hu et al. (1996) Cancer Res. 56:3055-3061; Adams et al. (1993) Cancer Res. 53:4026-4034; and McCartney et al. (1995) Protein Eng. 8:301-314; each of which is incorporated herein by reference as if set forth in its entirety.

Antibody also includes antigen-binding forms of antibodies, including fragments with antigen-binding capability (e.g., Fab', F(ab')$_2$, Fab, Fv, and rIgG). Treatment of antibodies with proteolytic enzymes, such as papain and pepsin, generates these antibody fragments, especially anti-SK4 channel antibody fragments. Antibody also refers to recombinant single chain Fv fragments (scFv). Preferably, antibodies employed to practice the methods described herein bind to its target protein with an affinity (association constant) of equal to or greater than $10^7$ M$^{-1}$.

The antibody can be a monoclonal or polyclonal antibody and can belong to any antibody class (i.e., IgG, IgM, IgA, etc.). Methods for making monoclonal antibodies (mAb) are well known in the art. For example, one of ordinary skill in the art can make monoclonal antibodies by isolating lymphocytes and fusing them with myeloma cells, thereby producing hybridomas. See, e.g., Milstein, In: Handbook of Experimental Immunology (Blackwell Scientific Publishing 1986); and Goding, In: Monoclonal Antibodies: Principles and Practice (Academic Press 1983); each of which is incorporated herein by reference as if set forth in its entirety. The cloned hybridomas are then screened for production of, e.g., anti-SK4 channel monomer or homotetramer antibodies (i.e., antibodies that bind preferentially to SK4 channel monomers, homotetramers or fragments thereof). Monoclonal antibodies are thus not limited by the manner in which the antibodies are produced, whether such production is in situ or not.

Alternatively, antibodies can be produced by recombinant DNA technology including, but not limited to, expression in bacteria, yeast, plants, insect cell lines, or mammalian cell lines. For example, one of ordinary skill in the art readily can isolated and sequence a nucleic acid sequence encoding a monoclonal antibody using conventional procedures (e.g., by using oligonucleotide probes that are capable of binding specifically to genes encoding the heavy and light chains of an antibody). Hybridoma cells can serve as a preferred source of DNA for the nucleic acid sequence. Once isolated, the nucleic acid sequence can be placed into expression vectors, which are then transfected into host cells such as E. coli cells, simian COS cells, Chinese Hamster Ovary (CHO) cells, myeloma cells, or plant cells that do not otherwise produce antibodies, to obtain the synthesis of monoclonal antibodies in the recombinant host cells. Review articles on recombinant expression in bacteria of DNA encoding an antibody include the following: Skerra (1993) Curr. Opin. Immunol. 5:256-262; and Phickthun (1992) Immunol. Rev. 130:151-188; each of which is incorporated herein by reference as if set forth in its entirety.

Alternatively, antibodies can be produced in a cell line such as a CHO cell line. See, e.g., U.S. Pat. Nos. 5,545,403; 5,545,405 and 5,998,144; each of which is incorporated herein by reference as if set forth in its entirety. Briefly, one of ordinary skill in the art can transfect the cell line with vectors capable of expressing a light chain and a heavy chain, respectively. By transfecting the two protein chains on separate vectors, chimeric antibodies can be produced. Another advantage of using CHO cells is the correct glycosylation of the antibody.

Likewise, methods of making polyclonal antibodies are well known in the art. For example, one of ordinary skill in the art can make polyclonal antibodies by immunizing a suitable host animal, e.g., such as a rabbit, with an immunogen (e.g., an SK4 channel monomer, SK4 channel homotetramer or fragments thereof) and using properly diluted serum or isolating immunoglobulins from the serum. The animal therefore can be inoculated with the immunogen, with blood subsequently being removed from the animal and an IgG fraction purified. Other suitable host animals include a chicken, goat, sheep, guinea pig, rat, or mouse. If desired, the immunogen can be administered as a conjugate in which it is coupled, e.g., via a side chain of one of its amino acid residues, to a suitable carrier. The carrier molecule is typically a physiologically acceptable carrier. The antibody obtained can be purified to a purity of up to about 70%, 80%, 90%, 95%, 99% or 100%.

Methods of making anti-SK4 channel monomer or homotetramer antibodies are known in the art. See, e.g., Boettger et al. (2002) Brain 125:252-263; Furness et al. (2004) Autonom. Neurosci. 112:93-97; Ghanshani et al. (2000) J. Biol. Chem. 275:37137-37149; and Hoffman et al. (2003) Proc. Natl. Acad. Sci. USA 100:7366-7371; each of which is incorporated herein by reference as if set forth in its entirety. Likewise, commercially available anti-SK4 channel antibodies are suitable for use herein, and can be obtained from, e.g., Alomone Labs (Jerusalem, Israel); Millipore (Billerica, Mass.), Sigma Aldrich (St. Louis, Mo.), and Santa Cruz Biotechnology (Santa Cruz, Calif.), respectively. See also, Sandow et al. (2006) *J. Anat.* 209:689-698; and Wulff et al. (2001) *J. Biol. Chem.* 276:32040-32045.

Alternatively, the SK4 channel inhibitor can be a protein designed to bind SK4 channel monomers or homotetramers. As used herein, a "protein designed to bind SK4 channel monomers or homotetramers" means a protein designed to bind SK4 channel monomers or homotetramers, wherein the binding inhibits (i.e., reduces) SK4 channel expression, activity, or function, as noted herein above. Inhibitory peptides are well known in the art. See, e.g., Wulff et al. (2007) *Curr. Med. Chem.* 14:1437-1457; incorporated herein by reference as if set forth in its entirety.

Alternatively, the SK4 channel inhibitor can be a small molecule that binds to an SK4 channel monomer to prevent it from forming part of a homotetramer or binds to a homotetramer and prevents is activity or function. As used herein, a "small molecule that binds to an SK4 channel monomer" or "small molecule that binds to an SK4 homotetramer" means a molecule of a size comparable to those molecules generally used in pharmaceuticals that inhibits the expression, activity, or function of SK4 channel monomers or homotetramers. Preferred small molecules can range in size up to about 5000 Da, more preferably up to about 2000 Da, and most preferably up to about 1000 Da.

Non-limiting examples of small molecules for use herein include chemical compounds, inorganic molecules, organic molecules, organic molecules containing an inorganic component, molecules including a radioactive atom, synthetic molecules and peptidomimetics (e.g., short, peptide fragments that mimic the most common peptide motifs, such as an α-helix or β-sheet). As an SK4 channel inhibitor, the small molecule may be more permeable to cells, less susceptible to degradation and less apt to elicit an undesired immune response than large molecules.

For small molecules, it can be a chemical compound that can bind an SK4 channel monomer or homotetramer. One class of small molecules useful herein is triarylmethanes. Triarylmethanes can have the following structural formula:

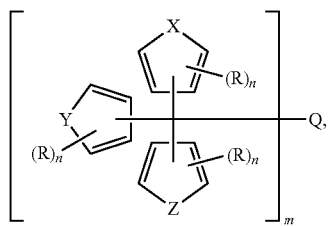

wherein X, Y and Z can be the same or different and can be independently selected from $CH_2$, O, S, $NR_1$, N=CH, CH=N and $R_2$—C=C—$R_3$;

R can be H, halogen, trihaloalkyl, hydroxy, acyloxy, alkoxy, alkenyloxy, thio, alkylthio, nitro, cyano, ureido, acyl, carboxy, alkoxycarbonyl, N—$(R_4)(R_5)$ and saturated or unsaturated, chiral or achiral, cyclic or acyclic, straight or branched hydrocarbyl group with from 1 to 20 carbon atoms, optionally substituted with hydroxy, halogen, trihaloalkyl, alkylthio, alkoxy, carboxy, alkoxycarbonyl, oxoalkyl, cyano and N—$(R_4)(R_5)$ group;

$R_1$ can be H, alkyl, alkenyl, alkynyl, cycloalkyl, aryl, acyl and aroyl, optionally substituted with hydroxy, amino, substituted amino, cyano, alkoxy, halogen, trihaloalkyl, nitro, thio, alkylthio, carboxy and alkoxycarbonyl groups;

$R_2$ and $R_3$ can be H or can combine to form a saturated or unsaturated carbocyclic or heterocyclic ring, optionally substituted with one or more R groups;

$R_4$ and $R_5$ can be H, alkyl, alkenyl, alkynyl, cycloalkyl and acyl or $R_4$ and $R_5$ can combine to form a ring, wherein a carbon may be optionally substituted by a heteroatom selected from O, S or N—$R_6$;

$R_6$ can be H, alkyl, alkenyl, alkynyl, cycloalkyl, hydroxyalkyl or carboxyalkyl; n can be 1-5; m can be 1 or 2, with the proviso that when m can be 1, Q can be OH, CN, carboxyalkyl', N—$(R_7)(R_8)$, where $R_7$ and $R_8$ can be H, lower alkyl (1-4C), cycloalkyl, aryl, acyl, amido, or $R_7$ and $R_8$ can combine to form a saturated or unsaturated heterocyclic ring and optionally substituted with up to 3 additional heteroatoms such as N, O and S; or —NH-heterocycle, where the heterocycle can be thiazole, oxazole, isoxazole, pyridine, pyrimidine and purine; when m can be 2, Q can be a spacer of from 2-10 carbons as a straight or branched, chiral or achiral, cyclic or acyclic, saturated or unsaturated, hydrocarbon group such as phenyl.

Examples of triarylmethanes useful herein include, but are not limited to, 1-[(2-chlorophenyl)-diphenylmethyl]-1H-imidazole (clotrimazole; Ishii et al. (1997), supra; Joiner et al. (1997), supra; and Logsdon et al. (1997), supra); 2,2-bis(4-fluorophenyl)-2-phenylacetamide (ICA-17043; Stocker et al. (2003) *Blood* 101:2412-2418); 1-[(2-chlorophenyl)diphenylmethyl]-1H-pyrazole (TRAM-34; Wulff et al. (2000) *Proc. Natl. Acad. Sci. USA* 97:8151-8156; incorporated herein by reference as if set forth in its entirety); 1-[(2-fluorophenyl)diphenylmethyl]-1H-pyrazole; 1-[(4-chlorophenyl)diphenylmethyl]-1H-pyrazole; 1-[(2-fluorophenyl)diphenylmethyl]-1H-pyrazole; and 1-[(2-chlorophenyl)diphenylmethyl]-1H-tetrazole. Additional small molecules are known in the art. See, McNaughton-Smith et al. (2008) *J. Med. Chem.* 51:976-982; Wulff (2007), supra; and Int'l Patent Application Publication No. WO 2007/033307; each of which is incorporated herein by reference as if set forth in its entirety).

Compounds of interest can include 2,2-bis-(4-fluorophenyl)-3-methyl-butyramide (below), described in WO03/059873 (granted U.S. Pat. No. 7,208,527 B2) and (WO09/027292), herein incorporated by reference:

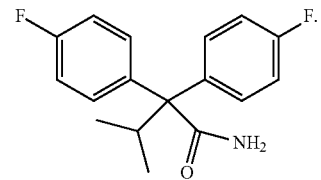 [SMILES: CC(C)C(C(N)=O)(c1ccc(F)cc1)c1ccc(F)cc1]

$K_{ATP}$ channel blockers of the invention can include a compound of the formula:

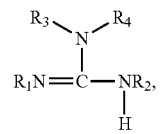

wherein R1, R2, R3 and R4 can be individually selected from adamantyl, hydrogen, alkyl of one to eight carbon atoms, inclusive, cycloalkyl of five to eight carbon atoms, inclusive, phenyl, phenalkyl where alkyl can be one to three carbon atoms, inclusive, and mono- or di-substituted phenyl or phenyl moiety of the phenalkyl wherein the substituents can be the same or different and can be selected from the group consisting of alkyl of one to three carbon atoms, inclusive, halogen, trifluoromethyl and alkoxy of from one to three carbon atoms, inclusive, halo, and trifluoromethyl; hydrogen and alkyl of one to eight carbon atoms, inclusive, cycloalkyl of five to eight carbon atoms, inclusive, and when taken together with the nitrogen atom to which they are attached form a saturated heterocyclic ring with methylene, or nitrogen coupled with hydrogen or alkyl of one to three carbon atoms, inclusive, oxygen; or sulphur. When the heterocyclic ring is with methylene, the heterocyclic ring can have from four to six carbon atoms. When the heterocyclic ring is with oxygen or sulfur, the heterocyclic ring can be piperazino, N-alkylpiperazino, morpholino or thiomorpholino, and pharmaceutically acceptable acid addition salts thereof.

These $K_{ATP}$ channel blockers can include those selected from the following: 2,3-butanedione monoxime; 4-aminopyridine (4-AP); 5-Hydroxydecanoate; 7 nitroindazole; 8-oxo-berberine; A-184209; acecainide; adenosine (ATP); Aflatrem; Agatoxin, ω-type (ω-Agatoxin); Agitoxin-1; Agitoxin-2; Agitoxin-3; AL 275; Alinidine ST 567; Almokalant H 234/09; Alpha-dendrotoxin; AM 92016; Ambasilide; Ambasilide LU 47110; AN 132; Antioxidants; Apamin; ARH 050642; ATI 2042; ATP; AWD 12-260; AWD 160275; AWD 23-111; AZD 7009; AZDF 265; Azimilide; Barium chloride; Bay K8644 (R)-(+)-form; BDS-I; BDS-II; Bepridil; Berlambine; Bertosamil; Beta-bungarotoxin (beta-BuTX); Beta-dendrotoxin; BHA 0388; BMS 208782; BMS 208783; BRBI 28; Bretylium; BRL 32872; Bromide dendrotoxin; BTS 67582; Bupiva-caine; Carsatrin Succinate RWJ 24517; Caryachine; CGX 1007; Changrolin pyrozoline; Charybdotoxin; Charylotoxin; CHF 1522 Cyclo-dextrin complex of glibenclamide; Chiorpropamide; Chromanol 293 isomer; Chromanol 293B; Cibenzoline; Ciclazindol; Clamikalant HMR 1098; Clamikalant HMR 1883; Clausenamide (−form); Clausenamide (racemic); Clofilium LY 150378; Clofilium tosylate; Clotrimaxole; Clotrimazole; CNS 1237; CP 308408; CP 339818; CP 366660; CP 92713; CPU 86017; Cyanoguanidine; Dendrotoxin (DTX); Dendrotoxin I (DTX-I); Dendrotoxin K(DTX-K); Dequalinium chloride; Dexsotalol BMY; 057631D d-sotalol; Dicentrine; Dimethyl sulfoxide; DKAH 269; DMP 543; Dofetilide; DPC 543; DPI 201106; Dronedarone SR 33589; DTX, α-type (α-DTX); DTX, (β-type (β-DTX); DTX, γ-type (γ-DTX); DTX, σ-type (σ-DTX); E-4031; Efaroxan; EGIS 7229; Englitazone; Ersentilide (+/− form); Ersentilide (S-form); Ethanol; Evodiamine (S); Fampridine 4-aminopyridine EL 970; Fosinoprilat; Gamma-dendrotoxin; GEA 857; Glemanserin MDL 11939; GLG V 13; Glibenclamide; Glimepiride; Glipizide (GLP); Glipizide K 4024; Glipizide TK 1320; Glucagons antagonists; Glybenclamide; Glyburide; Guanethidine; Guanidinium moieties; GYKI 16638; HA 7; HMR 1372; HMR 1402; HMR 1556; HMR 1883; Hydroxy; Iberiotoxin; Ibutilide; Ibutilide U 70226; ICA 17043; ICI 181037; SK4 Channel Blocker; IMID-1M; IMID-26F; IMID-4F; IMID-4F hydrochloride; Imidazoline moieties; Ipazilide WIN 54177; Ipidacrine NIK 247; Ivabradine; JKL 1073A oxy-berberine; JTV 519; Kaliotoxin; KCB 328; KMC IV 84; KW 3407; L 691121; L 702958; L 706000; L 735821; L 742084; L 768673; L755860 and related compounds; Levosemotiadil SA 3212; Levosemotiadil SD 3212; Limbatoxin; Limbatustoxin; Liriodenine; Lq2; LQE 908 Pinokalant; LY 190147; LY 97241; Margatoxin; Mitiglinide KAD 1229 S-21403; MK 499; N 3601; N-ally) secoboldine; Nateglinide; Nateglinide AY 4166; Neuropeptide Y; Nibentan; Nifekalant MS 551; Niguldipine hydrochloride S(+)-form; NIP 142; NOS inhibitors; Noxiustoxin; NS 004; NS 1546; OPC 88117; ORG 20781; Pandinotoxin-Kα; Paspalitrem; Paxilline; PD 157667; Penitrem A; PGE 844384; Phencyclidine; Phentolamine; Phentolamine; Pirmenol C1845; Pirocixan; PNU 18177A; PNU 37883A; PNU 89692; PNU 94126; PNU 94158; PNU 94563; PNU 94750; PNU 96179; PNU 96293; PNU 97025E; PNU 99963; Pyrido triazoles; Quinidine; Quinine; Quinine hemisulfate salt; Repaglinide AGEE 623; Repaglinide NN 623; Repagliniide; Rimonabant SR 141716; Risotilide; Ro034563; Ropivacaine AL 281; Ropivacaine LEA 103; RP 58866; RP 66784 RSD 1000; RSD 1019; Rutaecarpine; RWJ 28810; RX 871024; S 16260; S 9947; Salicylaldoxime; Saxitoxin; SB 237376; Scyllatoxin; SDZ DNJ 608; Sematilide; Sematilide CK 1752; Sematilide ZK 110516; Sinominine; Sodium 5-hydroxydecanoate; Sotalol; SPM 928; Spriadoilne; SSR 149744B; Stichodactyla toxin; Sulfonylureas; TEA (tetraethylammonium); Tedisamil; Tedisamil KC 8857; Terikalant RP 62719; Tertiapin; Tertiapin-Q; Tetraethylammonium chloride; Tetraethylammonium ions; Tetrodotoxin; TH 9121; TH 9122; Tityustoxin K; Tityustoxin-Kα; TMB-8; TN 871; Tolazamide; Tolbutamide; Toxin based therapeutics BRI 6906; TRAM 30; Troglitazone; U 37883A; U 50488H; U-37883A; U-45194A; UCL 1439; UCL 1530; UCL 1559; UCL1608; UCL 1684; UK 66914; UK 78282; WAY 123223; WAY 123398; WIN 17317-3; WIN 61773; XE 991; Y 39677; YM 026; YM 19348 Racemate; YM 193489-R; YM 193489-S; YT 1; Zatebradine; ZM 181037; ZM 181037; ZM 244085. See, WO 2007/009462, herein incorporated by reference.

Compounds of interest also can include those having the following formula:

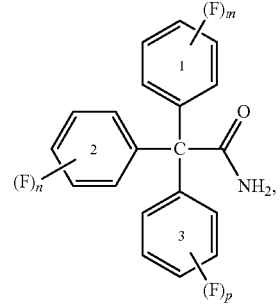

wherein m, n and p can be independently selected from 0 and 1 and at least one of m, n and p can be 1.

In an exemplary embodiment, when m, n and p are all 1, the fluoro substituents at ring 1 and at ring 2 are located at a position independently selected from ortho to the acetamide substituent, meta to the acetamide substituent and para to the acetamide substituent, and the substituent at ring 3 is at a position selected from ortho to the acetamide substituent and para to the acetamide substituent. In another exemplary embodiment, when p is 0, and m is 1 and n is 1, the fluoro substituent at ring 1 is para to the acetamide substituent, and the substituent at ring 2 is located at a position selected from ortho to the acetamide substituent and para to the acetamide substituent. See, WO 2007/075849, herein incorporated by reference.

Compounds of interest also can include those having the following formula:

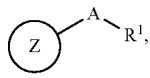

wherein the ring system Z can be substituted or unsubstituted aryl, and substituted or unsubstituted 5-membered heterocycle. The symbol A represents —NHS(0)$_2$-, —S(0)$_2$NH—, —C(R$^3$R$^4$)S(0)$_n$-, or —S(0)$_n$, C(R$^3$R$^4$)—, in which R3 and R4 are independently selected from hydrogen, substituted or unsubstituted lower alkyl, OR$^5$ and —CF$^3$. The symbol R$^5$ represents hydrogen, substituted or unsubstituted lower alkyl, or CF$^3$. The integer n is selected from 0 to 2. The symbol R$^1$ represents substituted or unsubstituted aryl, substituted or unsubstituted heteroaryl group, substituted or unsubstituted (C$_5$-C$_7$)carbocycle or substituted or unsubstituted (C$_5$-C$_7$)heterocycle;

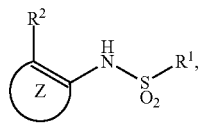

wherein the ring system Z can be selected from substituted or unsubstituted aryl, and substituted and unsubstituted 5-membered heterocycle. The symbol R$^1$ represents a substituted or unsubstituted aryl group, a substituted or unsubstituted heteroaryl group, a substituted or unsubstituted (C$_5$-C$_7$)carbocycle or a substituted or unsubstituted (C$_5$-C$_7$) heterocycle. The symbol R$^2$ represents COOR$^6$, substituted or unsubstituted 2-furan, substituted or unsubstituted 2-thiazole or

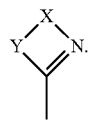

The symbol R$^6$ represents a substituted or unsubstituted C$_1$-C$_4$ alkyl group, e.g., methyl, ethyl, and —CF$_3$. X represents —N=N—, —N=C(R$^7$)—, —C(R$^7$R$^8$)—C(R$^7$R$^8$)— or —C(R7)=C(R8)-, in which R7 and R8 independently represent hydrogen, substituted and unsubstituted lower alkyl or —CF$_3$. The symbol Y represents 0, NR$^9$ or S, in which R$^9$ is H, lower alkyl or —CF$_3$;

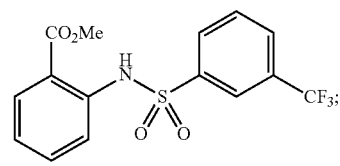

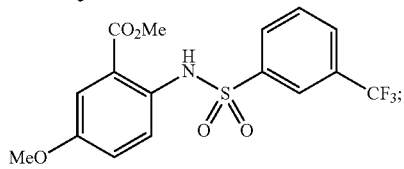

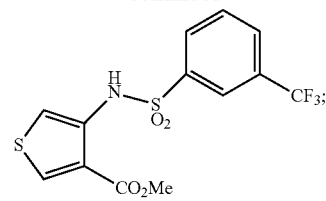

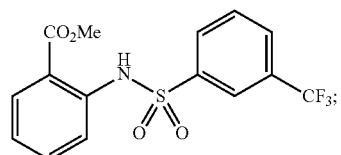

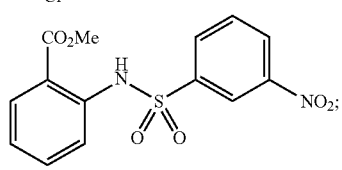

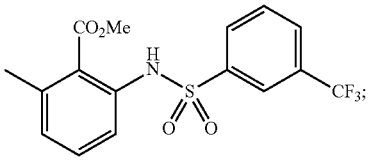

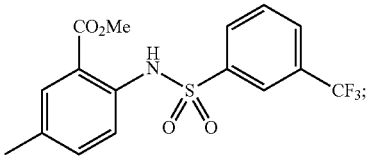

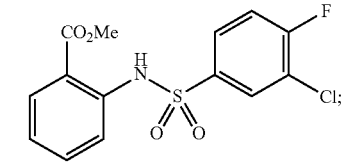

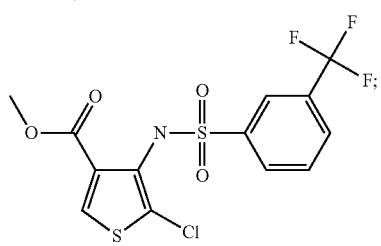

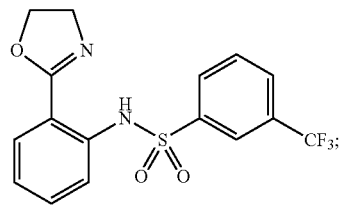

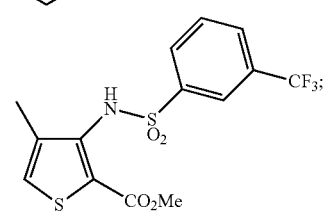

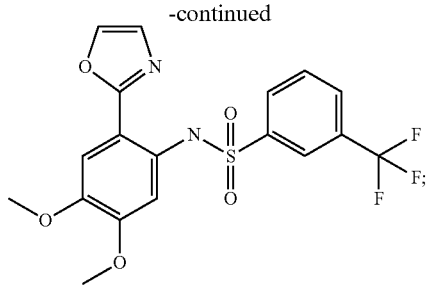

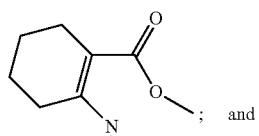; and

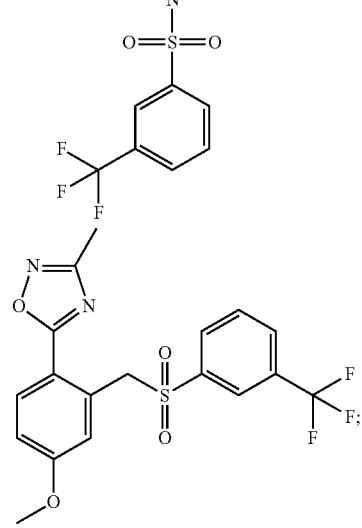

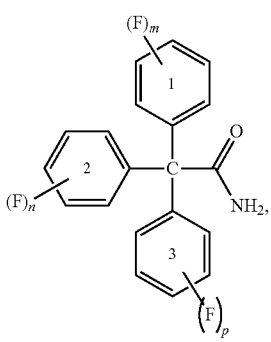

wherein, m, n and p can be independently selected from 0 and 1 and at least one of m, n and p is 1; when m, n and p are all 1, the fluoro substituents at ring 1 and at ring 2 are located at a position independently selected from ortho to the acetamide substituent, meta to the acetamide substituent and para to the acetamide substituent, and the substituent at ring 3 can be at a position selected from ortho to the acetamide substituent and para to the acetamide substituent; and when p is 0, and m is 1 and n is 1, the fluoro substituent at ring 1 is para to the acetamide substituent, and the substituent at ring 2 is located at a position selected from ortho to the acetamide substituent and para to the acetamide substituent;

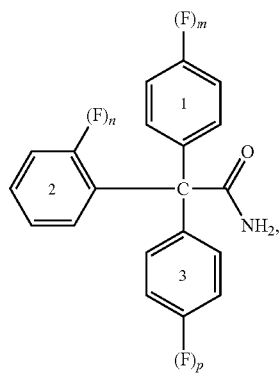

wherein m, n and p can be independently selected from 0 and 1, and at least one of m, n, and p is 1;

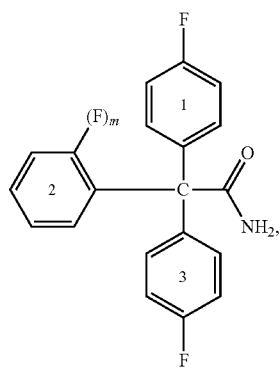

wherein m is either 0 or 1;

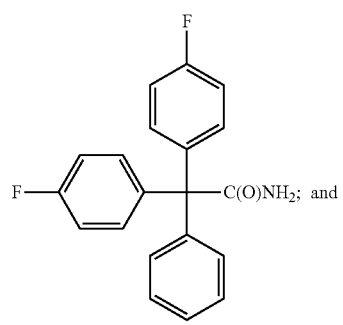

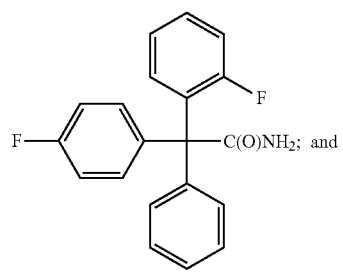

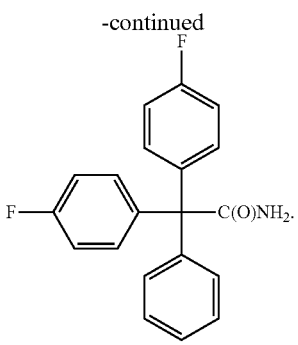

Compounds of interest also can include those having the following formula:

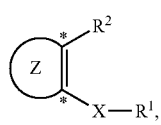

wherein, ring system Z can be selected from substituted or unsubstituted aryl, unsubstituted carbocycles of from 5 to 7 members, substituted or unsubstituted carbocycles having from 4 to 8 members, substituted or unsubstituted heterocycles having from 4 to 8 members, and substituted or unsubstituted heteroaryl having from 4 to 8 members; X can be a member selected from the group of —NHS(0)$^2$-, —S(0)$^2$NR3-, and NHC=NR$^3$, wherein R$^3$ can be selected from H, and substituted or unsubstituted (C$_1$-C$_4$)alkyl;

R1 can be selected from substituted or unsubstituted aryl, substituted or unsubstituted heteroaryl, substituted or unsubstituted (C$_5$-C$_7$)carbocycle and substituted or unsubstituted (C$_5$-C$_7$)heterocycle; R$^2$ can be a member selected from —C$_1$, —CF$_3$, —CO$_2$R$^4$, substituted or unsubstituted aryl, substituted or unsubstituted heterocycle of from 5 to 6 members, and substituted or unsubstituted heteroaryl of from 5 to 6 members, wherein R$^4$ can be a substituted or unsubstituted (C$_1$-C$_4$)alkyl group, which is optionally connected to ring system Z, forming a lactone having from 5 to 7 members; and wherein the double bond between the two carbons marked * can be endocyclic to ring system Z. See, WO 03/074038, incorporated herein by reference.

Carbonylamino derivatives for use in the invention include:

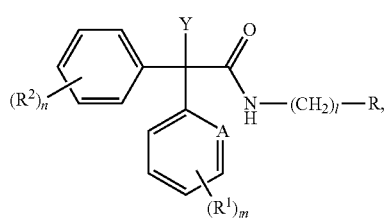

any of its enantiomers or any mixture of enantiomers, or a pharmaceutically acceptable addition salt thereof, wherein A can be CH or N; R can be hydrogen, alkyl, alkenyl, alkynyl, cycloalkyl, cycloalkyl-alkyl, alkoxy or CF$_3$; Y represents hydrogen, alkyl, alkenyl, alkynyl, cycloalkyl, cycloalkyl-alkyl, or a group of the formula:

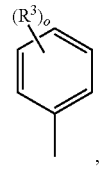

wherein R$^1$, R$^2$ and R$^3$, independently of each another, can be hydrogen, halogen, CN, NO$_2$ or CF$_3$; I can be 0, 1, 2, 3, 4, 5 or 6; and m, n and o, independent of each another, can be 0, 1 or 2.

Alternatively, m, n and o, independent of each another, can be 0 or 1;

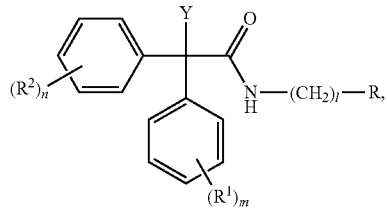

wherein I, m, n, Y, R, R$^1$ and R$^2$ are as defined above.

Alternatively, the carbonylamino derivative of the invention can be a compound of Formula II, wherein Y can be alkyl, cycloalkyl, cycloalkyl-alkyl or alkenyl; I can be 0; m and n, independently of each another, can be 0 or 1; and R represents hydrogen.

Alternatively, the carbonylamino derivative of Formula II can be N-pentyl-2,2-diphenyl-acetamide; N-hexyl-2,2-diphenyl-acetamide; N-cyclopropylmethyl-2,2-diphenyl-acetamide; or N-hex-2-enyl-2,2-diphenyl-acetamide; or a pharmaceutically-acceptable addition salt hereof;

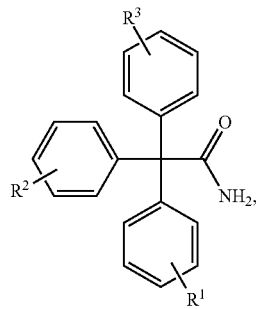

wherein R$^1$, R$^2$ and R$^3$ are as defined above.

Alternatively, the carbonylamino derivative of the invention can be a triaryl methane of Formula III wherein R$^1$, R$^2$ and R$^3$, independently of each another, can be hydrogen or fluoro.

Alternatively, the triaryl methane derivative can be selected from 2,2,2-triphenyl-acetamide; 2-(2-fluoro-phenyl)-2,2-diphenyl-acetamide; 2-(2-fluoro-phenyl)-2,2-diphenyl-acetamide; 2-(4-fluoro-phenyl)-2,2-diphenyl-acetamide; 2,2-bis-(2-fluoro-phenyl)-2-phenyl-acetamide; 2-phenyl-2-(2-fluoro-phenyl)-2-(4-fluoro-phenyl)-acetamide; 2,2-bis-(2-fluoro-phenyl)-2-phenyl-acetamide; 2,2-bis-(4-fluoro-phenyl)-2-phenyl-acetamide; or a pharmaceutically-acceptable addition salt thereof;

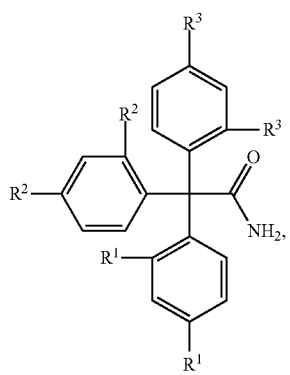

in which formula R¹, R² and R³ are as defined above.

Alternatively, the triaryl methane invention can be Formula IV, wherein R¹, R² and R³, each another, represent hydrogen or fluoro.

Alternatively, the triaryl methane derivative of the invention can be selected from 2,2,2-tri-(2-fluoro-phenyl)-acetamide; 2,2-bis-(2-fluoro-phenyl)-2-(4-fluoro-phenyl)-acetamide; 2,2-bis-(4-fluoro-phenyl)-2-(2-fluoro-phenyl)-acetamide; 2,2,2-tri-(4-fluoro-phenyl)-acetamide; or a pharmaceutically acceptable addition salt thereof;

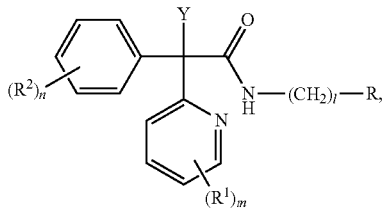

wherein I, m, n, Y, R, R¹ and R² are as defined above.

Alternatively, the carbonylamino derivative of the invention can be Formula V, wherein Y represents alkyl, cycloalkyl, cycloalkyl-alkyl or alkenyl; I can be 0; m and n, independently of each another, can be 0 or 1; R can be hydrogen; and R1 and R2, independently of each another, can be hydrogen or fluoro.

Carbonylamino derivatives therefore can be selected from (RS)—N-cyclopropylmethyl-2-phenyl-2-pyridin-2-yl-acetamide; (RS)-2-(3,4-difluoro-phenyl)-N-hexyl-2-pyridin-2-yl-acetamide; or (RS)—N-hexyl-2-(4-nitrophenyl)-2-pyridin-3-yl-acetamide; or a pharmaceutically acceptable addition salt thereof. See, WO 03/004101 incorporated herein by reference.

Compounds of interest also can include those having the following formula:

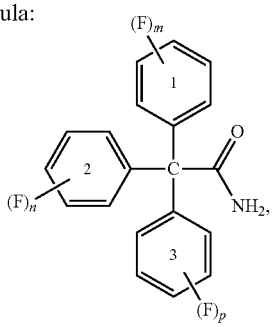

wherein m, n and p can be independently selected from 0 and 1 and at least one of m, n and p is 1; when m, n and p are all 1, the fluoro substituents at ring 1 and at ring 2 can be located at a position independently selected from ortho to the acetamide substituent, meta to the acetamide substituent and para to the acetamide substituent, and the substituent at ring 3 can be at a position selected from ortho to the acetamide substituent para to the acetamide substituent; and when p is 0, and m is 1 and n is 1, the fluoro substituent at ring 1 can be para to the acetamide substituent, and the substituent at ring 2 can be at a position selected from ortho to the acetamide substituent and para to the acetamide substituent;

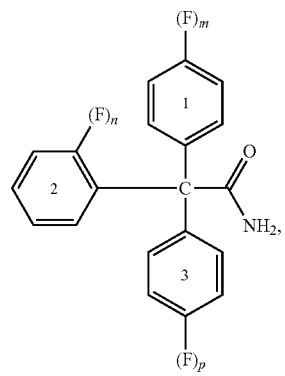

wherein, m, n and p can be independently selected from 0 and 1, and at least one of m, n and p is 1;

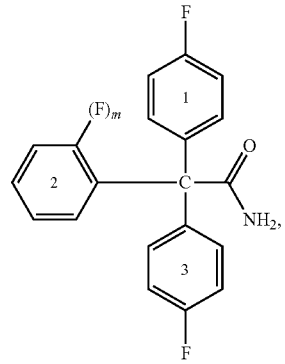

wherein m can be either 0 or 1. See, WO 00/50026, incorporated herein by reference.

Other small molecules useful in the invention can include: maurotoxin (Castle et al. (2003) *Mol. Pharmacol.* 63:409-418). Still other small molecules useful herein can include those disclosed in Int'l Patent Application Publication Nos. WO 97/034589, WO 99/026628, WO 99/026929, WO 2000/050026, WO 2000/069439, WO 2000/069794, WO 2000/069823, WO 2001/049663, WO 2004/016221, WO 2005/003094, WO 2005/003143, WO 2006/084031 and WO 2009/027292; each of which is incorporated herein by reference as if set forth in its entirety.

As used herein, an "effective amount" or "therapeutically effective amount" (i.e., dosage) means an amount of the SK4 channel inhibitor provided in vitro or in vivo, respectively, sufficient to contact and operably complex with nucleic acids encoding SK4 channels, to contact and operably complex (either covalently or non-covalently) with SK4 channel subunit polypeptides or homotetramers, or to contact and operably complex with upstream (e.g., enhancers, promoters, etc.) or downstream (e.g., kinases (MEK/ERK), phosphatases or phosphorylases) effectors of SK4 channels. Moreover, the effective amount or therapeutically effective amount of the SK4 channel inhibitor is an amount that is sufficient to achieve a desired effect, such as decreasing SK4 channel mRNA, decreasing SK4 channel activity, or decreasing function of elements downstream of SK4 channels. For example, this can be the amount of the SK4 channel inhibitor useful in preventing or overcoming various immune disorders such as arthritis, allergy, or asthma. The therapeutically effective amount of the SK4 channel inhibitor will depend on the subject being treated, the severity of the disorder or disease, and the manner of administration. Alternatively, this amount can be the amount that would achieve a target tissue concentration similar to that which produces a desired effect in vitro.

With respect to the therapeutically effective amount of the SK4 channel inhibitor, it can be determined by in vitro or in vivo animal studies. The therapeutically effective amount (i.e., dosage) can be administered to the subject to provide a target tissue concentration similar to that which has been shown to be effective in the animal assays. It is contemplated that genetically modified animals may be useful for exaggerating SK4 channel expression, activity, and function. Examples of genetically modified animals that can be used include, but are not limited to, SK4$^{-/-}$ animals and the like. See, e.g., Begenisich et al. (2004) *J. Biol. Chem.* 279:47681-47687; incorporated herein by reference as if set forth in its entirety.

The effective and therapeutically effective amounts of the SK4 channel inhibitor can and will vary depending upon the type of agent provided. For example, the therapeutically effective amount of an anti-SK4 channel antibody or small molecule inhibitor can be from about 0.0001 mg/kg to about 200 mg/kg of body weight per day in the treatment of immune system disorders, or alternatively from about 0.1 mg to about 20 g per subject per day. For example, osteoporosis can be effectively treated by the administration from about 0.001 mg to about 100 mg of a small molecule such as a triarylmethane per kg of body weight per day, or alternatively from about 0.5 mg to about 10 g per subject per day.

As noted above, the composition also can include a therapeutic agent or combination thereof. Examples of therapeutic agents include, but are not limited to anti-bone-loss agents, anti-inflammatory agents, immunosuppressive agents and chemotherapeutic agents.

Examples of anti-bone-loss agents include, but are not limited to, calcium and vitamin D; bisphosphonates (e.g., sodium alendronate (Fosamax®; Merck & Co., Inc.; Whitehouse Station, N.J.), risedronate (Actonel®; Procter & Gamble Pharmaceuticals; Cincinnati, Ohio), and ibandronate (Boniva®; Hoffman-La Roche Inc.; Nutley, N.J.)); estrogen replacement therapy; parathyroid hormone and teriparatide (Forteo®; Eli Lilly & Co.; Indianapolis, Ind.); strontium ranelate (Protelos® or Protos®; Servier Laboratories; Neuilly, France); selective estrogen receptor modulators such as raloxifene (Evista®; Eli Lilly & Co.); and the like.

Examples of anti-inflammatory agents include, but are not limited to, steroids such as the glucocorticoids (e.g., cortisol, prednisone, prednislone and hydrocortisone.); non-steroidal anti-inflammatory agents such as acetaminophen, aspirin, ibuprofen, indomethacin, diclofenac, difenpiramide, fenbufen, flufenamic acid, ketoprofen, meclofenamate sodium, mefenamic acid, nabumetone, naproxen, piroxicam, suprofen and tiaprofenic acid; herbs having anti-inflammatory qualities such as hyssop, ginger, turmeric, *Arnica montana* (which contains helenalin, a sesquiterpene lactone), willow bark (which contains salicylic acid); and the like.

Examples of immunosuppressive agents include, but are not limited to, calcineurin inhibitors such as cyclosporine and tacrolimus; calcitonin gene-related peptide (see, U.S. Pat. Nos. 5,635,478 and 5,858,978, both of which are herein incorporated by reference); mTOR inhibitors such as sirolimus and everolimus; anti-proliferatives such as azathioprine and mycophenolic acid; corticosteroids such as prednisolone and hydrocortisone; antibodies such as monoclonal anti-IL-2Rα receptor antibodies (e.g., Basiliximab (Simulect®; Novartis Pharmaceutical Corp.; East Hanover, N.J.), and Daclizumab (Zenapax®; Hoffman-La Roche Inc.)); polyclonal anti-T-cell antibodies; anti-thymocyte globulin (ATG); anti-lymphocyte globulin (ALG); and the like.

Examples of chemotherapeutic agents include, but are not limited to, alkylating agents such as cisplatin, carboplatin, cyclophosphamide, chlorambucil, mechlorethamine and oxaliplatin; antibodies to tumor antigens; antimetabolites such as azathioprine and mercaptopurine; anthracyclines such as daunorubicin, doxorubicin, epirubicin, idarubicin and valrubicin; plant alkaloids such as podophyllotoxin, taxanes, vincristine, vinblastine, vinorelbine and vindesine; topoisomerase inhibitors such as type I topoisomerase inhibitors (e.g., amptothecins, irinotecan and topotecan) and type II topoisomerase inhibitors (e.g., amsacrine, etoposide, etoposide phosphate and teniposide); other antitumour agents such as dactinomycin, bleomycin and others; and the like.

Activation of Cell-Cell Fusion

In some instances, SK4 channel activity or function can be stimulated with an SK4 channel activator to promote cell fusion, especially in situations where it may be useful to have increased fused cells (osteoclasts). Such situations include patients with abnormally increased bone density, patients with a chronic infection or patients having osteopetrosis. Osteopetrosis, also known as marble bone disease and Albers-Schonberg disease, is a rare inherited disorder whereby bones harden and become denser. Patients with osteopetrosis tend to have bones that are more brittle than normal.

Examples of activators of SK4 channel activity or function include, but are not limited to, 1-ethyl-2-benzimidazolinone.

The invention includes compositions having an effective amount of an SK4 channel activator and optionally a therapeutic agent for treating a disease or disorder mediated by macrophage-derived multinucleate cells. In one embodiment, a composition is provided that comprises an effective amount of an SK4 channel activator and a therapeutic agent. In other embodiments, a pharmaceutical composition is provided that comprises a therapeutically effective amount of an SK4 activator and a therapeutic agent, as well as a pharmaceutically acceptable carrier.

As used herein, an "SK4 channel activator" or "SK4 channel activating agent" means agents that affect SK4 channel expression (i.e., translation or transcription), SK4 channel activity (i.e., conductance), or upstream and downstream SK4 channel effectors (i.e., promoter activators, inducers, suppressors, repressors, kinases, etc.) to promote SK4 channel activity. In some embodiments, the SK4 channel activator can be a protein designed to bind SK4 channels and modulate their function (i.e., ability to depolarize or repolarize). Alternatively, the SK4 channel activator can be a small molecule that specifically binds to SK4 channels and promotes their activity or function.

Regardless of the exact nature of the SK4 channel activator, it increases one or more of SK4 channel expression, activity or function. The expression, activity or function increases by a statistically significant amount including, but not limited to, about 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150% compared to an appropriate control. Preferably, the SK4 channel expression, activity or function increases by at least about 10% or more. Conversely, the SK4 channel activator should not statistically decrease SK4 channel expression, activity or function.

Pharmaceutical Compositions Comprising Inhibitors or Activators

When the composition is a pharmaceutical composition, it also can include a pharmaceutically acceptable carrier. As used herein, a "pharmaceutically acceptable carrier" means a material that is not biologically, physiologically, or otherwise undesirable, i.e., the material can be administered to a subject in a formulation or composition without causing any undesirable biological or physiological effects or interacting in a deleterious manner with any of the components of the composition in which it is contained.

The pharmaceutically acceptable carrier employed can be a solid, liquid, or gas. Examples of solid carriers include, but are not limited to, lactose, terra alba, sucrose, talc, gelatin, agar, pectin, acacia, magnesium stearate and stearic acid. Examples of liquid carriers include, but are not limited to, sugar syrup, peanut oil, olive oil, water and saline. Examples of gaseous carriers include, but are not limited to, carbon dioxide and nitrogen.

In addition to the pharmaceutically acceptable carrier, the pharmaceutical compositions can include, as appropriate, one or more additional additives such as diluents, buffers, flavoring agents, binders, surface-active agents, thickeners, lubricants, preservatives (including anti-oxidants), and the like. Moreover, other adjuvants can be included to render the formulation isotonic with the blood of the subject for intravenous administration.

Desired additives include, but are not limited to, pH control agents, such as arginine, sodium hydroxide, glycine, hydrochloric acid, citric acid, and the like. In addition, local anesthetics (e.g., benzyl alcohol), isotonizing agents (e.g., sodium chloride, mannitol or sorbitol), adsorption inhibitors (e.g., Tween® 80), solubility enhancing agents (e.g., cyclodextrins and derivatives thereof), stabilizers (e.g., serum albumin), reducing agents (e.g., glutathione) and preservatives (e.g., antimicrobials and antioxidants) can be included.

Pharmaceutical compositions for oral dosage can be prepared in any form known in the art. For example, water, glycols, oils, alcohols, flavoring agents, preservatives, coloring agents and the like may be used to form oral liquid preparations such as suspensions, elixirs and solutions, while carriers such as starches, sugars, microcrystalline cellulose, diluents, granulating agents, lubricants, binders, disintegrating agents and the like may be used to form oral solid preparations such as powders, capsules and tablets.

In tablets, the SK4 channel inhibitor or activator can be prepared by compression or molding, optionally with one or more accessory ingredients or adjuvants. Compressed tablets may be prepared by compressing, in a suitable machine, the SK4 channel inhibitor or activator in a free-flowing form such as powder or granules, optionally mixed with a binder, lubricant, inert diluent, surface active or dispersing agent, or other such excipient. These excipients can be, e.g., inert diluents such as calcium carbonate, sodium carbonate, lactose, calcium phosphate or sodium phosphate; granulating and disintegrating agents, e.g., corn starch or alginic acid; binding agents, e.g., starch, gelatin or acacia; and lubricating agents, e.g., magnesium stearate, stearic acid or talc. The tablets can be uncoated, or they can be coated by known techniques to delay disintegration and absorption in the gastrointestinal tract and thereby provide a sustained action over a longer time, especially for treating immune system disorders such as inflammatory bowel disease (IBD) or irritable bowel syndrome (IBS). For example, a time delay material such as glyceryl monostearate or glyceryl distearate can be used.

In hard gelatin capsules, the SK4 channel inhibitor or activator can be mixed with an inert, solid diluent, e.g., calcium carbonate, calcium phosphate or kaolin. Conversely, in soft gelatin capsules, the SK4 channel inhibitor or activator can be mixed with water or an oil medium, e.g., peanut oil, liquid paraffin or olive oil. Molded tablets can be made by molding in a suitable machine, a mixture of powdered SK4 channel inhibitor or activator moistened with an inert liquid diluent.

By way of example only, a pharmaceutical composition intended for oral administration to a human subject can contain from about 0.5 mg to about 5 g of the SK4 channel inhibitor or activator, compounded with an appropriate and convenient amount of pharmaceutically acceptable carrier that may vary from about 5% to about 95% of the total composition. Unit dosage forms will generally contain between from about 1 mg to about 2 g of the SK4 channel inhibitor or activator, typically about 25 mg, 50 mg, 100 mg, 200 mg, 300 mg, 400 mg, 500 mg, 600 mg, 700 mg, 800 mg, 900 mg or 1000 mg of the SK4 channel inhibitor or activator.

Pharmaceutical compositions for parenteral administration can be prepared as solutions or suspensions of the SK4 channel inhibitor or activator in water. A suitable surfactant can be included such as, e.g., hydroxypropylcellulose. Pharmaceutical compositions can also be prepared in glycerol, liquid polyethylene glycols and mixtures thereof in oils. Alternatively, the pharmaceutical compositions can be prepared in liposomes. See, e.g., Langer (1990) Science 249: 1527-1533; and Treat et al., 353-365 In: Liposomes in the Therapy of Infectious Disease and Cancer (Lopez-Berestein & Fidler eds., Liss, N.Y. 1989). Moreover, a preservative can be included to prevent the detrimental growth of microorganisms.

Likewise, pharmaceutical compositions for injection can be prepared as sterile aqueous solutions or dispersions. Alternatively, the compositions can be in the form of sterile powders for sterile injectable solutions or dispersions. The final injectable form must be sterile and must be effectively fluid for easy administration. The pharmaceutical compositions must be stable under the conditions of manufacture and storage and thus, preferably should be preserved against the contaminating action of microorganisms such as bacteria and fungi. As such, the pharmaceutically acceptable carrier can be a solvent or dispersion medium containing, e.g., water, ethanol, polyol (e.g., glycerol, propylene glycol and liquid polyethylene glycol), vegetable oils and suitable mixtures thereof.

By way of example only, a pharmaceutical composition intended for parenteral administration or injection to a human subject can contain from about 0.5 mg to about 5 g of the SK4 channel inhibitor or activator, compounded with an appropriate and convenient amount of pharmaceutically acceptable carrier that may vary from about 5% to about 95% of the total composition. Unit dosage forms will generally contain between from about 1 mg to about 2 g of the SK4 channel inhibitor or activator, typically about 25 mg, 50 mg, 100 mg, 200 mg, 300 mg, 400 mg, 500 mg, 600 mg, 700 mg, 800 mg, 900 mg or 1000 mg of the SK4 channel inhibitor or activator.

Pharmaceutical compositions for topical administration can be prepared, e.g., as an aerosol, cream, ointment, lotion, dusting powder or the like. Alternatively, the pharmaceutical compositions can be in a form suitable for use in transdermal devices. These pharmaceutical compositions may be prepared by methods well known in the art. For example, a cream or ointment can be prepared by admixing water, together with about 5 wt % to about 10 wt % of the binding agent, to produce a cream or ointment having a desired consistency.

By way of example only, a pharmaceutical composition intended for topical administration to a human subject can contain from about 0.5 mg to about 5 g of the SK4 channel inhibitor or activator, compounded with an appropriate and convenient amount of pharmaceutically acceptable carrier that may vary from about 5% to about 95% of the total composition. Unit dosage forms will generally contain between from about 1 mg to about 2 g of the SK4 channel inhibitor or activator, typically about 25 mg, 50 mg, 100 mg, 200 mg, 300 mg, 400 mg, 500 mg, 600 mg, 700 mg, 800 mg, 900 mg or 1000 mg of the SK4 channel inhibitor or activator.

Pharmaceutical compositions for rectal administration can be prepared with a solid pharmaceutically acceptable carrier. Preferably, the mixture forms unit dose suppositories. Suitable pharmaceutically acceptable carriers include cocoa butter and other thickening agents commonly used in the art. Suppositories can be conveniently formed by first admixing the composition with a softened or melted pharmaceutically acceptable carrier followed by chilling and shaping in molds.

By way of example only, a pharmaceutical composition intended for rectal administration to a human subject can contain from about 0.5 mg to about 5 g of the SK4 channel inhibitor or activator, compounded with an appropriate and convenient amount of pharmaceutically acceptable carrier that may vary from about 5% to about 95% of the total composition. Unit dosage forms will generally contain between from about 1 mg to about 2 g of the SK4 channel inhibitor or activator, typically about 25 mg, 50 mg, 100 mg, 200 mg, 300 mg, 400 mg, 500 mg, 600 mg, 700 mg, 800 mg, 900 mg or 1000 mg of the SK4 channel inhibitor or activator.

Pharmaceutical compositions for inhaled administration can be prepared in forms and utilizing carriers known in the art. See, e.g., Zeng et al., In: Particulate Interactions in Dry Powder Formulations for Inhalation (Informa HealthCare $1^{st}$ ed. 2000).

By way of example only, a pharmaceutical composition intended for inhaled administration to a human subject can contain from about 0.5 mg to about 5 g of the SK4 channel inhibitor or activator, compounded with an appropriate and convenient amount of pharmaceutically acceptable carrier that may vary from about 5% to about 95% of the total composition. Unit dosage forms will generally contain between from about 1 mg to about 2 g of the SK4 channel inhibiting binding agent, typically about 25 mg, 50 mg, 100 mg, 200 mg, 300 mg, 400 mg, 500 mg, 600 mg, 700 mg, 800 mg, 900 mg or 1000 mg of the SK4 channel inhibitor or activator.

The compositions and pharmaceutical compositions may include, in addition to the SK4 channel inhibitor or activator, one or more other therapeutic agents to treat an underlying disease or disorder, as discussed in greater detail below. Examples of other therapeutic agents for use herein include, but are not limited to, anti-inflammatory agents (i.e., steroidal and non-steroidal anti-inflammatory agents), anti-bone-loss agents and chemotherapeutics (i.e., alkylating agents, anti-metabolites, plant alkaloids and terpenoids and topoisomerase inhibitors).

The compositions and pharmaceutical compositions may include mutagenized macrophages that carry mutations in SK4 channel genes, where the mutations reduce or eliminate expression of the SK4 channel monomer or inhibit the activity of an encoded SK4 channel monomer.

With regard to the foregoing discussion of the compositions of the invention, the term "about" means within a statistically meaningful range of a value such as a stated concentration range, dosage amount, or amount of a component in a composition. Such a range can be within an order of magnitude, typically within 20%, more typically still within 10%, and even more typically within 5% of a given value or range. The allowable variation encompassed by the term "about" will depend upon the particular context in which the term is used, and can be readily appreciated by one of ordinary skill in the art.

Methods for Modulating Cell-Cell Fusion and Therapeutic and Screening Applications Thereof In some embodiments, the methods of the present invention comprise contacting macrophage cells with an effective amount of an SK4 channel inhibitor or activator, thereby decreasing or increasing macrophage cell fusion, respectively. As noted above, the SK4 channel inhibitor or activator can be one that affects SK4 channel expression (i.e., translation or transcription), SK4 channel activity (i.e., conductance), or upstream or downstream SK4 channel effectors (i.e., promoter activators, inducers, suppressors, repressors, kinases, etc.), so long as it effectively decreases or increases SK4 channel expression, activity, or function.

In inhibiting SK4 activity, without being bound by any theory or mechanism of action, the inhibitory effect of the SK4 channel inhibitor on SK4 channel expression, activity, or function within macrophage cells that have the potential to fuse, or are in the process of fusing, results in a decrease in macrophage cell fusion. By "potential to fuse" is intended the macrophage cells reside within an environmental setting that is conducive to macrophage cell fusion. For example, under in vitro conditions, such as would be used in a screening method (for example, the screening method described herein below), macrophage cells having a potential to fuse would include a population of macrophage cells that previously were not fusing but are now being exposed to fusogenic conditions (i.e., conditions that promote or foster macrophage cell fusion, as noted herein below). Under in vivo conditions, macrophage cells having a potential to fuse would include any population of previously non-fusing macrophage cells that becomes exposed to an in vivo environment that promotes or fosters macrophage cell fusion. Thus, macrophage cells having the potential to fuse may be stationary (i.e., fixed) macrophage cells located within the in vivo environment, or may be macrophages that are migrating into the in vivo environment. Similarly, under in vivo conditions, macrophage cells that are in the process of fusing can include stationary macrophages residing within an in vivo environment, and/or macrophages that are moving into an in vivo environment, where that environment promotes or fosters macrophage cell fusion.

Any of the SK4 channel inhibitors or activators described herein above can advantageously be used in the methods of the invention to decrease (i.e., inhibit) or increase macrophage cell fusion, either in an in vitro or in vivo setting. Where macrophage cell fusion is to be inhibited in an in vivo setting, the macrophage cells targeted for decreased cell fusion are contacted with a therapeutically effective amount of the SK4 channel inhibitor, where the therapeutically effective amount is determined by the desired outcome (e.g., treatment of a disease or disorder that is mediated by macrophage-derived multinucleate cells). Likewise, where macrophage cell fusion is to be increased or activated in an in vivo setting, the macrophage cells targeted for increased cell fusion are contacted with a therapeutically effective amount of the SK4 channel activator, where the therapeutically effective amount is determined by the desired outcome.

Thus, in some embodiments of the invention, the method for inhibiting macrophage cell fusion comprises providing an effective amount of an SK4 channel inhibitor to macrophage cells that have the potential to fuse, thereby preventing or reducing fusion of these cells. In other embodiments, the method for inhibiting macrophage cell fusion comprises providing an effective amount of an SK4 channel inhibitor to macrophage cells that are in the process of fusing, thereby preventing or reducing further fusion of these cells. The methods for inhibiting macrophage cell fusion can be aimed at stationary (i.e., fixed) macrophages, and/or macrophages migrating into a particular in vivo environment, and can be aimed at homotypic or heterotypic fusion of macrophages. Thus, these methods can target macrophage-macrophage cell fusion, such as occurs in the formation of osteoclasts (in bone) and giant cells (in multiple types of other tissues), or target macrophage fusion to other cell types, such as fusion between macrophage and cancer cells, which results in formation metastatic cancer cells.

In some embodiments, the effective amount of the SK4 channel inhibitor decreases macrophage cell fusion by at least about 10%, 15%, 20%, 25%, 30%, 35%, 40%, 45%, 50% or 55%, when compared to a suitable control sample, where the suitable control sample comprises comparable macrophage cells under the same environmental conditions in the absence of the SK4 channel inhibitor. In other embodiments, the effective amount of the SK4 channel inhibitor decreases macrophage cell fusion by at least about 55%, 60%, 65%, 70%, 75%, 80%, 85%, 90%, 95%, 96%, 97%, 98%, 99% or 100% (i.e., macrophage cell fusion is prevented), when compared to the suitable control sample. Methods to assay for macrophage cell fusion are well known in the art. See, e.g., Vignery (2000), supra; MacLauchlan et al. (2009) *J. Leukoc. Biol.* 85:617-626; and the assays described in the Experimental section herein below.

As noted herein above, inappropriate or unregulated (i.e., abnormal) macrophage cell fusion can be associated with cellular and tissue damage in inflammatory and infectious diseases. The method for inhibiting macrophage cell fusion described herein finds use in therapeutic methods aimed at prevention or treatment of diseases mediated by macrophage-derived multinucleate cells, including diseases related to abnormal osteoclast formation (e.g., osteoporosis), giant cell formation (e.g., chronic inflammatory diseases), and formation of metastatic cancer cells, which can trigger cancer metastasis.

As used herein, "prevent" or "preventing" and the like means an application or administration of an SK4 channel inhibitor to a subject, or the application or administration of a pharmaceutical composition comprising an SK4 channel inhibitor to a subject, where the subject has a predisposition toward a disease or medical condition, where the purpose is to keep the subject from developing the disease or medical condition. For example, an SK4 channel inhibitor, or a pharmaceutical composition comprising an SK4 channel inhibitor, could be administered to a subject whom is or will be undergoing an implant or transplant procedure, with the purpose of preventing rejection of the implant or transplant procedure. As another example, an SK4 channel inhibitor could be administered to a subject who is predisposed to developing osteoporosis, with the purpose of preventing excessive bone loss and development of osteoporosis.

In embodiments for the activation of an SK4 channel, the method comprises providing an effective amount of an SK4 channel activator to macrophage cells to increase fusion of the cells. The methods for activating macrophage cell fusion can be aimed at stationary macrophages, and/or macrophages migrating to a particular in vivo environment and can be aimed at homotypic or heterotypic fusion of macrophages. The effective mount of the SK4 channel activator increases macrophage cell fusion by at least about 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, or 150% when compared to a suitable control. Methods to assay for macrophage cell fusion are known as disclosed above.

As used herein, "treating" or "treatment" means an application or administration of an SK4 channel inhibitor or activator to an individual, or the application or administration of a pharmaceutical composition comprising an SK4 channel inhibitor or activator to a subject, where the subject has a disease or a symptom of a disease, where the purpose is to cure, heal, alleviate, relieve, alter, remedy, ameliorate, improve or affect the disease or symptoms of the disease.

In some embodiments of the invention, the method for inhibiting macrophage cell fusion is directed to inhibition of osteoclast formation in vivo, with a therapeutic objective of preventing or treating bone loss. By inhibiting osteoclast formation, osteoclast numbers and/or osteoclast surface area are decreased, resulting in an overall decrease in osteoclast function, as noted herein above. Furthermore, by inhibiting SK4 expression, activity or function of osteoclasts, function of osteoclasts can be altered, for example, decreasing osteoclast bone mineral resorption activity. By decreasing osteoclast formation and function, bone density and/or bone thickness can be favorably increased, In this manner, the present invention provides a method for preventing or treating bone loss in a subject susceptible to or having bone loss, where the method comprises administering to the subject a therapeutically effective amount of an SK4 channel inhibitor to inhibit osteoclast formation, thereby preventing or decreasing the subject's bone loss. This method of therapy finds use in maintaining bone density in a subject susceptible to or having bone density loss. In a related embodiment, the method for preventing or treating bone loss can include combination therapy with at least one anti-bone-loss agent. Routes of administration of the SK4 channel inhibitor, and the anti-bone-loss agent(s), will be affected by the underlying cause of the predisposition for bone loss or the actual bone loss, but can be orally, intravenously, and even by direct delivery to the bone.

Exemplary conditions where the methods of the present invention can be used to prevent or treat bone loss in a subject include, but are not limited to, osteoporosis, osteomalacia, Paget's disease, periodontal disease and bone loss secondary to other pathological conditions (i.e., alcoholism, celiac disease, chronic kidney disease, chronic liver disease, epilepsy, gastrointestinal disease, hyperthyroidism, hypogonadism, leukemia, lymphoma, rheumatoid arthritis, scurvy and vitamin D deficiency), and the like.

In other embodiments of the invention, the method for inhibiting macrophage cell fusion is directed to inhibition of giant cell formation in vivo, with a therapeutic objective of preventing or treating an autoimmune or inflammatory disease or disorder in a subject. In this manner, the present invention provides a method for preventing or treating an autoimmune or inflammatory disease or disorder in a subject susceptible to or having such a disease or disorder, where the method comprises administering to the subject a therapeutically effective amount of an SK4 channel inhibitor to inhibit giant cell formation, thereby preventing or treating the autoimmune or inflammatory disease or disorder in the subject. In a related embodiment, the method for preventing or treating the autoimmune or inflammatory disease or disorder can include combination therapy with at least one anti-inflammatory agent. Routes of administration of the SK4 channel inhibitor, and the anti-inflammatory agent(s), will be affected by the underlying cause of the predisposition for the autoimmune or inflammatory disease or disorder, or the actual autoimmune or inflammatory disease or disorder, but can be orally, intravenously, topically, and even by direct injection, for example, to the site of inflammation.

Exemplary conditions where the methods of the present invention can be used to prevent or treat an autoimmune disease or disorder include, but are not limited to, acute disseminated encephalomyelitis (ADEM), Addison's disease, alopecia, ankylosing spondylitis, antiphospholipid antibody syndrome, autoimmune inner ear disease, autoimmune hemolytic anemia, autoimmune hepatitis, Chagas disease, chronic obstructive pulmonary disease, celiac disease, Crohns Disease, dermatomyositis, diabetes mellitus type 1, endometriosis, Goodpasture's syndrome, Graves' disease, Guillain-Barré syndrome (GBS), Hashimoto's disease, Kawasaki disease, idiopathic thrombocytopenic purpura, systemic lupus erythematosus, multiple sclerosis (MS), myasthenia gravis, psoriasis, primary biliary cirrhosis, rheumatoid arthritis, scleroderma, Sjögren's syndrome, temporal arteritis (also known as "giant cell arteritis"), ulcerative colitis, vasculitis, and the like. Exemplary conditions where the methods of the present invention can be used to prevent or treat an inflammatory disease or disorder include, but are not limited to, acne, asthma, arthrosclerosis, chromic obstructive pulmonary disease, colitis, dermatitis, glomerulonephritis, inflammatory bowel disease, keloid, nephritis, osteoarthritis, pelvic inflammatory disease, psoriasis, rheumatoid arthritis, tendinitis, and the like.

In other embodiments of the invention, the method for inhibiting macrophage cell fusion is directed to inhibition of giant cell formation in vivo, with a therapeutic objective of preventing implant or transplant rejection in a subject. In this manner, the present invention provides a method for preventing implant or transplant rejection in a subject who is or will be undergoing an implant or transplant procedure, where the method comprises administering to the subject a therapeutically effective amount of an SK4 channel inhibitor to inhibit giant cell formation, thereby preventing rejection of the implant or transplant. In a related embodiment, this method of therapy can include combination therapy with at least one immunosuppressant agent. Where applicable, either of these methods can include combination therapy with at least one anti-bone-loss agent, for example, where an implant is directed to therapy for a bone-related disease or disorder. Routes of administration of the SK4 channel inhibitor, and the immunosuppressant agent(s) and/or anti-bone-loss agent(s), will be affected by the type of implant or organ/tissue transplant but can be orally, intravenously, topically, by direct delivery, or by coating or impregnating the implant.

Exemplary implants for which the methods of the invention can be used to prevent rejection include, but are not limited to, a cochlear device, artificial knee joint, artificial hip joint, bone cement, breast implant, cardiac implant (e.g., artificial heart valves, defibrillators, left-ventricular assist devices and pacemakers), dermal implant, gastric band or balloon, indwelling catheter, insulin pump, intrauterine device, neurological stimulator, ophthalmic implant, orthopedic implant, penile erectile prosthesis, stent, urethral sling, voice prosthesis, and the like. Exemplary transplants for which the methods of the invention can be used to prevent rejection include, but are not limited to, bone and bone marrow transplant, corneal transplant, heart and heart valve transplant, intestine transplant, kidney transplant, limb transplant, liver transplant, lung transplant, pancreas transplant, platelet transfusion, red blood cell transfusion, skin transplant, stem cell transplant, tendon transplant, vascular transplant, white blood cell transfusion, and the like.

In other embodiments of the invention, the method for inhibiting macrophage cell fusion is directed to inhibition of metastatic cell formation in vivo, with a therapeutic objective of preventing cancer metastasis in a subject. In this manner, the present invention provides a method for preventing cancer metastasis in a subject predisposed to development metastatic cancer, where the method comprises administering to the subject a therapeutically effective amount of an SK4 channel inhibitor to inhibit metastatic cancer cell formation, thereby preventing cancer metastasis. In a related embodiment, this therapeutic method can include combination therapy with at least one other form of anti-cancer therapy, e.g., surgery or a surgical procedure, or administration of another anti-cancer therapeutic agent, e.g., a chemotherapeutic agent, an anti-cancer antibody, small molecule-based cancer therapy or vaccine/immunotherapy-based cancer therapy. Routes of administration of the SK4 channel inhibitor, and if administered, the other anti-cancer therapeutic agent(s), will be affected by the type and location of the primary tumor and potential site of metastasis but can be orally, intravenously, topically, or by direct delivery to the primary tumor.

Exemplary cancers for which the methods of the invention can be used to prevent metastasis include, but are not limited to, bone cancer, brain cancer, breast cancer, cervical cancer, colon cancer, intestinal cancer, liver cancer, lung cancer, pancreatic cancer, prostate cancer, rectal cancer, stomach cancer, throat cancer, uterine cancer, and the like.

Depending upon the disease or disorder undergoing treatment, clinical response to an SK4 channel inhibitor, or an SK4 channel activator, alone or in combination with another therapeutic agent or regimen, can be assessed using any acceptable method known in the art, including, but not limited to, screening techniques such as magnetic resonance imaging (MRI) scan, x-radiographic imaging, micro CT, computed tomographic (CT) scan, bioluminescent imaging, for example, luciferase imaging, bone scan imaging, tumor biopsy sampling including bone marrow aspiration (BMA), flow cytometry or fluorescence-activated cell sorter (FACS) analysis, histology, gross pathology and blood chemistry, including but not limited to, changes detectable by ELISA, RIA, chromatography, and the like.

In any of the therapeutic methods described above, the therapeutically effective amount of the SK4 channel inhibitor or activator can be administered at about the same therapeutically effective amount (i.e., dose) throughout a treatment period, in an escalating dose regimen or a loading-dose regime (for example, in which the loading dose is greater than the maintenance dose). Alternatively, the therapeutically effective amount of the SK4 channel inhibitor or activator can be varied during the course of a treatment based on the condition of the subject being treated, the apparent response to the therapy and/or other factors as judged by one of skill in the art. Long-term treatment with the therapeutically effective amount of the SK4 channel inhibitor or activator is also contemplated.

Furthermore, where the methods of the present invention comprise combined therapeutic regimens, these therapies can be given simultaneously, i.e., the SK4 channel inhibitor or activator is administered concurrently with the other therapeutic regimen or within the same time frame as the other therapeutic regimen (i.e., the therapies are going on concurrently, but the SK4 channel inhibitor or activator is not administered precisely at the same time as the other therapy). Alternatively, the SK4 channel inhibitor or activator may also be administered prior to or subsequent to the other therapy. Where combination therapy comprises concurrent administration of an SK4 channel inhibitor or activator and at least one other therapeutic agent, the SK4 channel inhibitor or activator and the other therapeutic agent(s) can be administered as separate pharmaceutical compositions, or formulated together and administered as a single pharmaceutical composition.

Moreover, administration of the SK4 channel inhibitor or activator can begin when the subject is diagnosed or is suspected of having the disease or disorder. Acceptable therapeutically effective amounts of the SK4 channel inhibitor or activator are discussed above and will vary depending upon the age and weight of the subject, the particular disease or disorder being treated, the severity of the disease or disorder being treated, and the route of administration. The therapeutic methods of the invention may comprise a single administration of a therapeutically effective amount of an SK4 channel inhibitor or activator, or multiple administrations of a therapeutically effective amount of the SK4 channel inhibitor or activator.

To be clear, the subjects for treatment in accordance with the methods of the present invention are not intended to be subjects having asthma or sickle cell disease.

The present invention also provides methods for identifying agents that inhibit cell-cell fusion via inhibition of the expression, activity, or function of an intermediate-conductance calcium-activated potassium channel (SK4 channel) or for identifying agents that activate cell-cell fusion. The method comprises contacting a cell population with a candidate SK4 channel inhibitor or activator and determining whether the candidate agent inhibits or activates cell-cell fusion within the cell population. Of particular interest is the identification of SK4 channel inhibitors that inhibit macrophage cell fusion, and thus inhibit formation of macrophage-derived multinucleate cells, including, but not limited to, osteoclasts, giant cells and metastatic cancer cells. Thus, in some embodiments, the population of cells comprises macrophage cells; in other embodiments, the population of cells comprises at least two cell types, one of which is macrophages. In some embodiments, the population of cells comprises macrophages and the second type of cell present within the population is somatic or cancer cells. See, Vignery, "Methods to fuse macrophages in vitro," 383-395 In: Methods in Molecular Biology, Cell Fusion (Chen ed., Humana Press 2008); incorporated herein by reference as if set forth in its entirety.

Preferably this screening method is carried out under fusogenic conditions. As used herein, "fusogenic conditions" means conditions that foster homotypic or heterotypic fusion of cells, especially macrophages. Fusogenic conditions can include culturing cells in the presence of M-CSF, RANKL and/or IL-4.

The invention will be more fully understood upon consideration of the following non-limiting Examples.

EXPERIMENTAL

Genome-wide cDNA microarrays were used to identify genes belonging to the fusion machinery and identified KCNN4/SK4 as highly expressed in osteoclast and giant cells, but only at the onset of fusion of macrophages.

Materials and Methods

Animals and cells. sk4$^{-/-}$ mice were generated on a mixed 129J/C57BL6 background, bred, and genotyped as previously described (Begenisich et al. (2004) J. Biol. Chem. 279(46):47681-47687). The animals were housed in standard caging on a 12-hour light cycle and were offered free access to rodent chow (Harlan Teklad #2018) and water. Mice were euthanized at 8 weeks of age. Mice received two i.p. injections of calcein (5 mg/kg/day) on day eight and one before sacrifice for dynamic histomorphometry analysis.

Reagents. MSC-F and RANKL were purchased from PreproTech (Rocky Hill, N.J.). Phalloidin-Alexa fluor 568 was purchased from Invitrogen (Carlsbad, Calif.) and osteologic slides from BD (Franklin Lakes, N.J.). All supplies and reagents for tissue culture were endotoxin-free. Unless otherwise stated, all chemicals were from Sigma Chemical Co. (St Louis, Mo.).

Chronic inflammatory arthritis (CIA). CIA was induced in two-month old mice by intraperitoneal injection of 7 mg (700 µl) of Arthrogen CIA monoclonal antibodies (ArthoMAB) blend (Millipore; Billerica, Mass.) on day 0. This cocktail of monoclonal antibodies is directed against epitopes recognized in the region CB11 of collagen type II. On day 3, 50 µg (<100 µl volume) of lipopolysaccharide (LPS) was administered intraperitoneally. Beginning on day 4, the animals were monitored daily for the onset and development of CIA, and the injection site on each animal was evaluated for signs of infection such as, heat, redness, and/or exudation. Mice that felt as "cold," which likely underwent cachexia in response to LPS, received 500 µl s.c. (subcutaneous) of warm Ringer solution. Arthritic severity was monitored daily using a visual scoring system. The scoring system is 0=normal; 1=erythema and edema in 1-2 digits; 2=erythema and edema in >2 digits or mild erythema and edema, usually in the ankle joint; 3=moderate erythema and edema encompassing the tarsal joint; 4=severe erythema and edema encompassing the tarsal and metatarsal joint.

Histopathology evaluation of CIA. Formalin-fixed joints (right and left fore and hind paws, both ankles and both knees) were decalcificied in 5% formic acid for 2-3 days; tissues were trimmed, processed for paraffin embedding, sectioned at 8 µm and stained with toluidine blue. Both hind paws, both fore paws, and both knees were embedded and sectioned in the frontal plane while ankles were sectioned in the sagital plane or ankles may be sectioned with hind paws in the frontal plane. All sections were scored without knowledge of the treatment groups. Groups were later identified as follows. When scoring paws or ankles from mice with arthritic lesions, severity of changes as well as number of individual joints affected must be considered. When only 1-3 joints of the paws or ankles out of a possibility of numerous metacarpal/metatarsal/digit or tarsal/tibio-tarsal joints were affected, an arbitrary assignment of a maximum score of 1, 2 or 3 for parameters below was given depending on severity of changes. If more than 3 joints were involved, the criteria below were applied to the most severely affected/majority of joints. Inflammation: 0=Normal; 1=Minimal infiltration of inflammatory cells in synovium and periarticular tissue of affected joints; 2=Mild infiltration of inflammatory cells. If referring to paws, generally restricted to affected joints (1-3 affected); 3=Moderate infiltration with moderate edema. If referring to paws, restricted to affected joints, generally 3-4 joints+wrist or ankle; 4=Marked infiltration affecting most areas with marked edema, 1 or 2 unaffected joints may be present; 5=Severe diffuse infiltration with severe edema affecting all joints and periarticular tissues. Pannus: 0=Normal; 1=Minimal infiltration of pannus in cartilage and subchondral bone, marginal zones; 2=Mild infiltration with marginal zone destruction of hard tissue in affected joints; 3=Moderate infiltration with moderate hard tissue destruction in affected joints; 4=Marked infiltration with marked destruction of joint architecture, affecting most joints; 5=Severe infiltration associated with total or near total destruction of joint architecture, affects all joints. Cartilage Damage: 0=Normal; 1-Minimal-generally minimal to mild loss of toluidine blue staining with no obvious chondrocyte loss or collagen disruption in affected joints; 2=Mild=generally mild loss of toluidine blue staining with focal areas of chondrocyte loss and/or collagen disruption in some affected joints; 3=Moderate=generally moderate loss of toluidine blue staining with multifocal chondrocyte loss and/or collagen disruption in affected joints, some matrix remains on any affected surface with areas of severe matrix loss; 4=Marked=marked loss of toluidine blue staining with multifocal marked (depth to deep zone) chondrocyte loss and/or collagen disruption in most joints, if knee-one surface with total to near total cartilage loss; 5=Severe=severe diffuse loss of toluidine blue staining with multifocal severe (depth to tide mark) chondrocyte loss and/or collagen disruption in all joints, if knee-2 or more surfaces with total to near total cartilage loss. Bone Resorption: 0=Normal; 1=Minimal=small areas of resorption, not readily apparent on low magnification, rare osteoclasts in affected joints, restricted to marginal zones; 2=Mild=more numerous areas of resorption, not readily apparent on low magnification, osteoclasts more numerous in affected joints, restricted to marginal zones; 3=Moderate=obvious resorption of medullary trabecular and cortical bone without full thickness defects in cortex, loss of some medullary trabeculae, lesion apparent on low magnification, osteoclasts more numerous in affected joints; 4=Marked=Full thickness defects in cortical bone, often with distortion of profile of remaining cortical surface, marked loss of medullary bone, numerous osteoclasts, affects most joints; 5=Severe=Full thickness defects in cortical bone and destruction of joint architecture of all joints. For each animal, the inflammation, pannus, cartilage damage and bone damage scores were determined for each of the 8 joints submitted. A sum total (all 8 joints) animal score and an eight joint mean animal score was determined as well as sums and means for each of the individual parameters. Parameters for the various groups were then compared to Group A (vehicle) using a Student's t test or other appropriate analysis method with significance set at p≤0.05.

Figure 13:
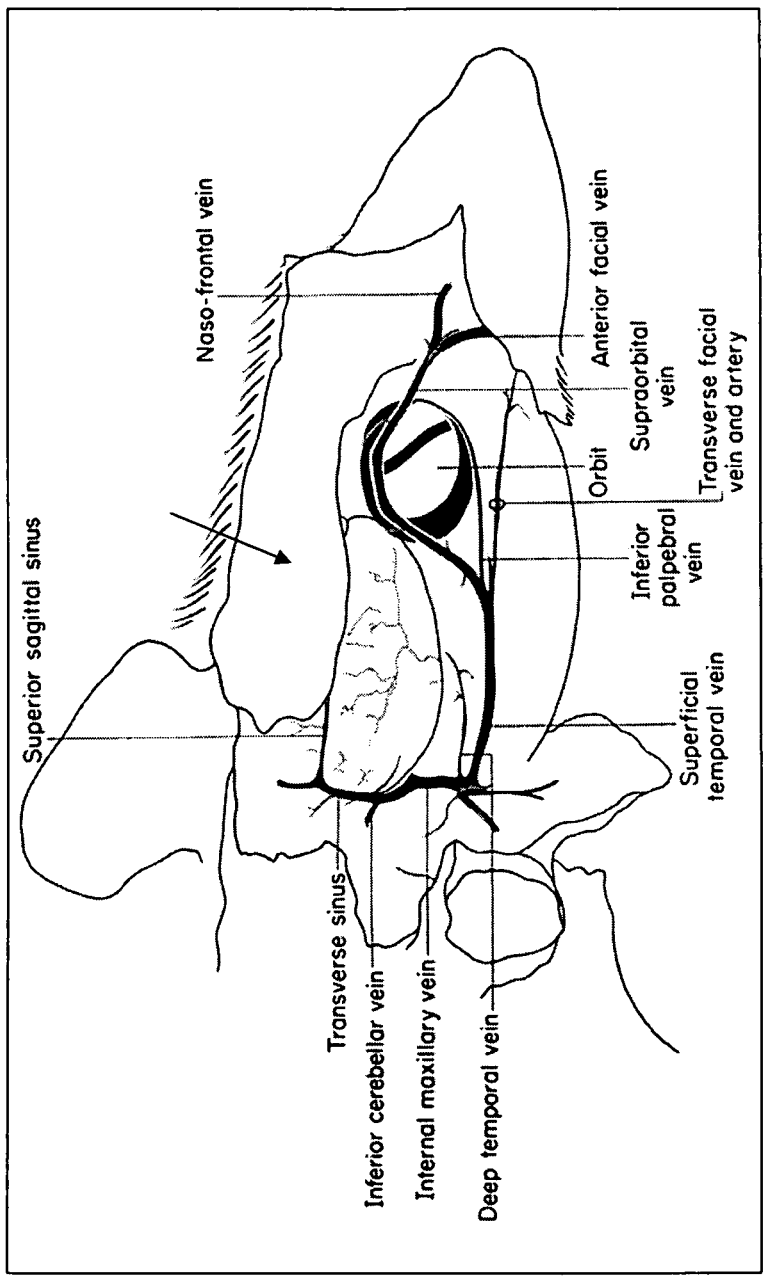
FIG. 13 shows a dorsolateral dissection of a mouse head. The arrow indicates the site of local subcutaneous injection of lipolysaccharide (LPS) above the calvarium in an in vivo osteoclast formation assay. This injection of LPS induces a localized, rapid and efficient inflammatory response that leads to the formation of osteoclasts that resorb bone.
Figure 15A:
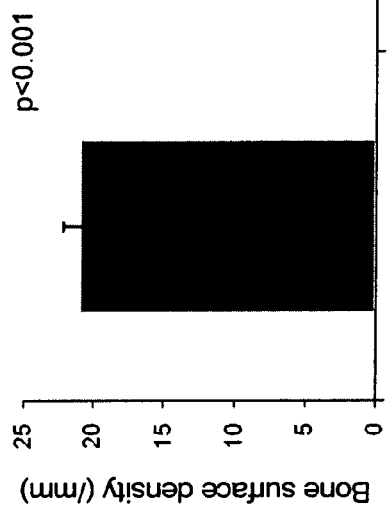
FIGS. 15A-C show the in vivo response of 3D parameters of calavariae of sk4$^{+/+}$ versus SK4-deficient (sk4$^{-/-}$) in response to local subcutaneous injection of LPS above the calvarium. Calvaria bone surface density (bone surface area relative to bone volume, FIG. 15A); bone thickness (FIG. 15B); and bone density (FIG. 15C). SK4-deficient mice maintain a higher calvaria bone thickness and density 5 days after LPS injection and a lesser resorbed bone surface.
Figure 15B:
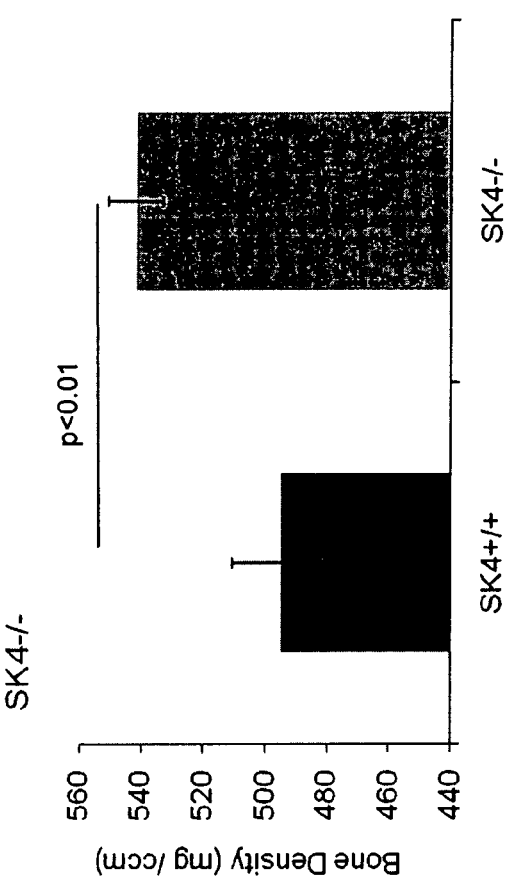
Figure 15C:
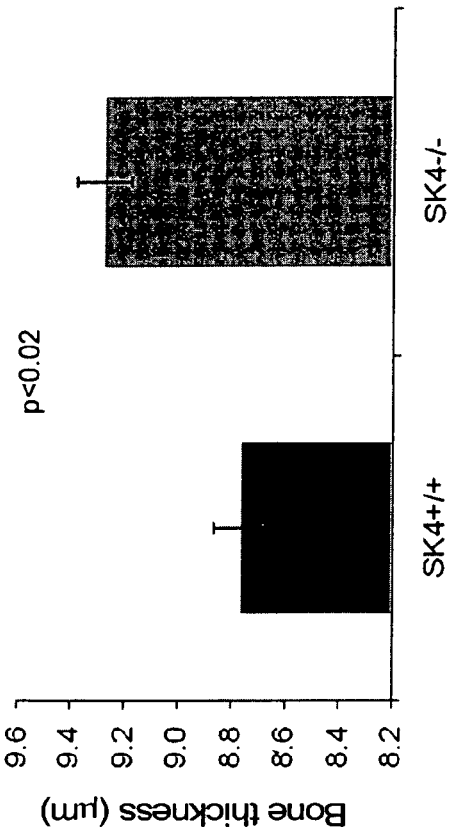

Calvarial LPS/in vivo bone resorption assay. To assess osteoclast formation and activity in vivo, a single local subcutaneous calvarial injection of lipopolysaccharide (25 μg in 2 μl; Sigma) was administered (see FIG. 13). Mice were sacrificed 5 days later, and calvariae subjected to microCT, then histomorphometry analysis to record the percentage of eroded bony surface per calvaria/mouse, the density and the thickness of the calvariae. Animals were checked daily for the five-day duration of the experiment, including weekends and holidays, if applicable. Those animals showing evidence of pain (e.g., inappetance, lethargy, isolation from cage mates as a result of expected adverse effects, if any, from administration of LPS, which can induce fever and loss of weight), analgesics were administered based on consultation with a veterinarian.

Bone radiography. Excised femurs were subjected to X-ray using a MX-20 (Faxitron X-ray Corporation, Wheeling, Ill.) at 30 kV for 3 seconds. X-rays were scanned using an Epson Perfection 4870.

Bone density and microarchitecture. Bone density was determined as described previously (Ballica et al. (1999) *J. Bone Mineral Res.* 14:1067-1074) by peripheral quantitative computed tomography (pQCT; XCT Research M; Norland Medical Systems, Fort Atkinson, Wis.) of a virtual 1 mm cross section of the distal femur 0.25 mm proximal to the growth plate. In addition, distal femurs were scanned with a microCT scanner (MicroCT 40; Scanco, Bassersdorf, Switzerland) with a 2,048×2,048 matrix and isotropic resolution of 9 μm$^3$ with 12 μm voxel size. Three-dimensional trabecular measurements in the secondary spongiosa were made directly, as previously described (Li et al. (2005) *J. Exp. Med.* 201:1169-1177).

DNA microarray. Total RNA from cell samples was isolated using a RNeasy® Kit (Qiagen; Hilden, Germany) and used for microarray hybridization using genechips from Affymetrix (Santa Clara, Calif.). Total RNA was used to synthesize cRNA using the Affymetrix expression protocol. 10 μg of labeled and fragmented cRNA was hybridized to HG-U133Plus2.0 Arrays or RAT230 Plus Arrays, and signal detection was performed according to the manufacture's instructions.

Histomorphometry. Femurs and tiboiae from sk4$^{+/+}$ and sk4$^{-/-}$ mice were dehydrated in a graded ethanol series and embedded without decalcification in methylmethacrylate, as we described previously (Baron et al. (1982) in *Bone Histomorphometry: Techniques and Interpretation*, ed. Recker et al. (CRC Press, Inc., Boca Raton, Fla.), pp. 13-35). Four-μm-thick cross sections of the distal femur 0.25 mm proximal to the growth plate were stained with Villanueva Mineralized Bone Stain for static histomorphometric analysis, while 8-μm-thick sections were left unstained for analysis of dynamic parameters. Histomorphomery was performed using Osteomeasure software (Osteometrics, Atlanta, Ga.). The following parameters were measured: the relative tissue surface occupied by bone (B.Ar/T.Ar; %); the number of trabeculae per mm (Tb.N/mm); the relative surface of bone occupied by trabeculae (Tb.Ar; %); the distance/separation between trabeculae (μm); the number of osteoclasts per total bone surface (Oc/T.Ar); the perimeter of osteoclasts per total bone perimeter (Oc.Pm./B.Pm); the perimeter of osteoblasts per total bone perimeter (Ob.Pm/B.Pm), mineralizing surface (MS/BS), mineral apposition rate (MAR), and bone formation rate (BFR/BV).

Bone marrow- and spleen-derived mouse osteoclasts. These cells were generated from four- to twelve-week-old sk4$^{+/+}$ and sk4$^{-/-}$ mice as previously described (Cui et al. (2007) *Proc. Natl. Acad. Sci. USA* 104:14436-14441; Epub 2007 Aug. 28). Bone marrow and spleen cells were isolated, mechanically dissociated and cultured at a density of 1.33× 10$^6$ cells per cm$^2$ in MEM containing 10% heat-inactivated fetal bovine serum (HyClone, Logan, Utah), 100 units/ml penicillin-streptomycin (Gibco Invitrogen, Carlsbad, Calif.), 1% MEM vitamins, 1% glutamine, and 30 ng/ml M-CSF (PeproTech, Inc. Rocky Hill, N.J.). RANKL (PeproTech, Inc.) was added at a concentration of 40 ng/ml. Media was changed every three days. To assess the formation of an actin ring, a landmark of osteoclast activity, cells were cultured in the presence of M-CSF (20 ng/ml) and RANKL (40 ng/ml)

on glass slides for 8 days, fixed and reacted with phalloidin-Alexa 568 and Topro-3. To further assess resorptive activity, cells were cultured on Osteologic slides that are coated with artificial bone made of calcium-phosphate crystals. After 8 days, cells were lysed and the substrates stained with silver nitrate according to the supplier's instructions. The resorbed areas on slides were recorded by histomorphometry.

Human osteoclasts. These cells were generated using normal peripheral blood blood (Allcells, Emeryville, Calif.). Peripheral blood monocytes were isolated using Ficoll-Paque and cultured at a concentration of $3 \times 10^6$ cells/ml in MEME supplemented with 10% FCS, recombinant human M-CSF (25 ng/ml) and recombinant human RANKL (40 ng/ml). The medium was changed once a week.

Western blot analysis. After seven days of culture, osteoclasts were serum-starved for two hours and stimulated with the indicated reagents. The cells were then lysed in Laemmli sample buffer supplemented with protease inhibitors (Complete Tablets; Roche Molecular Biochemicals), sodium fluoride, and a phosphatase inhibitor cocktail II. The lysates were sonicated and resolved by SDS-PAGE, transferred to Immobilon-P membranes, and subjected to immunoblotting using enhanced chemiluminescence (Amersham Pharmacia Biotechnology; Sunnyvale, Calif.).

Flow Cytometry. Cells were stained with the first antibody, incubated for 30 min on ice, and washed twice with washing buffer (5% FCS/PBS). The secondary antibody was added, and the cells were incubated for 30 min on ice. After incubation, cells were washed twice with washing buffer and suspended in washing buffer for FACS analysis, which was performed using a FACS Calibur (BD Bioscience; Franklin Lakes, N.J.).

Real time Reverse transcriptase polymerase chain reaction (real time-PCR). Total RNA was extracted in Trizol (Invitrogen; Carlsbad, Calif.) according to manufacturer instruction. First-strand cDNA was synthesized using 1 μg of the total RNA and Moloney murine leukemia virus reverse transcriptase. Primer pairs for the PCR reactions are provided in Table 2.

TABLE 2

PCR Primers for RT-PCR Studies.

| Gene | Forward Primer | Reverse Primer |
|---|---|---|
| SK4 | GCTCAACCAAGTCCGCTTCC (SEQ ID NO: 8) | CAATGGTCAGGAATGTGATCG[1] (SEQ ID NO: 9) |
|  | GGAACTGGCATCGGACTCAT (SEQ ID NO: 10) | CTGGACCTCCTTGGCATGGAA[2] (SEQ ID NO: 11) |
| GAPDH | AATGTGTCCGTCGTGGATCT (SEQ ID NO: 12) | CCCTGTTGCTGTAGCCGTAT (SEQ ID NO: 13) |

[1]Located between exon 2 and exon 3.
[2]Located between exon 1 and exon 2.

Statistical analysis. Data represent the mean±one standard deviation (SD). Treatment groups were compared using the analysis of variance. Pairwise comparison p-values between the treatment groups were adjusted using Tukey multiple comparison procedure. Statistical significance was declared if the two-sided p-value is <0.05. All computations were performed using SPSS.

Results

In Vitro Macrophage Fusion Assay.

Figure 1B:
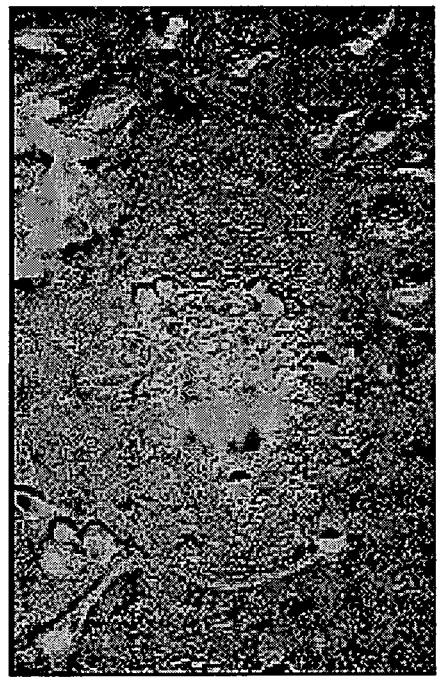
FIG. 1B shows a photograph of a multinucleate cell formed from fused rat alveolar macrophages after five days of culture under fusogenic conditions.

Freshly isolated rat alveolar macrophages appeared as multiple and distinct cells (FIG. 1A). After three days of culture under the fusogenic conditions (i.e., in the presence of M-CSF and RANKL, the macrophages fused into multinucleate cells (FIG. 1B). Advantageously, this assay resulted in little donor variation and did not show any RANKL stimulation effects.

Intermediate-Conductance Calcium-Activated Potassium Channel Expression is Upregulated During Rat Osteoclastogenesis.

Figure 2:
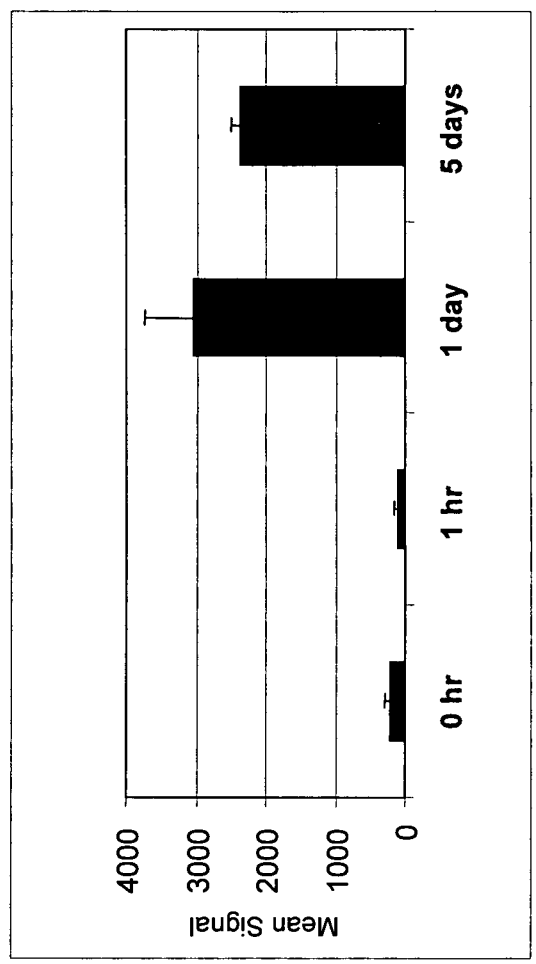
FIG. 2 shows upregulation of SK4 channel mRNA expression by 24 hours in rat alveolar macrophages under fusogenic conditions, which lasted through day 5 (x-axis represents replicate alveolar macrophage samples at 0 hour, 1 hour, 24 hours or 120 hours). Data are presented as mean signals (+ standard deviation) of three individual samples and were obtained by Affymetrix® Genechip® RAT230 Plus Array experiments (Probe ID 1368930_at).

SK4 channel message in fusing rat alveolar macrophages was unchanged after one hour, but was significantly increased after 24 hours (FIG. 2) and remained elevated for up to 5 days when compared to 0 hour-treated macrophages.

Intermediate-Conductance Calcium-Activated Potassium Channel Expression is Upregulated During Human Osteoclastogenesis.

These results demonstrate that human macrophages/PBMCs can be used in the macrophage fusion assay described above and that SK4 channel expression was upregulated in fusing macrophages/PBMCs.

Figure 3A:
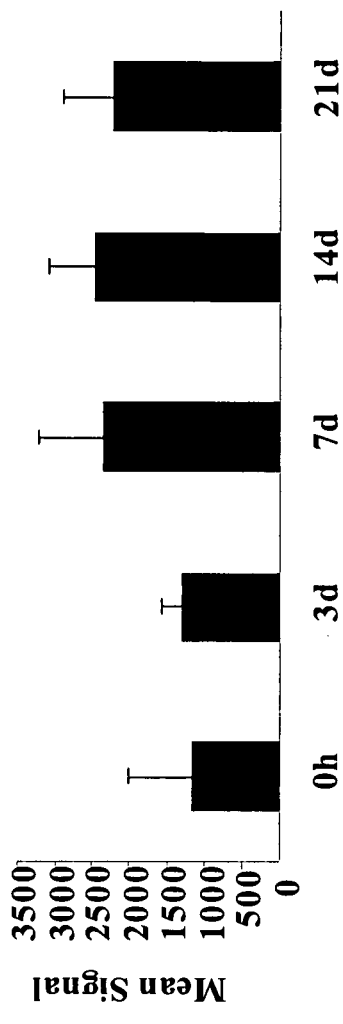
FIG. 3A shows upregulation of SK4 channel expression during differentiation of human peripheral blood mononuclear cells (PBMCs) to osteoclasts under M-CSF and RANKL stimulation (x-axis represents replicate human PBMC samples at 0 hour, 3 days, 7 days, 14 days or 21 days). Data are presented as mean signals (+ standard deviation) of four individual samples and were obtained by Affymetrix® Genechip® U133 Plus 2 Array chips.
Figure 3B:
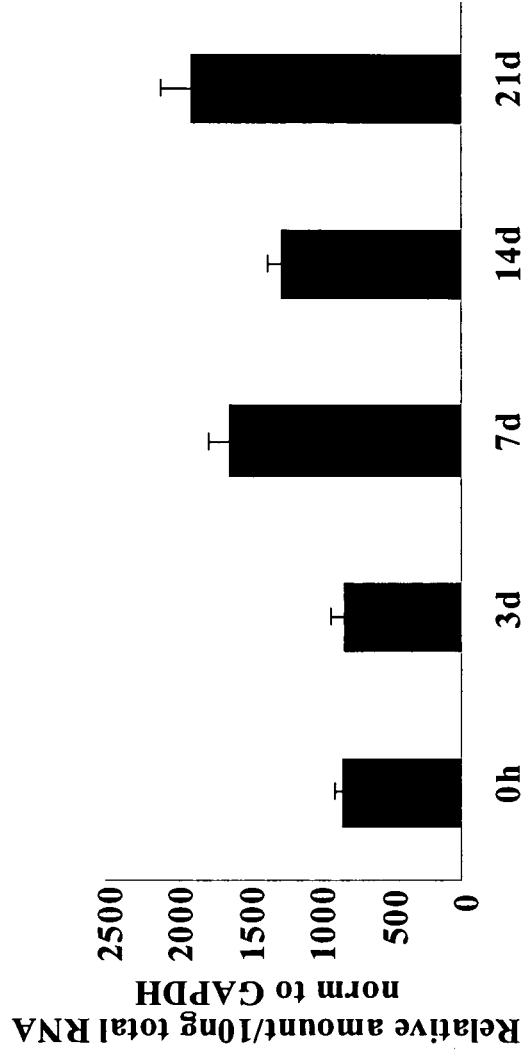
FIG. 3B shows that the Genechip® data were further confirmed by TaqMan® Real-Time RT-PCR (x-axis represents replicate human PBMC samples at 0 hour, 3 days, 7 days, 14 days or 21 days).
Figure 3C:
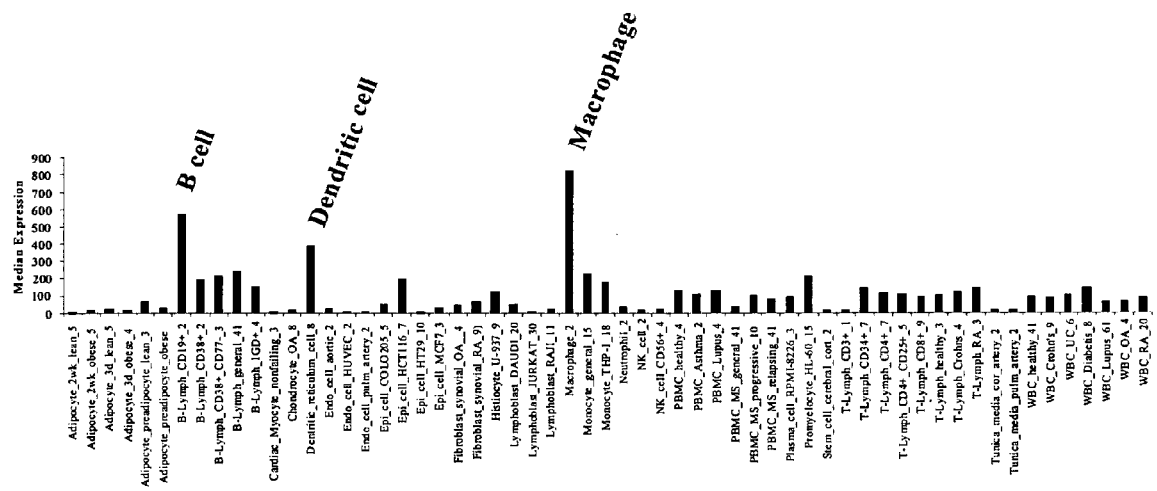
FIG. 3C shows high mRNA expression of SK4/IK in human B-cells, dendritic cells and macrophages as compared to other cells. Data from FIG. 3C were derived from Affymetrix® Genechip® RAT230 Plus Array chips and are presented as mean signals of the cell sample. The cells sampled with the number of replicates are indicated in FIG. 3C.

Freshly isolated human macrophages/PBMCs appeared as multiple and distinct cells and fused into osteoclasts. SK4 (SK4) channel expression increased after 7 days of culture under fusogenic conditions and remained increased until day 21 when measured by the Affymetrix® U133 Plus 2.0 GeneChip® (FIG. 3A) and TaqMan® Gene Expression System (FIG. 3B). An evaluation of SK4 channel expression in other blood cells and blood-related cells showed significantly increased expression in B-cells and dendritic cells (FIG. 3C). Therefore, human cells, like rat cells, show an increase in SK4 channel expression under fusogenic conditions.

Role of Intermediate-Conductance Calcium-Activated Potassium Channels in Osteoclastogenesis and Osteoclasts in Mice.

The results demonstrate the role of SK4 channels (SK4) during osteoclastogenesis by using SK4$^{-/-}$ knockout mice and pharmacological inhibition.

Figures 4A, 4B:
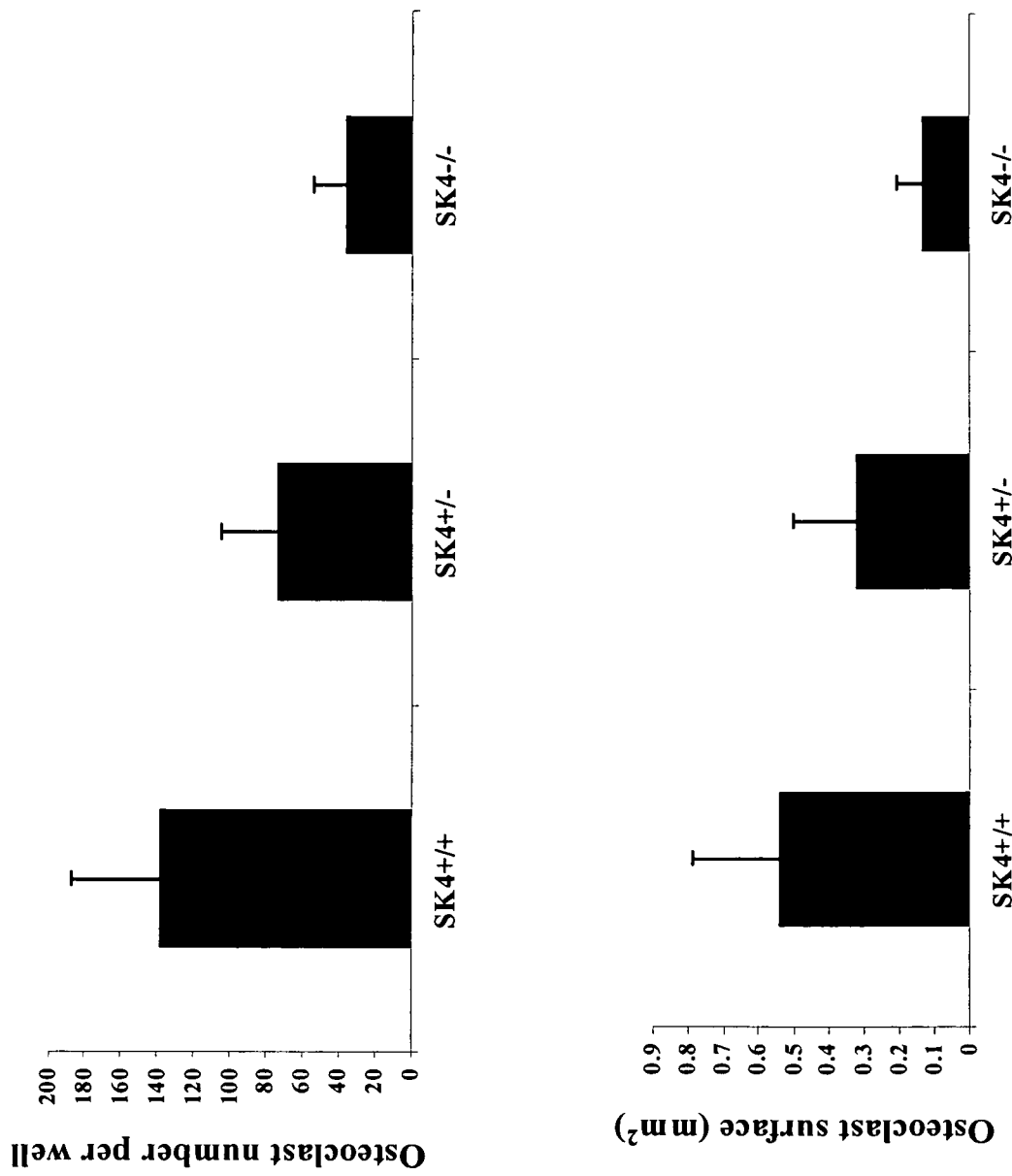
FIG. 4A shows decreased osteoclast-like cells (i.e., TRAP$^+$) generated from splenocytes of heterozygous (sk4$^{+/-}$) and homozygous knockout (sk4$^{-/-}$) mice for SK4 channels cultured under M-CSF and RANKL for seven days when compared to homozygous wild-type (WT; sk4$^{+/+}$) mice.
FIG. 4B shows decreased surface area of these cells when compared to WT mice.
Figure 5:
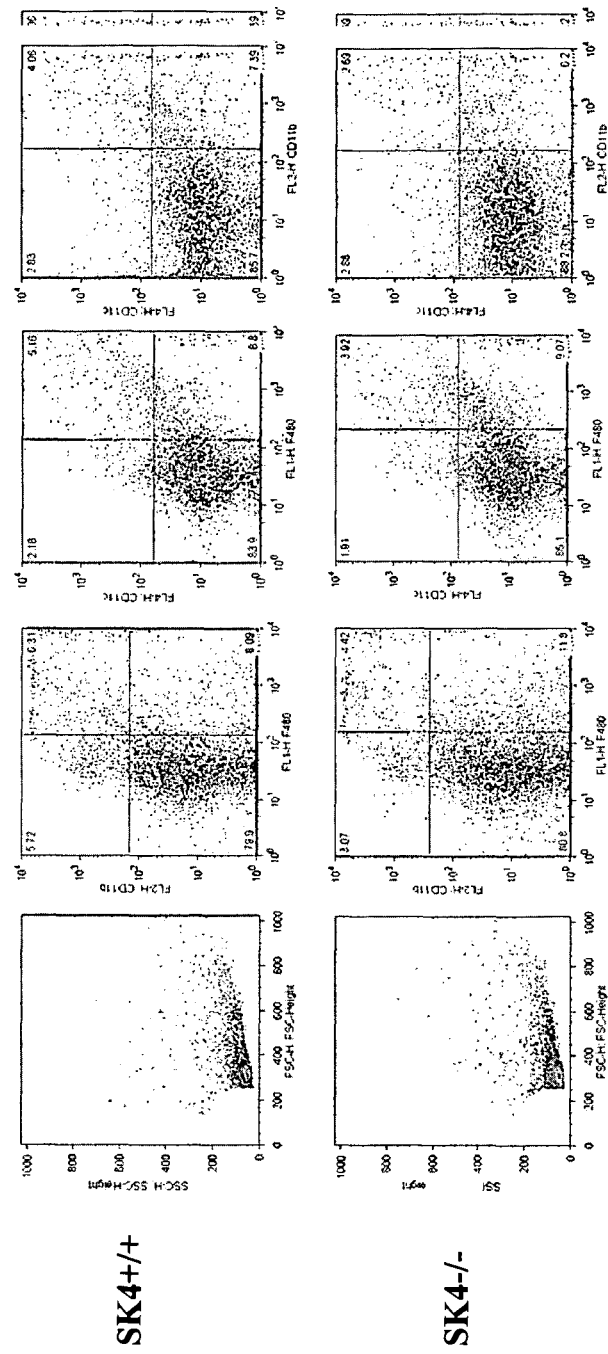
FIG. 5 shows that a deficiency in SK4 channel does not significantly affect the relative proportion of macrophages from homozygous knockout (sk4$^{-/-}$) mice (bottom panels) when compared to WT (sk4$^{+/+}$) mice (top panels). FACS graphs are presented from left to right as different combinations (all cells, CD11b/F480, CD11C/F480, CD11C/CD11b).

Splenocytes from SK4$^{-/-}$ mice showed a defect in osteoclastogenesis, as these cells failed to form the same number or size of osteoclasts as cells from SK4$^{+/-}$ or WT mice (FIGS. 4A-B). However, deficiency of SK4 channels alone did not affect the relative proportion of B-cells (B220), T-cells (CD4 and CD8), macrophages/granulocytes (GR1, CD11b), macrophages (F480, CD11b, CD11c) or dendritic cells (MHCII, CD8, CD11c) in the SK4$^{-/-}$ mice (FIG. 5).

Figure 6A:
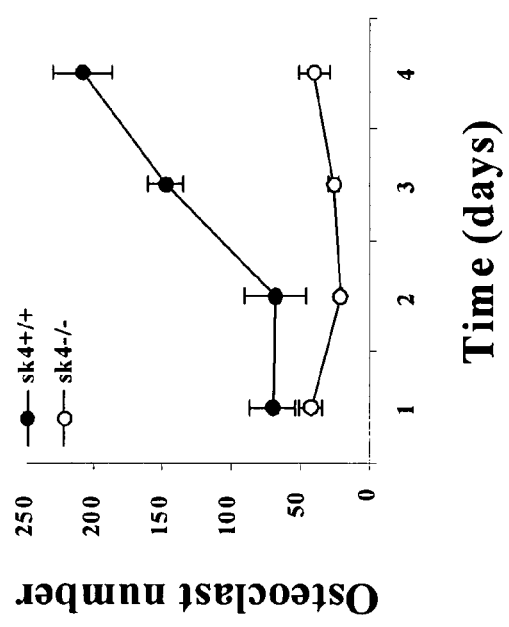
FIG. 6A shows decreased osteoclast-like cells (i.e., TRAP$^+$) generated from bone marrow-derived macrophages from homozygous knockout (sk4$^{-/-}$) mice cultured under fusogenic conditions (M-CSF+RANKL) for seven days when compared to WT (sk4$^{+/+}$) mice.
Figure 6B:
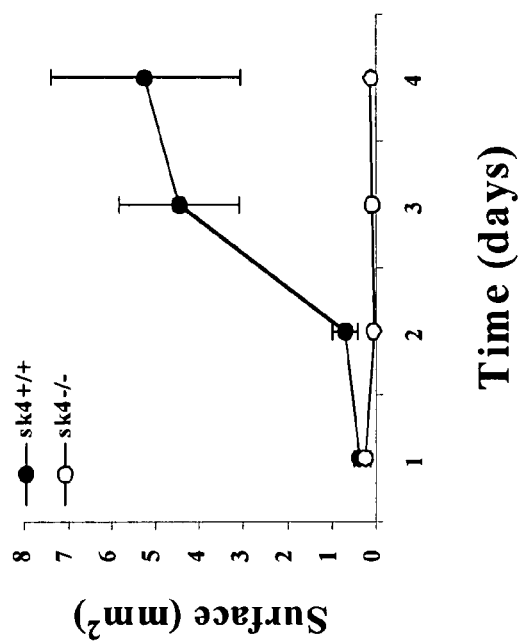
FIG. 6B shows decreased total surface area of these cells when compared to WT mice.

Likewise, bone marrow-derived macrophages from SK4$^{-/-}$ mice showed a defect in osteoclastogenesis that was similar to that observed in splenocyte-derived cells (FIGS. 6A-B). A lack of SK4 channels in macrophages from SK4$^{-/-}$ mice was confirmed by patch clamp studies, which showed defective SK4 channel activity (data not shown).

Interestingly, SK4$^{-/-}$ knockout mice showed increased trabecular bone density (data not shown). Both male and female SK4$^{-/-}$ knockout mice showed an 87% protection in bone erosion when compared to homozygous wild-type mice. In addition, osteoclasts from SK4$^{-/-}$ knockout mice did not resorb calcium-phosphate substrates efficiently (data not shown) when compared to osteoclasts from WT mice.

Figure 7:
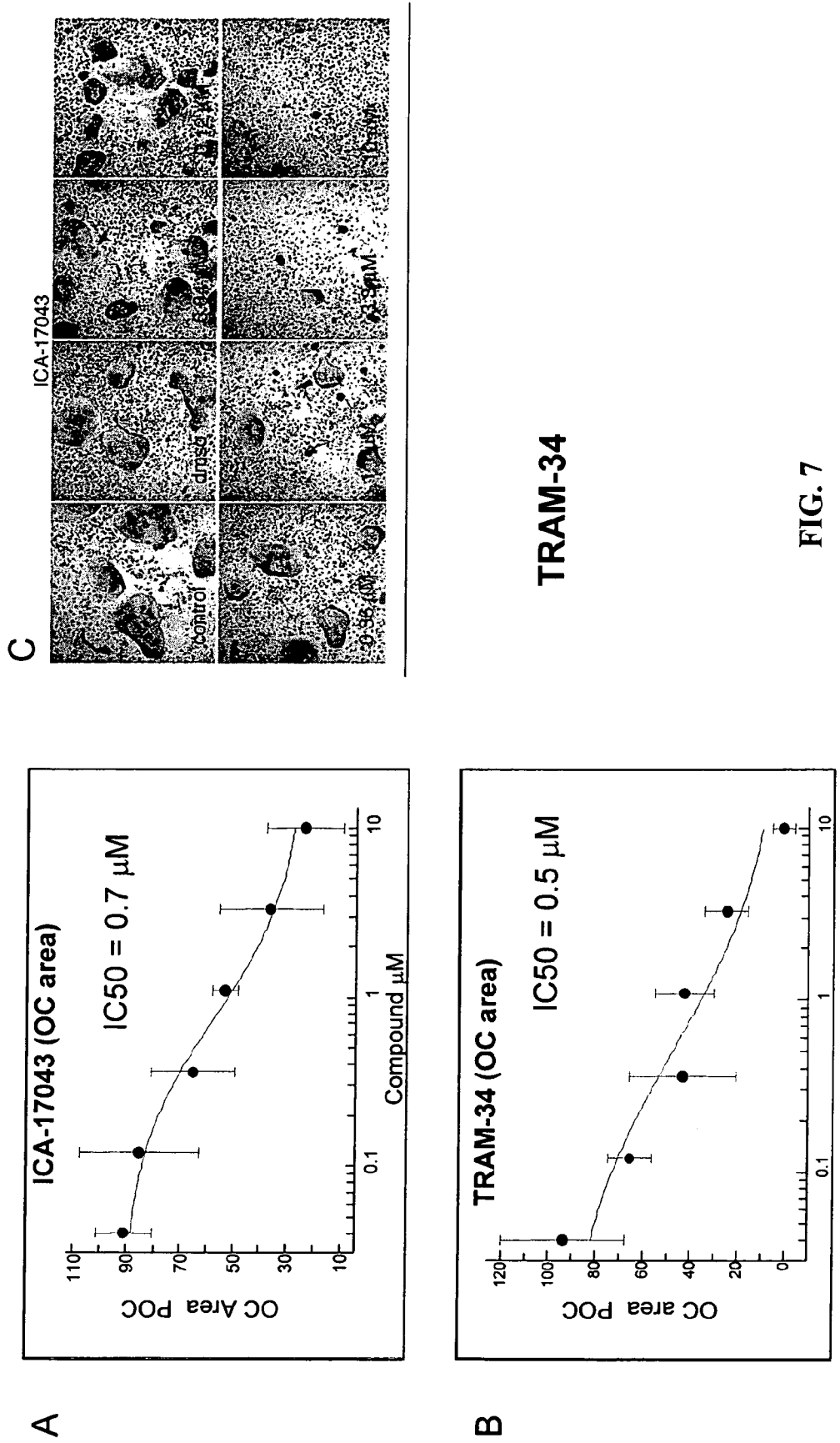
FIGS. 7A-B show that two different SK4 channel inhibitors (ICA-17043, FIG. 7A; and TRAM-34, FIG. 7B) prevent osteoclastogenesis in a dose-dependent manner in bone marrow-derived macrophages of WT mice. The surface area of TRAP$^+$ osteoclast-like cells were assessed (POC is percent relative to a no compound control). Data were derived from five replicates and the error bars represent standard deviation.
FIG. 7C shows the TRAP-stained image of ICA-17043-treated samples.

The role of SK4 channels in osteoclastogenesis was confirmed with two SK4 channel inhibitors, ICA-17043 and TRAM-34. These inhibitors attenuated osteoclastogenesis in a dose dependent manner in bone marrow-derived macrophages from WT mice (i.e., SK4$^{+/+}$) (FIGS. 7A-B). FIG. 7C shows TRAP-stained images of ICA-17043-treated samples, in which cell fusion was significantly inhibited at 0.36 μM.

Role of Intermediate-Conductance Calcium-Activated Potassium Channels in a Mouse Model of Rheumatoid Arthritis.

These results demonstrate that a deficiency or pharmacological inhibition of SK4 channels in mice prevented bone resorption in rheumatoid arthritis.

Figures 9A, 9B:
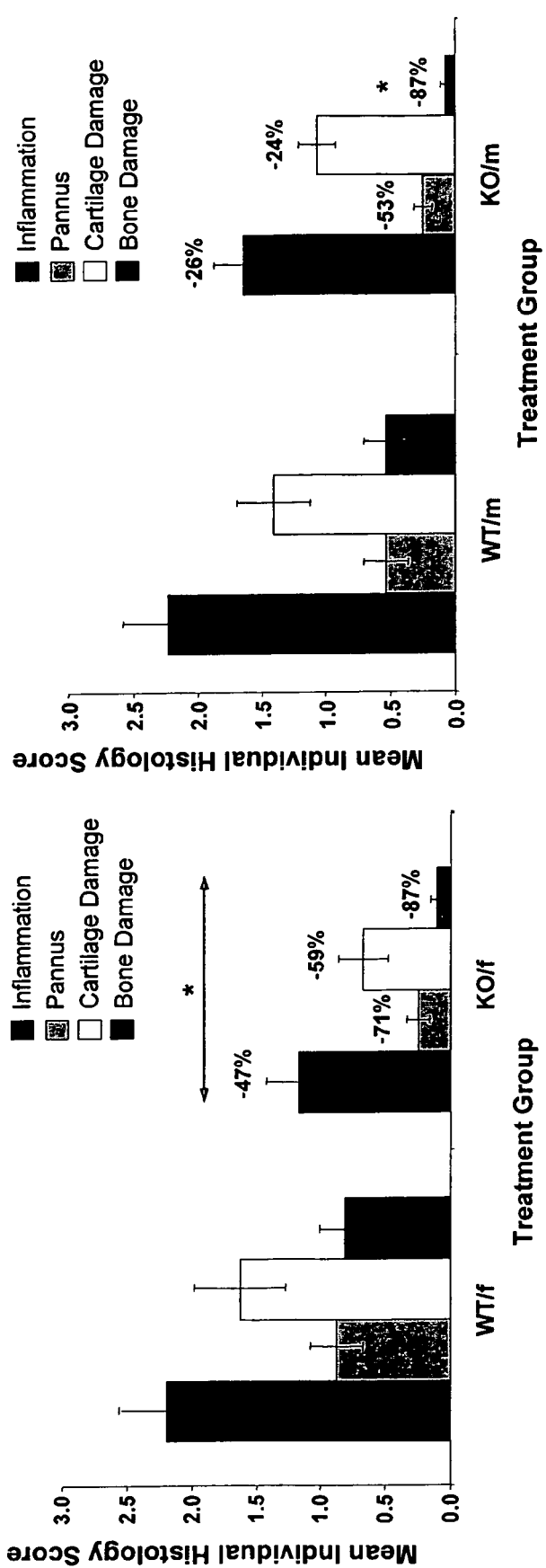
FIG. 9A shows significantly reduced histological scores in bone damage, cartilage damage, pannus and inflammation in paw joints of homozygous knockout (sk4$^{-/-}$) mice (female (F)) when compared to WT mice in the anti-collagen antibody-induced arthritis model (Experiment 2 from FIG. 8).
FIG. 9B shows significant reduced bone damage in homozygous knockout (sk4$^{-/-}$) mice (male (M)) when compared to WT mice in the anti-collagen antibody-induced arthritis model.

In repeat studies, SK4-deficient mice showed significantly attenuated arthritis scores (FIGS. 8A-B) and a substantial protection against bone erosion when compared to WT mice. In addition, paws from SK4-deficient mice had significantly less bone damage (FIGS. 9A-B). Female SK4-deficient mice, however, also had significantly less inflammation, pannus and cartilage damage (FIG. 9A).

Figure 11A:
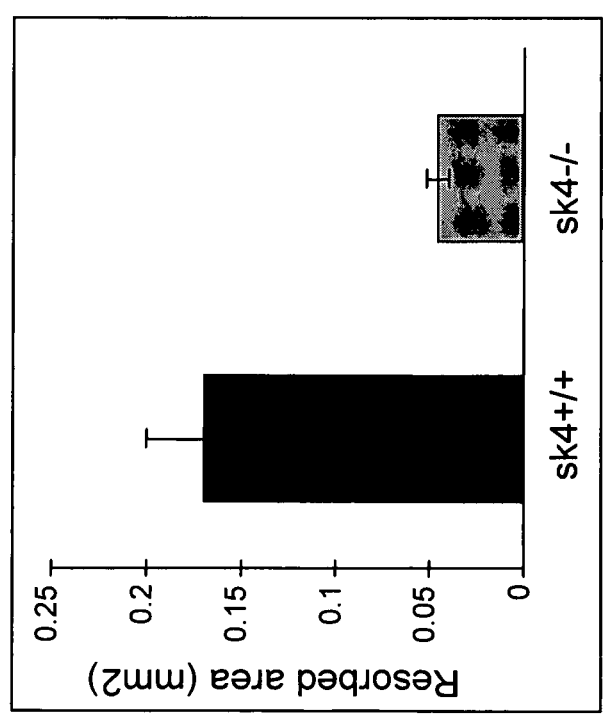
FIG. 11A shows that SK4-deficient osteoclasts are defective in resorbing bone minerals. Bone marrow-derived macrophages derived from sk4$^{+/+}$ and sk4$^{-/-}$ mice were cultured in the presence of M-CSF (20 ng/ml) and RANKL (100 ng/ml) for 20 days on BioCoat™ Osteologic™ slides that are coated with artificial bone made of calcium-phosphate crystals. Osteoclast activity was assessed by recording the calcium-phosphate surface area dissolved per well. Results are representative of three independent experiments (n=3; SD). Representative images of resorption pits from sk4$^{+/+}$ and sk4$^{-/-}$ mice are shown in FIG. 11B.
Figure 11B:
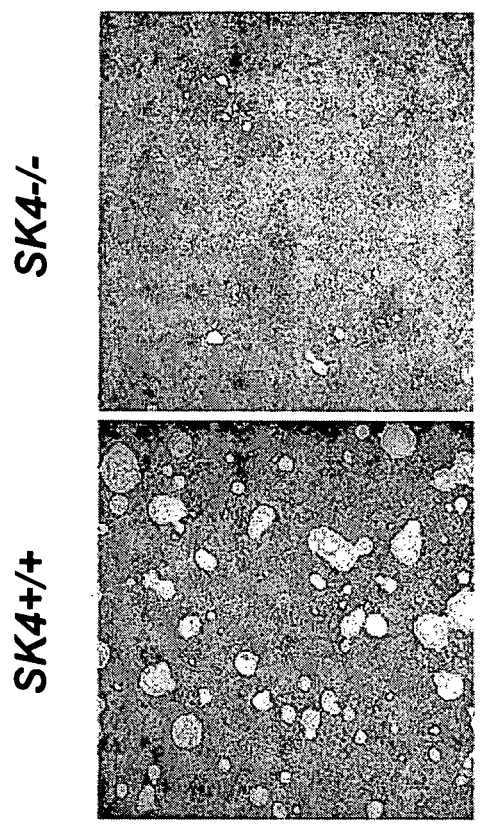
Figure 12:
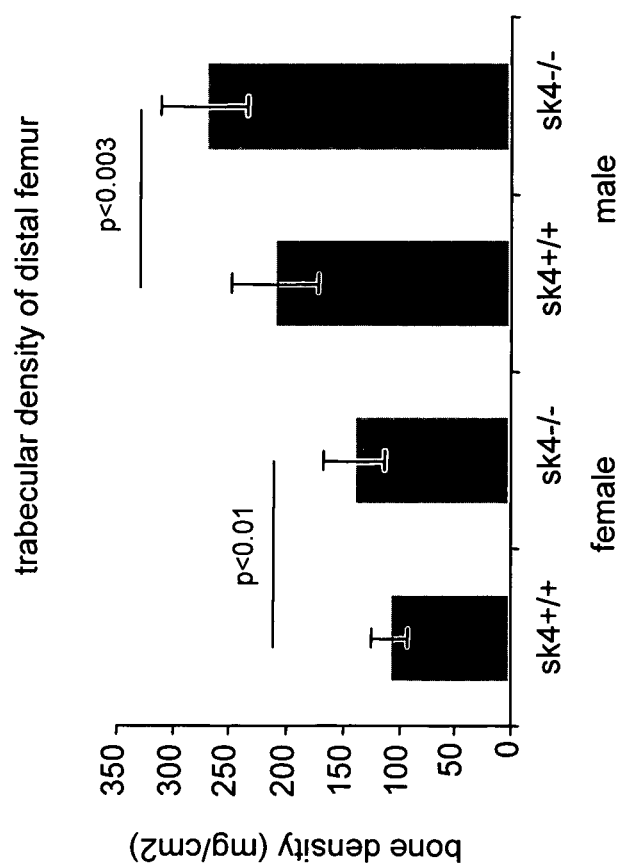
FIG. 12 shows that SK4-deficient mice have increased trabecular bone density. Distal femurs from male and female sk4$^{-/-}$ mice have a higher trabecular density than from sk4$^{+/+}$ mice. Distal femurs from eight-week-old male and female sk4$^{-/-}$ and sk4$^{+/+}$ mice were scanned using pQCT (n=8; SD).

Further studies showed that osteoclasts from SK4-deficient mice were defective in resorbing bone minerals (FIG. 11A), which likely was because the SK4$^{-/-}$ cells failed to form sufficient numbers of osteoclasts (FIG. 11B). The decreased ostoclasts in SK4-deficient mice thus manifests in increased trabecular bone density. Distal femurs from male and female SK4$^{-/-}$ mice had a higher trabecular density than from SK4$^{+/+}$ mice (FIG. 12).

Intermediate-Conductance Calcium-Activated Potassium Channel Inhibitors Attenuate Fusion in Human Peripheral Blood Mononuclear Cells.

This example demonstrates that SK4 channel inhibitors prevent fusion of human cells in a manner similar to that shown above for mouse cells in Example 4.

Figure 10A:
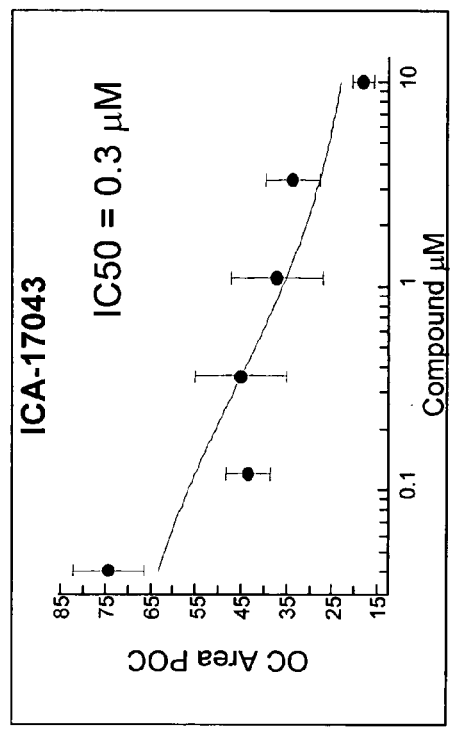
FIGS. 10A-B show that two different SK4 channel inhibitors (ICA-17043 and TRAM-34, FIGS. 10A and 10B, respectively) prevent osteoclastogenesis in a dose-dependent manner in human PBMCs under M-CSF+RANKL stimulation. The surface area of TRAP$^+$ osteoclast-like cells were assessed (POC is percent relative to a no compound control). Data were derived from four replicates and the error bars represent standard deviation.
Figure 10B:
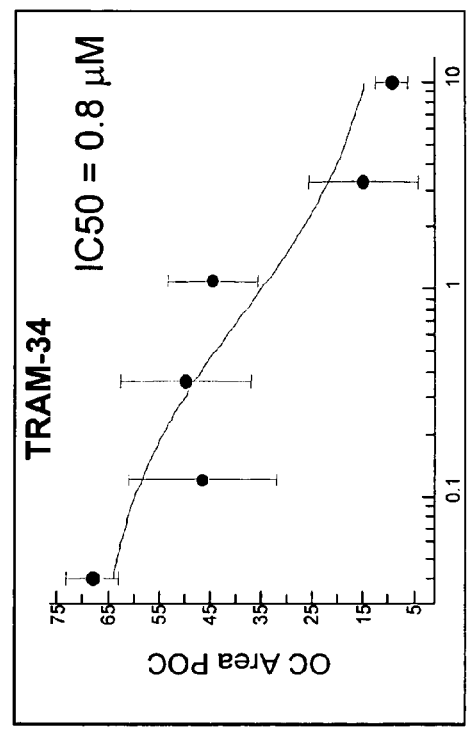

ICA-17043 and TRAM-34 inhibited human osteoclastogenesis in vitro in a dose-dependent manner (FIGS. 10A-B). ICA-17043 inhibited cell fusion at 0.3 μM IC50; whereas TRAM-34 inhibited cell fusion at 0.8 μM IC50. Likewise, ICA-17043 and TRAM-34 decreased not only osteoclast number but also osteoclast surface area in a dose-dependent manner.

Calvarial LPS/In Vivo Bone Resorption Assay

These results demonstrate that SK4-deficient (SK4$^{-/-}$) mice show reduced osteoclast formation in vivo in response to local LPS calvarial injection.

In order to define the role of SK4 in the inflammation that causes rheumatoid arthritis, lipopolysaccharide (LPS) was injected locally subcutaneously above the calvarium to induce a localized, rapid and efficient inflammatory response that leads to the formation of osteoclasts that resorb bone. Anatomically, calvariae are separated by a suture, free of superficial blood vessels and nerves, and easy to locate (see FIG. 14). Results are shown in FIGS. 14 and 15A-C.

An absence of SK4, and thus SK4 channels, dramatically prevented bone resorption in response to local injection of LPS (FIG. 14). Note the bone surface augments when holes are being made by osteoclasts in calvaria bone of SK4$^{+/+}$ mice, but not in calvaria bone of SK4-deficient mice. Mice deficient in SK4 maintain a higher calvaria bone thickness and density 5 days after LPS injection (see FIG. 15A-C).

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims and list of embodiments disclosed herein. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

The invention claimed is:

1. An in vitro method for inhibiting cell fusion of a macrophage cell expressing an intermediate-conductance calcium-activated potassium (SK4) channel, the method comprising the step of contacting the macrophage cell with an effective amount of an SK4 channel inhibitor to inhibit macrophage cell fusion, wherein said SK4 channel inhibitor is a small molecule inhibitor that specifically binds to an SK4 channel monomer to prevent it from forming part of an SK4 channel homotetramer or specifically binds to an SK4 channel homotetramer thereby inhibiting SK4 channel activity or function.

2. The method of claim 1, wherein the macrophage cell fusion is homotypic or heterotypic.

3. The method of claim 1, wherein the small molecule inhibitor is selected from the group consisting of 1-[(2-chlorophenyl)-diphenylmethyl]-1H-imidazole; 2,2-bis(4-fluorophenyl)-2-phenylacetamide; 1-[(2-chlorophenyl)diphenylmethyl]-1H-pyrazole; 1-[(2-fluorophenyl)diphenylmethyl]-1H-pyrazole; 1-[(4-chlorophenyl)diphenylmethyl]-1H-pyrazole; 1-[(2-fluorophenyl)diphenylmethyl]-1H-pyrazole; and 1-[(2-chlorophenyl)diphenylmethyl]-1H-tetrazole.

4. The method of claim 1, wherein the small molecule inhibitor is 1-[(2-chlorophenyl)-diphenylmethyl]-1H-imidazole.

5. The method of claim 1, wherein the small molecule inhibitor is 2,2-bis(4-fluorophenyl)-2-phenylacetamide.

6. The method of claim 1, wherein the small molecule inhibitor is 1-[(2-chlorophenyl)diphenylmethyl]-1H-pyrazole.

7. The method of claim 1, further comprising the step of assaying for SK4 channel expression or activity in the macrophage cell.

* * * * *